United States Patent [19]
Doherty et al.

[11] Patent Number: 5,348,953
[45] Date of Patent: Sep. 20, 1994

[54] SUBSTITUTED AZETIDINONES AS ANTI-INFLAMMATORY AND ANTIDEGENERATIVE AGENTS

[75] Inventors: James B. Doherty, Montvale; Paul E. Finke, Milltown; William K. Hagmann, Westfield, all of N.J.; Amy L. Kissinger, Pittsburgh, Pa.; Malcolm MacCoss, Freehold; Shrenik K. Shah, Metuchen, both of N.J.

[73] Assignee: Merck & Co., Inc., Rahway, N.J.

[21] Appl. No.: 992,414

[22] Filed: Dec. 17, 1992

Related U.S. Application Data

[63] Continuation-in-part of Ser. No. 891,614, Jun. 1, 1992, abandoned, which is a continuation-in-part of Ser. No. 720,976, Jun. 25, 1991, abandoned, Ser. No. 720,977, Jun. 25, 1991, abandoned, and Ser. No. 852,854, Mar. 17, 1992.

[51] Int. Cl.$^5$ ............... A61K 31/395; C07D 205/08; C07D 403/12; C07D 413/12
[52] U.S. Cl. .................................. 514/210; 540/360
[58] Field of Search .................... 540/360; 514/210

[56] References Cited

U.S. PATENT DOCUMENTS

| | | | |
|---|---|---|---|
| 4,064,120 | 12/1977 | Krapcho et al. | 540/200 |
| 4,115,382 | 9/1978 | Krapcho et al. | 540/200 |
| 4,166,907 | 9/1979 | Krapcho et al. | 540/200 |
| 4,174,317 | 11/1979 | Krapcho | 540/200 |
| 4,260,743 | 4/1981 | Bose | 542/442 |
| 4,510,086 | 4/1985 | Ross et al. | 540/260 |
| 4,534,896 | 8/1985 | Treuner et al. | 514/210 |
| 4,559,335 | 12/1985 | Zahler | 514/210 |
| 4,576,749 | 3/1986 | Zahler et al. | 544/311 |
| 4,680,391 | 7/1987 | Firestone et al. | 544/355 |

FOREIGN PATENT DOCUMENTS

| | | |
|---|---|---|
| 295547 | 5/1971 | Austria . |
| 375640 | 9/1981 | Austria . |
| 0023097 | 1/1981 | European Pat. Off. . |
| 0042026 | 12/1981 | European Pat. Off. . |
| 0076621 | 4/1983 | European Pat. Off. . |
| 0199630 | 4/1983 | European Pat. Off. . |
| 199630 | 4/1985 | European Pat. Off. . |
| 0267723 | 5/1988 | European Pat. Off. . |
| 0337549 | 8/1989 | European Pat. Off. . |
| 337549 | 10/1989 | European Pat. Off. . |
| 1945542 | 3/1971 | Fed. Rep. of Germany . |
| 2046822 | 3/1972 | Fed. Rep. of Germany . |
| 2046823 | 3/1972 | Fed. Rep. of Germany . |
| 2748827 | 3/1978 | Fed. Rep. of Germany . |
| 2824554 | 12/1978 | Fed. Rep. of Germany . |
| 2842466 | 4/1979 | Fed. Rep. of Germany . |
| 2911589 | 9/1979 | Fed. Rep. of Germany . |
| 3007298 | 3/1981 | Fed. Rep. of Germany . |
| WO93/00332 | 1/1993 | PCT Int'l Appl. . |
| 1192952 | 5/1970 | United Kingdom . |
| 1604752 | 12/1981 | United Kingdom . |
| 2093839 | 8/1982 | United Kingdom . |

OTHER PUBLICATIONS

Yoshifuji, Chemical Abstracts, vol. 105. Abs. 97895t (1986).

Peitsch, Hartmut, Tetrahedron Letters No. 45 pp. 4053-4056 (1976).

Tanaka, et al Heterocycles vol. 24, No. 9, pp. 2539-2543 (1986).

Primary Examiner—Mark L. Berch
Attorney, Agent, or Firm—Curtis C. Panzer; David L. Rose; Joseph F. DiPrima

[57] ABSTRACT

New substituted azetidinones of the general formula (I) which have been found to be potent elastase inhibitors and thereby useful anti-inflammatory and antidegenerative agents are described.

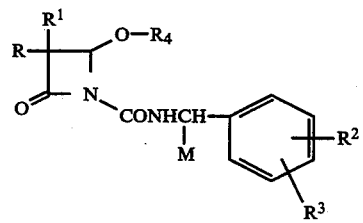

27 Claims, No Drawings

SUBSTITUTED AZETIDINONES AS ANTI-INFLAMMATORY AND ANTIDEGENERATIVE AGENTS

This application is a continuation-in-part of U.S. Ser. No. 891,614 filed Jun. 1, 1992 now abandoned which is a continuation-in-part of U.S. Ser. No. 720,976 now abandoned filed Jun. 25, 1991; U.S. Ser. No. 720,977 now abandoned filed Jun. 25, 1991; and U.S. Ser. No. 852,854 filed Mar. 17, 1992 pending.

BACKGROUND OF THE INVENTION

We have found that a group of new substituted azetidinones are potent elastase inhibitors and therefore are useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodontitis, cystic fibrosis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, TIBS, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, pp. 196–206, 1979.

In a second aspect this invention concerns the use of novel azetidinones in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation. We have found that the substituted azetidinones disclosed herein are potent inhibitors of proteinase 3 (PR-3), also known as myeloblastin.

See C. Labbaye, et al., Proc. Natl. Acad. Sci. USA, vol. 88, 9253–9256, (1991), Wegner autoantigen and myeloblastin are encoded by a single mRNA; D. Campanelli, et al., J. Exp. Med., vol. 172, 1709–1714, (1990), Cloning of cDNA for proteinase 3: A serine protease, antibiotic, and autoantigen from human neutrophils; and Bories, et. al., Cell, vol. 59, 959–968, (1989) Down-regulation of a serine protease, myeloblastin, causes growth arrest and differentiation of promyelocytic leukemia cells.

Recently, down regulation of PR-3 has been implicated in the proliferation and maintenance of a differentiated state of certain leukemia-cells. In particular, Bories, et. al., have shown that expression of this enzyme, hereinafter designated proteinase 3/myeloblastin, can be inhibited by treatment of HL-60 human leukemia cells with an antisense oligodeoxynucleotide and that such treatment induces differentiation and inhibits proliferation of these cells. Moreover, we have now demonstrated that the treatment of the HL-60 cell human leukemia cell line, among others, with the compounds of the instant invention, likewise results in the inhibition of proliferation and induction of differentiation in such cells.

Accordingly, we believe that treatment of leukemia such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation, comprising: administration of a therapeutically effective amount of compound of formula I will result in remission of the disease state. Administration may be either oral or parenteral.

BRIEF DESCRIPTION OF THE INVENTION

The instantly claimed invention is directed to specifically substituted azetidinones of Formula I

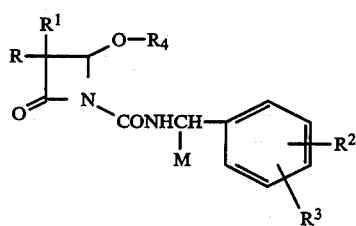

These substituted azetidinones have been found to be useful anti-inflammatory and antidegenerative agents. This invention is also directed to pharmaceutical compositions and methods of using these specifically substituted azetidinones. These compounds will also be useful in the treatment of certain leukemias and leukemia related conditions.

DETAILED DESCRIPTION OF THE INVENTION

This invention relates to potent elastase inhibitors of Formula (I),

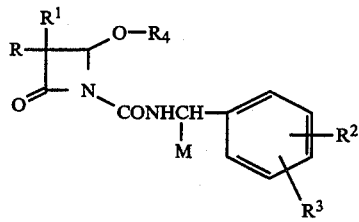

which are useful in the prevention, control and treatment of inflammatory and degenerative conditions especially arthritis and emphysema.

More particularly, the instant invention is directed to the compounds of the Formula (I)

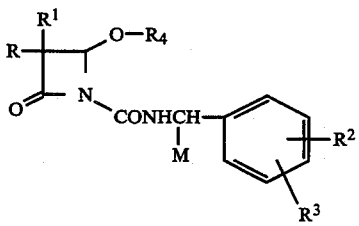

and pharmaceutically acceptable salts thereof wherein:

R is $C_{1-6}$ alkyl;

$R^1$ is $C_{1-6}$ alkyl or $C_{1-6}$ alkoxy-$C_{1-6}$ alkyl;

M is
  (1) hydrogen,
  (2) $C_{1-6}$ alkyl
  (3) hydroxy $C_{1-6}$ alkyl,
  (4) halo $C_{1-6}$ alkyl,
  (5) $C_{2-6}$ alkenyl, or
  (6) $C_{1-6}$ alkoxy-$C_{1-6}$ alkyl;

$R^2$ and $R^3$ are each independently
  (1) hydrogen,
  (2) $C_{1-6}$ alkyl,
  (3) halo,
  (4) carboxy,
  (5) $C_{1-6}$ alkoxy,
  (6) phenyl,
  (7) $C_{1-6}$ alkylcarbonyl,
  (8) amino wherein the amino is optionally mono or di substituted with $C_{1-6}$ alkyl, or $R^2$ and $R^3$ are joined together to form a furan or dioxacyclopentane ring;

$R_4$ is

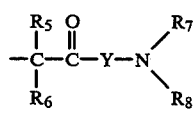

wherein $R_5$ and $R_6$ are each individually hydrogen or $C_{1-3}$ alkyl;

Y is  (a) 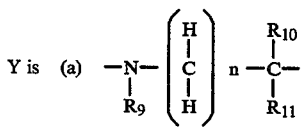

(b) 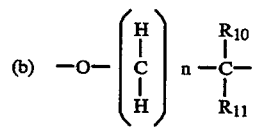

or (c) 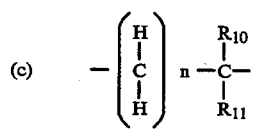

(d) a co-valent bond;

$R_7$ and $R_8$ are each individually
  (a) hydrogen,
  (b) $C_{1-6}$ alkyl,
  (c) hydroxy $C_{2-6}$alkyl,
  (d) $C_{3-5}$ cycloalkyl,
  (e) $C_{1-6}$ alkylcarbonyl,
  (f) $C_{1-6}$ alkyloxy carbonyl,
  (g) amino carbonyl $C_{0-6}$ alkyl, wherein the amino is optionally mono or di substituted with $C_{1-6}$ alkyl, or
  (h) carboxy $C_{1-6}$ alkyl,
  (i) $C_{1-6}$ alkoxycarbonyl $C_{1-6}$ alkyl,
  (j) mono or di substituted benzyl or mono or di substituted pyridylmethyl, wherein the substituents are $X_1$ and $X_2$, wherein
$X_1$ is
  (1) hydrogen,
  (2) halo,
  (3) $C_{1-6}$ alkyl,
  (4) halo-$C_{1-6}$ alkyl,
  (5) $C_{2-6}$ alkenyl,
  (6) hydroxy-$C_{1-6}$ alkyl,
  (7) $C_{1-6}$ alkylcarbonyl, or
  (8) $C_{1-6}$ alkylcarbonylamino; and $X_2$ is hydrogen, halo or $C_{1-6}$ alkyl;
n is 1, 2 or 3 when Y is definition (a) or (b) above; and n is 0, 1, 2 or 3 when Y is definition (c) above;
$R_9$, $R_{10}$ and $R_{11}$ are each independently selected from hydrogen, $C_{1-4}$ alkyl, and $C_{1-3}$ alkoxy $C_{1-3}$ alkyl; or
wherein $R_7$ and $R_8$ are joined together to form mono or di substituted ring of 5, 6, or 7 atoms selected from
  (1) piperidinyl,
  (2) piperazinyl,
  (3) morpholinyl,
  (4) pyrroylidinyl,
  (5) pyrryl, and
  (6) imidazolyl,
wherein the substituents are each selected from the group consisting of hydrogen and $C_{1-3}$ alkyl; or $R_8$ and $R_9$ are joined together to form a ring of 6 to 7 atoms and having two hetero atoms; or $R_9$ and $R_{10}$ are joined together to form a ring of 5 to 7 atoms and having one hetero atom; or $R_8$ and $R_{10}$ are joined together to form a ring of 5 to 7 atoms and having one hetero atom.

In particular, $R_8$ and $R_9$ may be joined together to form a ring of 6 to 7 atoms and having two hetero atoms including the nitrogens to which they are attached such as piperazinyl or homopiperazinyl. Similarly $R_9$ and $R_{10}$ may be joined together to form a ring of 5 to 7 atoms and having one hereto atom including the nitrogen to which $R_9$ is attached such as pyrrolidinyl or piperidinyl. The ring formed by joining $R_8$ and $R_{10}$ or $R_8$ and $R_9$ may be mono or di substituted with groups such as hydrogen, $C_{1-3}$ alkyl and cyclopropyl. The ring formed by joining $R_9$ and $R_{10}$ may be mono or di substituted with groups such as hydrogen and $C_{1-3}$ alkyl.

As appreciated by those of Skill in the art the term "alkyl" such as in $C_{1-6}$ alkyl, includes, Methyl, ethyl, propyl, butyl, pentyl, and hexyl, and where appropriate, branched chained forms including isopropyl and tert-butyl.

As further appreciated by those of skill in the art the term "dioxacyclopentane ring" is an alternate way of expressing the situation where $R_2$ and $R_3$ are joined together to form the group methylenedioxy.

As may also be appreciated by those of skill in the art, the $(CH_2)n$ spacer in definition Y, may, in the alternative be placed to the right of $CR_{10}R_{11}$.

In one embodiment, the invention concerns compounds of Formula I

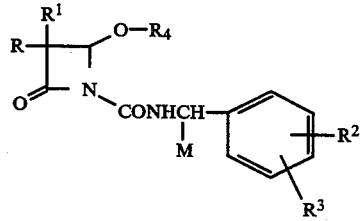

and pharmaceutically acceptable salts thereof wherein:
R is $C_{1-6}$ alkyl;
$R^1$ is $C_{1-6}$ alkyl or $C_{1-6}$ alkoxy-$C_{1-6}$ alkyl;
M is
  (1) hydrogen,
  (2) $C_{1-6}$ alkyl,
  (3) hydroxy $C_{1-6}$ alkyl,
  (4) halo $C_{1-6}$ alkyl,
  (5) $C_{2-6}$ alkenyl, or
  (6) $C_{1-6}$ alkoxy-$C_{1-6}$ alkyl;
$R^2$ and $R^3$ are each independently
  (1) hydrogen,
  (2) $C_{1-6}$ alkyl,
  (3) halo,
  (4) carboxy,
  (5) $C_{1-6}$ alkoxy,
  (6) phenyl,
  (7) $C_{1-6}$ alkylcarbonyl,
  (8) amino wherein the amino is optionally mono or di substituted with $C_{1-6}$alkyl, or
$R^2$ and $R^3$ are joined together to form a furan or dioxacyclopentane ring;

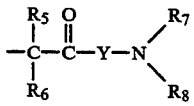

$R_5$ and $R_6$ are each individually hydrogen or $C_{1-3}$ alkyl;
Y is

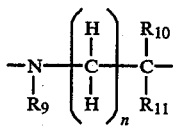

$R_7$ and $R_8$ are each individually
(a) hydrogen,
(b) $C_{1-6}$ alkyl,
(c) hydroxy $C_{2-6}$ alkyl,
(d) $C_{3-5}$ cycloalkyl,
(e) $C_{1-6}$ alkylcarbonyl,
(f) $C_{1-6}$ alkyloxy carbonyl,
(g) amino carbonyl $C_{0-6}$ alkyl, wherein the amino is optionally mono or di substituted with $C_{1-6}$ alkyl, or
(h) carboxy $C_{1-6}$ alkyl,
(i) $C_{1-6}$ alkoxycarbonyl $C_{1-6}$ alkyl,
(j) mono or di substituted benzyl or mono or di substituted pyridylmethyl, wherein the substituents are $X_1$ and $X_2$,
wherein
$X_1$ is
(1) hydrogen,
(2) halo,
(3) $C_{1-6}$ alkyl,
(4) halo-$C_{1-6}$ alkyl,
(5) $C_{2-6}$ alkenyl,
(6) hydroxy-$C_{1-6}$ alkyl,
(7) $C_{1-6}$ alkylcarbonyl, or
(8) $C_{1-6}$ alkylcarbonylamino; and
$X_2$ is hydrogen, halo or $C_{1-6}$ alkyl;
n is 1, 2 or 3; and
$R_9$, $R_{10}$ and $R_{11}$ are each independently selected from hydrogen, $C_{1-4}$ alkyl, and $C_{1-3}$ alkoxy $C_{1-3}$ alkyl; or
wherein $R_7$ and $R_8$ are joined together to form mono or di substituted ring of 5, 6, or 7 atoms selected from
(1) piperidinyl,
(2) piperazinyl,
(3) morpholinyl,
(4) pyrroylidinyl,
(5) pyrryl, and
(6) imidazolyl,
wherein the substituents are each selected from the group consisting of hydrogen and $C_{1-3}$ alkyl; or $R_8$ and $R_9$ are joined together to form a ring of 6 to 7 atoms and having two hereto atoms; or $R_9$ and $R_{10}$ are joined together to form a ring of 5 to 7 atoms and having one hereto atom.

In one class of the first embodiment, are the compounds wherein at least one of $R_5$ and $R_6$ is other than hydrogen.

Within this class is the sub-class of compounds of Formula I

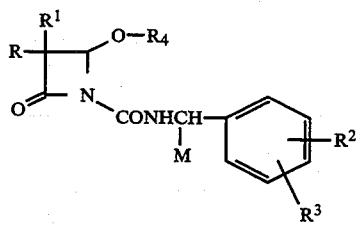

wherein

R is $C_{1-3}$ alkyl;
$R_1$ is $C_{1-3}$ alkyl;
M is
(a) $C_{1-6}$ alkyl, or
(b) $C_{2-6}$ alkenyl;
$R^2$ is
(a) hydrogen
(b) $C_{1-6}$ alkyl, or $C_{1-6}$ alkoxy, and
$R^3$ is hydrogen, or
$R^2$ and $R^3$ are joined together to form a furan or dioxacyclopentane ring;
$R_5$ and $R_6$ are each individually hydrogen or $C_{1-3}$ alkyl;
Y is

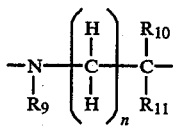

$R_7$ and $R_8$ are each independently selected from
(a) hydrogen,
(b) $C_{1-3}$ alkyl, 2-hydroxyethyl or cyclopropyl,
(c) $C_{1-3}$ alkcarbonyl,
(d) $C_{1-3}$ alkoxy $C_{2-3}$ alkyl,
(e) $C_{1-3}$ alkoxycarbonyl $C_{1-3}$ alkyl,
(f) $C_{1-3}$ alkoxy carbonyl,
(g) aminocarbonyl $C_{1-3}$ alkyl wherein the amino is optionally mono or di substituted with $C_{1-6}$ alkyl,
(h) substituted benzyl wherein the substituents are $X_1$ and $X_2$
wherein $X_1$ is hydrogen and $X_2$ is
(1) hydrogen,
(2) halo, or
(3) $C_{1-3}$ alkyl;
n is 1 or 2, and
$R_9$, $R_{10}$ and $R_{11}$ are each independently selected from hydrogen, $C_{1-4}$ alkyl, and $C_{1-3}$ alkoxy $C_{1-3}$ alkyl; or
$R_7$ and $R_8$ are joined together to form a substituted ring selected from
(a) piperidinyl,
(b) piperazinyl, and
(c) morpholinyl;
or
$R_8$ and $R_9$ are joined together to form a ring of 6 to 7 atoms and having two hetero atoms; or $R_9$ and $R_{10}$ are joined together to form a ring of 5 to 7 atoms and having one hetero atom.

Within this sub-class are the compounds wherein
R is methyl or ethyl;
$R_1$ is methyl or ethyl;
M is
(a) $C_{1-4}$ alkyl, or
(b) $C_{2-3}$ alkenyl;
$R^2$ is
(a) hydrogen,
(b) $C_{1-3}$ alkyl, or $C_{1-3}$ alkoxy, and
$R^3$ is hydrogen, or
$R^2$ and $R^3$ are joined together to form a furan or dioxacyclopentane ring;
$R_5$ and $R_6$ are each individually hydrogen or methyl;
Y is

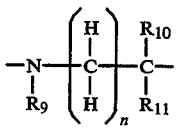

R7 and R8 are each independently selected from
(a) C$_{1-3}$ alkyl, 2-hydroxyethyl or cyclopropyl,
(b) C$_{1-3}$ alkoxy C$_{2-3}$ alkyl,
(c) acetyl,
(d) C$_{1-3}$ alkoxycarbonylmethyl,
(e) aminocarbonyl methyl,
(f) hydrogen, R9, R10 and R11 are each independently selected from
(a) C$_{1-3}$ alkyl,
(b) C$_{1-3}$ alkoxy C$_{1-3}$ alkyl,
(c) Hydrogen, or R7 and R8 are joined together to form a substituted ring selected from
(a) piperidinyl,
(b) piperizinyl, and
(c) morpholinyl, or R8 and R9 are joined together to form a substituted piperizinyl ring.

In a second class of the first embodiment, are the compounds wherein R5 and R6 are each hydrogen.

Within this class is the sub-class of compounds of Formula I

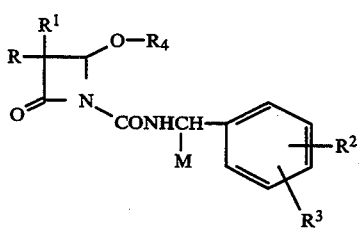

wherein
R is C$_{1-3}$ alkyl;
R1 is C$_{1-3}$ alkyl;
M is
(a) C$_{1-6}$ alkyl, or
(b) C$_{2-6}$ alkenyl;
R$^2$ is
(a) hydrogen
(b) C$_{1-6}$ alkyl, or C$_{1-6}$ alkoxy, and
R$^3$ is hydrogen, or
R$^2$ and R$^3$ are joined together to form a furan or dioxacyclopentane ring;
Y is

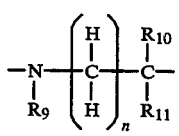

R7 and R8 are each individually
(a) hydrogen,
(b) C$_{1-6}$ alkyl,
(c) hydroxy C$_{2-6}$ alkyl,
(d) C$_{3-5}$ cycloalkyl,
(e) C$_{1-6}$ alkylcarbonyl,
(f) C$_{1-6}$ alkyloxy carbonyl,
(g) amino carbonyl C$_{0-6}$ alkyl, wherein the amino is optionally mono or di substituted with C$_{1-6}$ alkyl, or
(h) carboxy C$_{1-6}$ alkyl,
(i) C$_{1-6}$ alkoxycarbonyl C$_{1-6}$ alkyl,
(j) substituted benzyl or pyridylmethyl wherein the substituents are X$_1$ and X$_2$
wherein X$_1$ is hydrogen and X$_2$ is
(1) hydrogen
(2) halo or
(3) C$_{1-3}$ alkyl;
n is 1, 2 or 3; and
R9, R10 and R11 are each independently selected from hydrogen, C$_{1-4}$ alkyl, and C$_{1-3}$ alkoxy C$_{1-3}$ alkyl; or
wherein R7 and R8 are joined together to form mono or di substituted ring of 5, 6, or 7 atoms selected from
(1) piperidinyl,
(2) piperazinyl,
(3) morpholinyl,
(4) pyrroylidinyl,
(5) pyrryl, and
(6) imidazoiyl,
wherein the substituents are each selected from the group consisting of hydrogen and C$_{1-3}$ alkyl; or R8 and R9 are joined together to form a ring of 6 to 7 atoms and having two hetero atoms; or R9 and R10 are joined together to form a ring of 5 to 7 atoms and having one hetero atom.

Within this sub-class are the compounds wherein
R is methyl or ethyl;
R$_1$ is methyl or ethyl;
M is
(a) C$_{1-4}$ alkyl, or
(b) C$_{2-3}$ alkenyl;
R$^2$ is
(a) hydrogen,
(b) C$_{1-3}$ alkyl, or C$_{1-3}$ alkoxy, and
R$^3$ is hydrogen, or
R$^2$ and R$^3$ are joined together to form a furan or dioxacyclopentane ring;
Y is

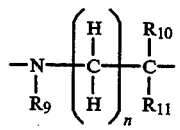

R7 and R8 are each independently selected from
(a) C$_{1-3}$ alkyl, 2-hydroxyethyl or cyclopropyl,
(b) C$_{1-3}$ alkoxy C$_{1-3}$ alkyl,
(c) Hydrogen,
(d) aminocarbonylmethyl wherein the amino group is optionally mono or di substituted with C$_{1-3}$ alkyl,
n is 1 or 2; and
R9, R10 and R11 are each independently selected from hydrogen, C$_{1-4}$ alkyl, and C$_{1-3}$ alkoxy C$_{1-3}$ alkyl; or
wherein R7 and R8 are joined together to form mono or di substituted ring of 5, 6, or 7 atoms selected from
(1) piperidinyl,
(2) morpholinyl, and
(3) imidazolyl, wherein the substituents are each selected from the group consisting of hydrogen and $C_{1-3}$ alkyl; or $R_8$ and $R_9$ are joined together to form a piperazinyl ring; or $R_9$ and $R_{10}$ are joined together to form a piperidine ring.

In a second embodiment, the invention is directed to the compounds of the Formula (I)

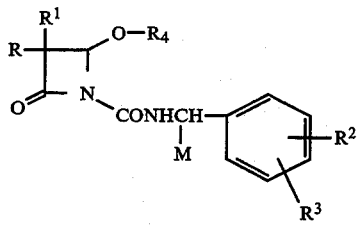

and pharmaceutically acceptable salts thereof wherein:
R is $C_{1-6}$ alkyl;
$R^1$ is $C_{1-6}$ alkyl or $C_{1-6}$ alkoxy-$C_{1-6}$ alkyl;
M is
 (1) hydrogen,
 (2) $C_{1-6}$ alkyl,
 (3) hydroxy $C_{1-6}$ alkyl,
 (4) halo $C_{1-6}$ alkyl,
 (5) $C_{2-6}$ alkenyl, or
 (6) $C_{1-6}$ alkoxy-$C_{1-6}$ alkyl;
$R^2$ and $R^3$ are each independently
 (1) hydrogen,
 (2) $C_{1-6}$ alkyl,
 (3) halo,
 (4) carboxy,
 (5) $C_{1-6}$ alkoxy,
 (6) phenyl,
 (7) $C_{1-6}$ alkylcarbonyl,
 (8) di-($C_{1-6}$ alkyl)amino, or $R^2$ and $R^3$ are joined together to form a furan or dioxacyclopentane ring;
$R_4$ is

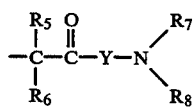

$R_5$ and $R_6$ are each individually hydrogen or $C_{1-3}$ alkyl;
Y is

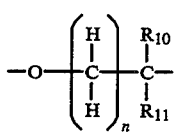

$R_7$ and $R_8$ are each individually
 (a) hydrogen,
 (b) $C_{1-6}$ alkyl, hydroxy-$C_{2-3}$ alkyl or cyclopropyl
 (c) $C_{1-6}$ alkyloxy $C_{2-6}$ alkyl;
n is 1, 2 or 3; and
$R_{10}$ and $R_{11}$ are each independently selected from hydrogen, $C_{1-4}$ alkyl, and $C_{1-3}$ alkoxy $C_{1-3}$ alkyl; or
wherein $R_7$ and $R_8$ are joined together to form mono or di substituted ring of 5, 6, or 7 atoms selected from
 (1) piperidinyl,
 (2) piperazinyl,
 (3) morpholinyl,
 (4) pyrroylidinyl,
 (5) pyrryl, and
 (6) imidazolyl,
wherein the substituents are each selected from the group consisting of hydrogen and $C_{1-3}$ alkyl.

In one class of the second embodiment, are the compounds wherein $R_5$ and $R_6$ are each hydrogen.

Within this class is the sub-class of compounds of Formula I

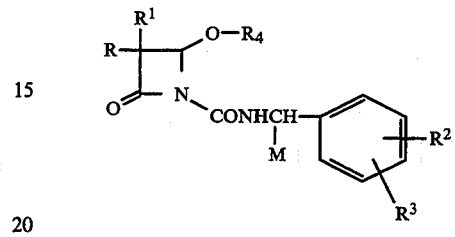

wherein
R is $C_{1-3}$ alkyl;
$R_1$ is $C_{1-3}$ alkyl;
M is
 (a) $C_{1-6}$ alkyl, or
 (b) $C_{2-6}$ alkenyl;
$R^2$ is
 (a) hydrogen
 (b) $C_{1-6}$ alkyl, or $C_{1-6}$ alkoxy, and
$R^3$ is hydrogen, or
$R^2$ and $R^3$ are joined together to form a furan or dioxacyclopentane ring;
Y is

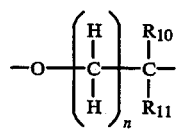

$R_7$ and $R_8$ are each independently selected from
 (a) hydrogen,
 (b) $C_{1-3}$ alkyl, hydroxy $C_{2-3}$ alkyl or cyclopropyl,
 (c) $C_{1-3}$ alkoxy $C_{2-3}$ alkyl,
or
$R_7$ and $R_8$ are joined together to form a substituted ring selected from
 (a) piperidinyl,
 (b) piperazinyl,
 (c) morpholinyl, and
 (d) imidazolyl.

Within this sub-class are the compounds wherein
R is methyl or ethyl;
$R_1$ is methyl or ethyl;
M is
 (a) $C_{1-4}$ alkyl, or
 (b) $C_{2-3}$ alkenyl;
$R^2$ is
 (a) hydrogen,
 (b) $C_{1-3}$ alkyl, or $C_{1-3}$ alkoxy, and
$R^3$ is hydrogen, or
$R^2$ and $R^3$ are joined together to form a furan or dioxacyclopentane ring;
Y is $$-O-\left(\begin{array}{c}H\\|\\C\\|\\H\end{array}\right)_n\begin{array}{c}R_{10}\\|\\C-\\|\\R_{11}\end{array}$$

$R_7$ and $R_8$ are each independently selected from
(a) $C_{1-3}$ alkyl, 2-hydroxyethyl or cyclopropyl,
(b) $C_{1-3}$ alkoxy $C_{2-3}$ alkyl, and
(b) hydrogen, or $R_7$ and $R_8$ are joined together to form a substituted ring selected from
(a) piperidinyl,
(b) morpholinyl, and
(c) imidazolyl.

In a third embodiment, the invention is directed to the compounds of the Formula (I)

$$\begin{array}{c}R^1\quad O-R_4\\R-\diagdown\diagup\\O=\diagup\diagdown N\diagdown\\\quad CONHCH\diagup\diagdown\diagdown\\\qquad M\qquad\diagdown\diagup-R^2\\\qquad\qquad\quad R^3\end{array}$$

and pharmaceutically acceptable salts thereof wherein:
R is $C_{1-6}$ alkyl;
$R^1$ is $C_{1-6}$ alkyl or $C_{1-6}$ alkoxy-$C_{1-6}$ alkyl;
M is
(1) hydrogen,
(2) $C_{1-6}$ alkyl,
(3) hydroxy $C_{1-6}$ alkyl,
(4) halo $C_{1-6}$ alkyl,
(5) $C_{2-6}$ alkenyl, or
(6) $C_{1-6}$ alkoxy-$C_{1-6}$ alkyl;
$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_6$ alkylcarbonyl,
(8) di-($C_{1-6}$ alkyl)amino, or
$R_2$ and $R_3$ are joined together to form a furan or dioxacyclopentane ring;
$R_4$ is $$\begin{array}{c}R_5\quad O\qquad R_7\\|\quad\|\qquad\diagup\\-C-C-Y-N\\|\qquad\qquad\diagdown\\R_6\qquad\qquad R_8\end{array}$$

$R_5$ and $R_6$ are each individually hydrogen or $C_{1-6}$ alkyl;
Y is
(a)

$$\left(\begin{array}{c}H\\|\\C\\|\\H\end{array}\right)_n\begin{array}{c}R_{10}\\|\\C-\\|\\R_{11}\end{array}$$

or
(b) a co-valent bond,
$R_7$ and $R_8$ are each individually
(a) hydrogen,
(b) $C_{1-6}$ alkyl, hydroxy $C_{2-3}$ alkyl or cyclopropyl,
(c) $C_{1-6}$ alkyloxy $C_{2-3}$ alkyl,
or wherein $R_7$ and $R_8$ are joined together to form mono or di substituted ring of 5, 6, or 7 atoms selected from
(1) piperidinyl,
(2) piperazinyl,
(3) morpholinyl,
(4) pyrroylidinyl,
(5) pyrryl, and
(6) imidazolyl,
wherein the substituents are each selected from the group consisting of hydrogen and $C_{1-3}$ alkyl; and wherein n is 0, 1, 2 or 3 and wherein $R_{10}$ and $R_{11}$, are each independently selected from hydrogen, $C_{1-3}$ alkyl, and $C_{1-3}$ alkoxy $C_{1-3}$ alkyl.

In one class of the third embodiment, are the compounds wherein $R_5$ and $R_6$ are each hydrogen.

Within this class is the sub-class of compounds of Formula I $$\begin{array}{c}R^1\quad O-R_4\\R-\diagdown\diagup\\O=\diagup\diagdown N\diagdown\\\quad CONHCH\diagup\diagdown\diagdown\\\qquad M\qquad\diagdown\diagup-R^2\\\qquad\qquad\quad R^3\end{array}$$

wherein
R is $C_{1-3}$ alkyl;
$R_1$ is $C_{1-3}$ alkyl;
M is
(a) $C_{1-6}$ alkyl, or
(b) $C_{2-6}$ alkenyl;
$R^2$ is
(a) hydrogen
(b) $C_{1-6}$ alkyl, or $C_{1-6}$ alkoxy, and
$R^3$ is hydrogen, or
$R^2$ and $R^3$ are joined together to form a furan or dioxacyclopentane ring;
Y is
(a)

$$\left(\begin{array}{c}H\\|\\C\\|\\H\end{array}\right)_n\begin{array}{c}R_{10}\\|\\C-\\|\\R_{11}\end{array}$$

wherein n is 0 or 1, or
(b) a co-valent bond;
$R_7$ and $R_8$ are each independently selected from
(a) hydrogen,
(b) $C_{1-3}$ alkyl, 2-hydroxyethyl or cyclopropyl, (c) $C_{1-3}$ alkoxy $C_{2-3}$ alkyl,
or
R$_7$ and R$_8$ are joined together to form a substituted ring selected from
(a) piperidinyl,
(b) piperazinyl,
(c) pyrrolidinyl,
(d) morpholinyl, and
(e) imidazolyl.
Within this sub-class are the compounds wherein
R is methyl or ethyl;
R$_1$ is methyl or ethyl;
M is
(a) $C_{1-4}$ alkyl, or
(b) $C_{2-3}$ alkenyl;
R$_2$ is
(a) hydrogen,
(b) $C_{1-3}$ alkyl, or $C_{1-3}$ alkoxy, and
R$_3$ is hydrogen, or
R$^2$ and R$^3$ are joined together to form a furan or dioxacyclopentane ring;
R$_5$ and R$_6$ are each individually hydrogen;
Y is
(a)

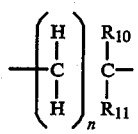

wherein n is 1, or
(b) a co-valent bond;
R$_7$ and R$_8$ are each independently selected from
(a) $C_{1-3}$ alkyl, 2-hydroxyethyl or cyclopropyl,
(b) $C_{1-3}$ alkoxy $C_{2-3}$ alkyl,
or
R$_7$ and R$_8$ are joined together to form a substituted ring selected from
(a) piperidinyl,
(b) morpholinyl, and
(c) imidazolyl.

In another aspect the present invention is directed to the treatment of leukemia, such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation with compounds of Formula I.

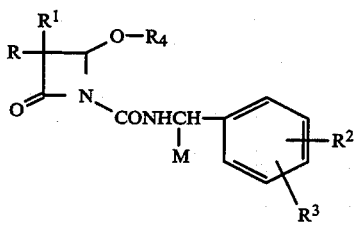

or a pharmaceutically acceptable salt thereof as defined in any of the alternative definitions provided above.
Treatment of leukemia cells comprising:
administration of a therapeutically effective amount of a compound of Formula I results in the inhibition of proteinase 3/myeloblastin, inhibition of elastase, inhibition of proliferation of the leukemia cells, induction of differentiation of the leukemia cells, and remission of the disease state.

In one alternative embodiment the invention concerns a method of treating leukemia comprising:
administration to a patient in need of such treatment of a therapeutically effective amount of compound of Formula I.

In a second alternative embodiment the invention concerns a method of inhibiting proteinase 3/myeloblastin, comprising:
administration to a patient in need of such inhibition of a therapeutically effective amount of compound of Formula I as defined above.

In a third alternative embodiment the invention concerns a method of inhibiting proteinase 3/myeloblastin and elastase, comprising:
administration to a patient in need of such inhibition of a therapeutically effective amount of compound of Formula I as or a pharmaceutically acceptable salt thereof as defined above.

In a fourth embodiment the invention concerns a method of inducing-cellular differentiation in leukemia cells comprising:
administration to a patient in need of such inhibition of a therapeutically effective amount of compound of Formula I or a pharmaceutically acceptable salt thereof as defined above.

Each of the above alternative embodiments (i.e., those relating to PR3 or cancer), also concerns co-administration of a compound of Formula I as defined above, with an agent or agents known in the art for treatment of leukemia, including, but not limited to epsilon-aminocaproic acid, heparin, trasylol (aprotinin); prednisolone; cytosine arabinoside; b-mercaptopurine; cytarabine; an anthracycline (see Young et. al. (1981) N. Engl. J. Med. 305:139) such as dauorubicin, doxorubicin and epidoxorubicin; Vitamin A derivatives including retinoids and all-trans-retinoic acid (See Ellison R. R. et.al. (1968) Blood 32:507, Arabinosyl Cytosine: A useful agent in the treatment of leukemia in adults; Cytarabine: Therapeutic new dimensions, Semin. Oncol. 12:1 (1985, supp 3); Weinstein H. J. et al. (1983) Blood 62:315, Chemotherapy for acute myelogenous leukemia in children and adults results in an enhanced therapeutic response.

Accordingly, in a fifth alternative embodiment the invention concerns a pharmaceutical composition comprising:
a pharmaceutical carrier, a therapeutically effective amount of compound selected from the group consisting of epsilon-aminocaproic acid, heparin, trasylol, prednisolone, cytosine arabinoside, $\beta$-mercaptopurine, cytarabine, an anthracycline and a vitamin A derivative such as retinoic acid; and a therapeutically effective amount of compound of Formula I as defined above In a sixth alternative embodiment the invention concerns a method of treating leukemia comprising:
co-administration to a patient in need of such treatment of a therepeutically effective amount of compound selected from the group consisting of epsilon-aminocaproic acid, heparin, trasylol, prednisolone, cytosine arabinoside, b-mercaptopurine, cytarabine, an anthracycline, and a vitamin A derivative; and a therapeutically effective amount of compound of Formula I as defined above In a seventh alternative embodiment the invention concerns a method of inhibiting proteinase 3/myeloblastin, comprising:

co-administration to a patient in need of such inhibition of a therapeutically effective amount of compound selected from the group consisting of epsilon-aminocaproic acid, heparin, trasylol, prednisolone, cytosine arabinoside, β-mercaptopurine, cytarabine, an anthracycline, and a vitamin A derivative; and a therapeutically effective amount of compound of Formula I as defined above In an eighth alternative embodiment the invention concerns a method of inhibiting proteinase 3/myeloblastin and elastase, comprising:

administration to a patient in need of such inhibition of a therapeutically effective amount of compound selected from the group consisting of epsilon-aminocaproic acid, heparin, trasylol, prednisolone, cytosine arabinoside, β-mercaptopurine, cytarabine, an anthracycline, and a vitamin A derivative; and a therapeutically effective amount of compound of Formula I as defined above In a ninth alternative embodiment the invention concerns a method of inducing cell differentiation in leukemia cells comprising:

administration to a patient in need of such inducing of a therapeutically effective amount of compound selected from the group consisting of epsilon-aminocaproic acid, heparin, trasylol, prednisolone, cytosine arabinoside, β-mercaptopurine, cytarabine, an anthracycline and a vitamin A derivative; and a therapeutically effective amount of compound of Formula I as defined above.

In an alternate embodiment the invention concerns compounds of Formula II that are intermediates in the production of compounds of Formula I

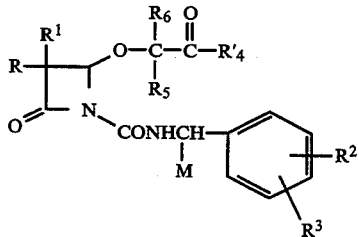

said intermediates wherein:
R is $C_{1-6}$ alkyl;
$R^1$ is $C_{1-6}$ alkyl or $C_{1-6}$ alkoxy-$C_{1-6}$ alkyl;
M is
  (1) hydrogen,
  (2) $C_{1-6}$ alkyl,
  (3) hydroxy $C_{1-6}$ alkyl,
  (4) halo $C_{1-6}$ alkyl,
  (5) $C_{2-6}$ alkenyl, or
  (6) $C_{1-6}$ alkoxy-$C_{1-6}$ alkyl;
$R^2$ and $R^3$ are each independently
  (1) hydrogen,
  (2) $C_{1-6}$ alkyl,
  (3) halo,
  (4) carboxy,
  (5) $C_{1-6}$ alkoxy,
  (6) phenyl,
  (7) $C_{1-6}$ alkylcarbonyl,
  (8) di-($C_{1-6}$ alkyl)amino, or $R^2$ and $R^3$ are joined together to form a furan or dioxacyclopentane ring;
$R'_4$ is hydroxy or chloro; and
$R_5$ and $R_6$ are each individually hydrogen or $C_{1-6}$ alkyl.

In the alternative, $R'_4$ may be a protected hydroxy or other activated ester such as isobutyloxycarbonyloxy, or benzotriazolyl-1-oxy.

One class concerns compounds for Formula II

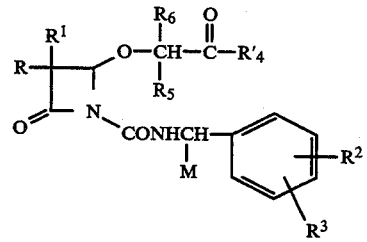

wherein
R is $C_{1-3}$ alkyl;
$R_1$ is $C_{1-3}$ alkyl;
M is
  (a) $C_{1-6}$ alkyl, or
  (b) $C_{2-6}$ alkenyl;
$R_2$ is
  (a) hydrogen
  (b) $C_{1-6}$ alkyl, or $C_{1-6}$ alkoxy, and
$R_3$ is hydrogen, or
$R_2$ and $R_3$ are joined together to form a furan or dioxacyclopentane ring;
$R'_4$ is hydroxy, chloro isobutyloxycarbonyloxy or benzotriazolyl-1-oxy; and
$R_5$ and $R_6$ are each individually hydrogen or $C_{1-6}$ alkyl.

Within this class is the subclass of the alternative embodiment wherein
R is methyl or ethyl;
$R_1$ is methyl or ethyl;
M is
  (a) $C_{1-3}$ alkyl, or
  (b) $C_{2-3}$ alkenyl;
$R_2$ is
  (a) hydrogen,
  (b) $C_{1-3}$ alkyl, or $C_{1-3}$ alkoxy, and
$R_3$ is hydrogen, or
$R_2$ and $R_3$ are joined together to form a furan or dioxacyclopentane ring;
$R'_4$ is hydroxy or chloro; and
$R_5$ is $C_{1-6}$ alkyl or hydrogen.

Illustrating this subclass is the compounds of Formula II

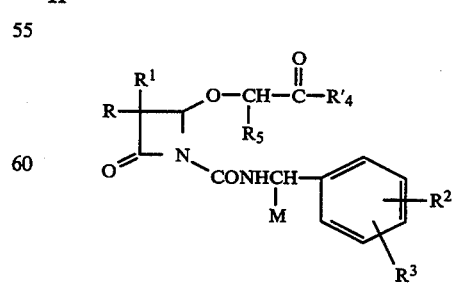

wherein
R is ethyl;
$R_1$ is ethyl;

M is
(a) propyl, or
(b) allyl;

R$_2$ is
(a) hydrogen,
(b) C$_{1-2}$ alkyl, or C$_{1-2}$ alkoxy, and

R$_3$ is hydrogen, or

R$_2$ and R$_3$ are joined together to form a furan or dioxacyclopentane ring;

R'$_4$ is hydroxy or chloro; and

R$_5$ is hydrogen, methyl or ethyl.

Exemplifying this subclass are the compounds of the group consisting of:
(a) 2-(S)-Carboxymethoxy-3,3-diethyl-N-[1-(R)-(4-methylphenyl)butyl]-4-oxo-1-azetidinecarboxamide and
(b) 2-(S)-Chlorocarbonylmethoxy-3,3-diethyl-N-[1-(R)-(4-methylphenyl) butyl]-4-oxo-1-azetidinecarboxamide.

Further exemplifying this subclass are the compounds from the group consisting of:
(a) 2-(S)-Carboxymethoxy-3,3-diethyl-N-[1-(R)-(benzofuran-5-yl)butyl]-4-oxo-1-azetidinecarboxamide and
(b) 2-(S)-Chlorocarbonylmethoxy-3,3-diethyl-N-[1-(R)-(benzofuran-5-yl)butyl]-4-oxo-1-azetidinecarboxamide;
(c) 2-(S)-Carboxymethoxy-3,3-diethyl-N-[1-(R)-(3,4-methylenedioxyphenyl)butyl]-4-oxo-1-azetidinecarboxamide; and
(d) 2-(S)-Chlorocarbaoylmethoxy-3,3-diethyl-N-[1-(R)-(3,4-methylenedioxyphenyl)butyl]-4-oxo-1-azetidinecarboxamide.

The compounds of the invention are prepared by known methods or are prepared among other methods by the following representative schemes. For example, methods for making such compounds are disclosed in EP 0 337 549, published Oct. 18, 1989, which is hereby incorporated by reference.

SCHEME 1

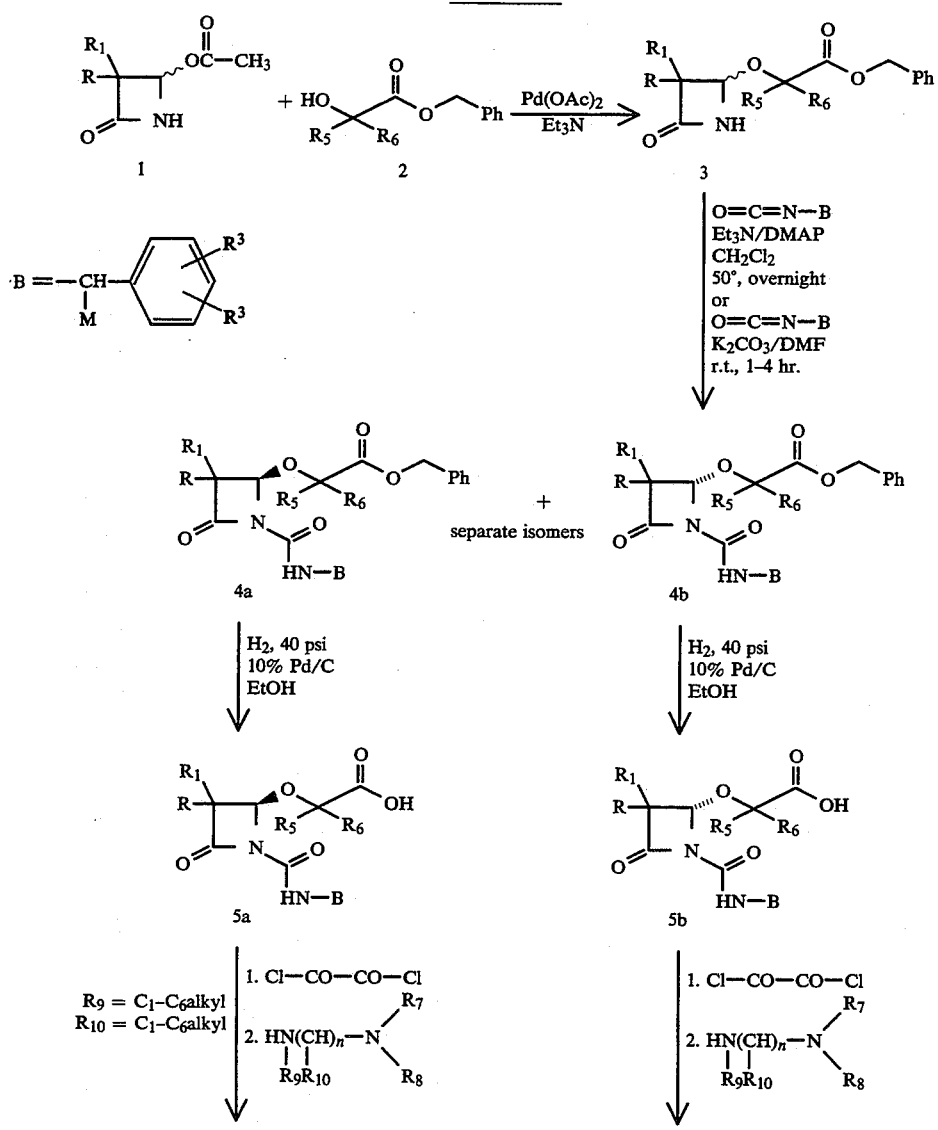

SCHEME 1
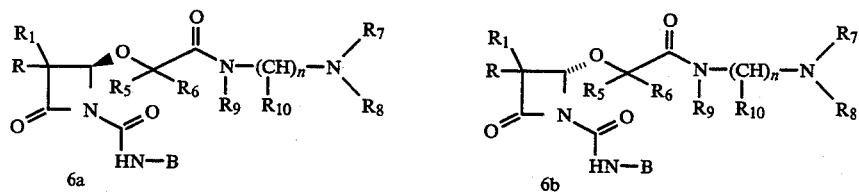
wherein n is 1 to 4.
SCHEME 2
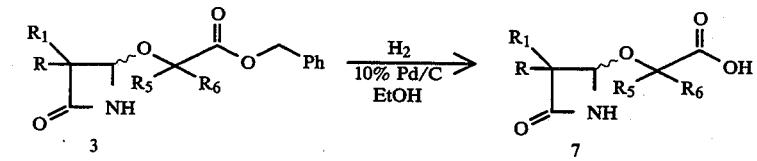
1. Resolve by fractional crystallization
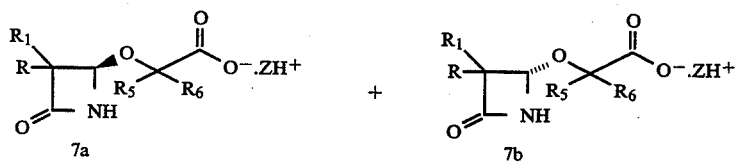
where Z is a chiral amine.
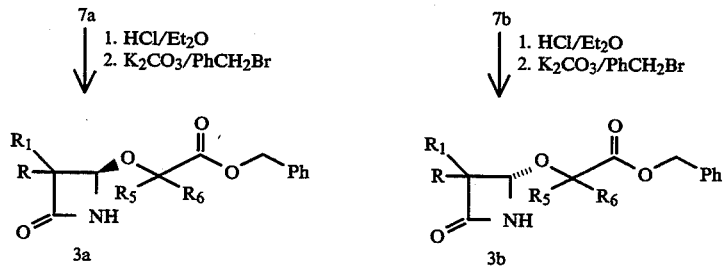
SCHEME 3
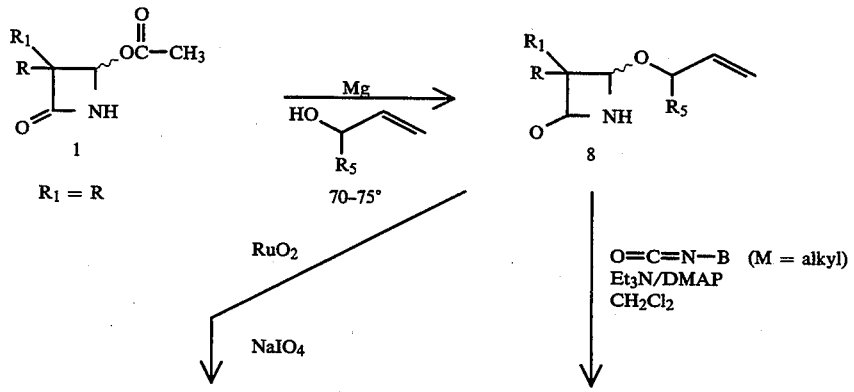

5,348,953
-continued
SCHEME 3
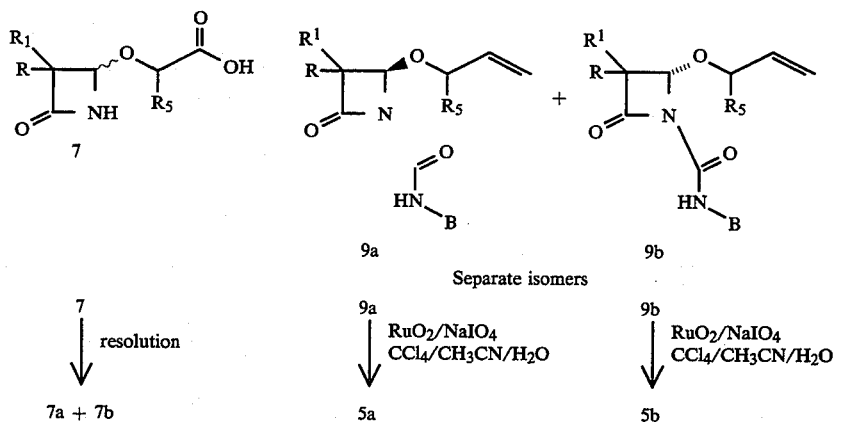
SCHEME 4
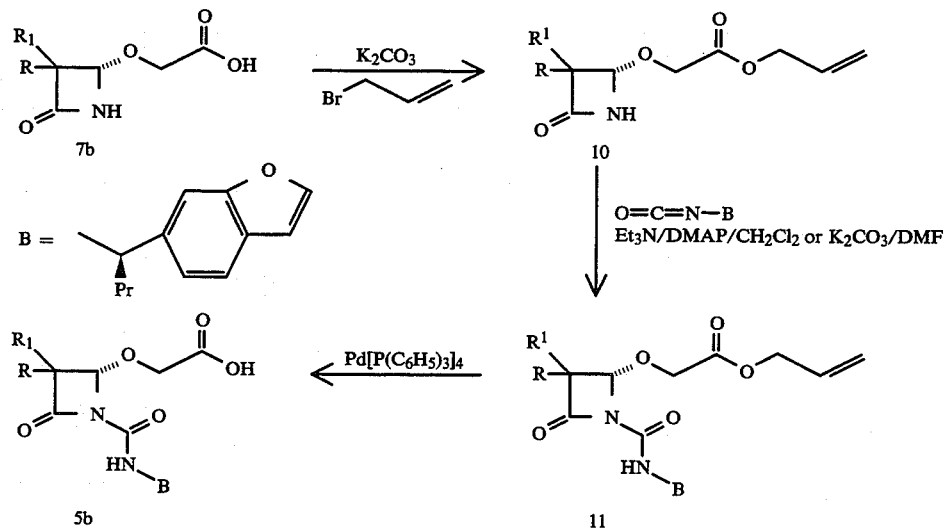
SCHEME 5
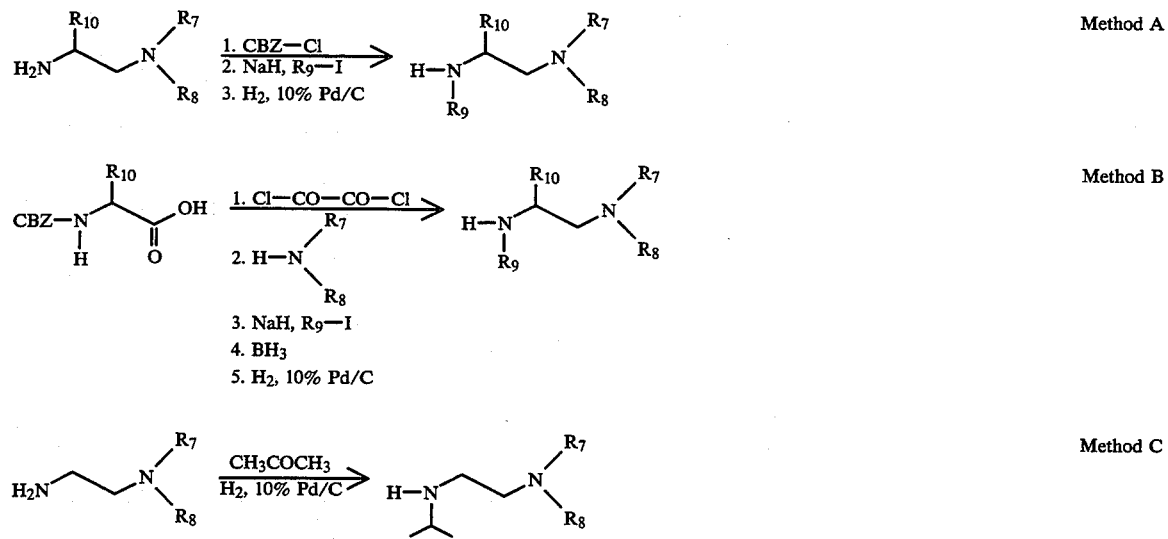
Method A
Method B
Method C

SCHEME 5
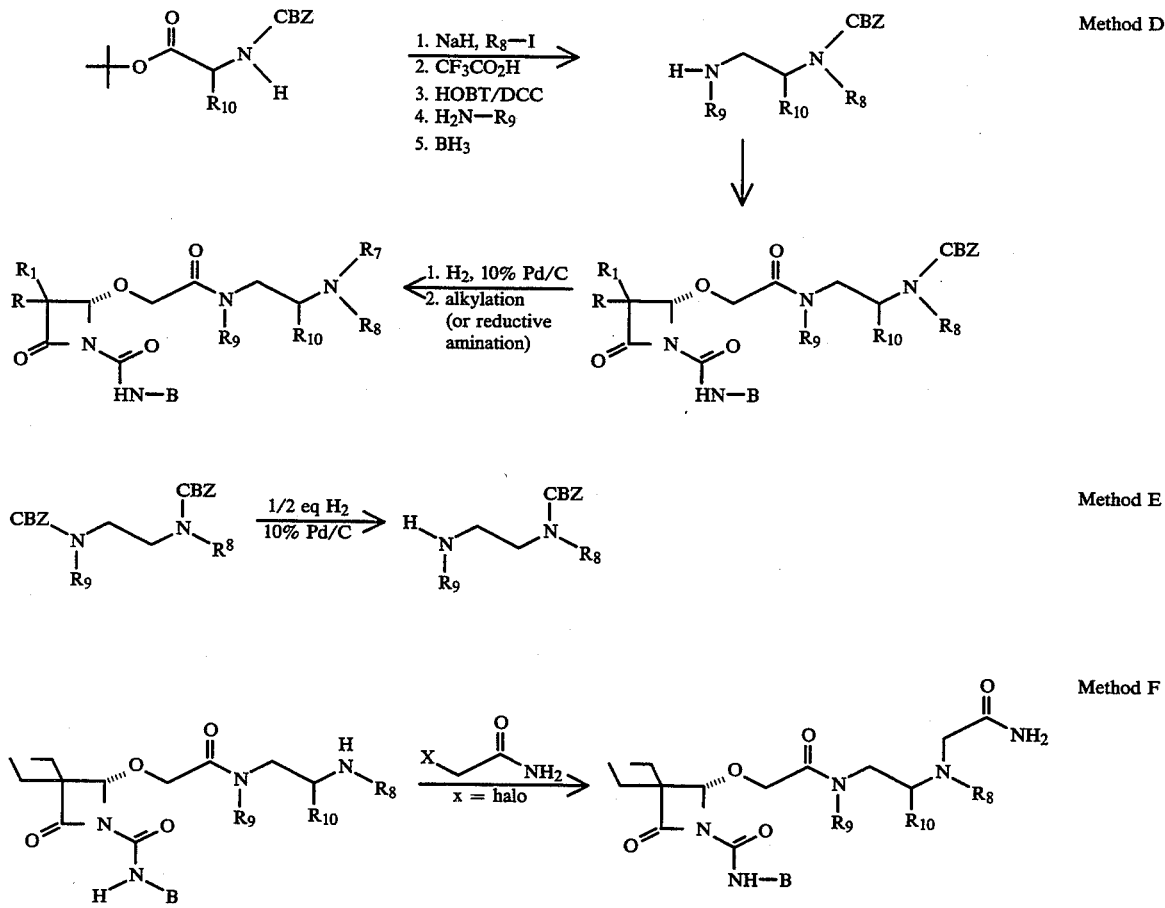
Method D
Method E
Method F
SCHEME 6
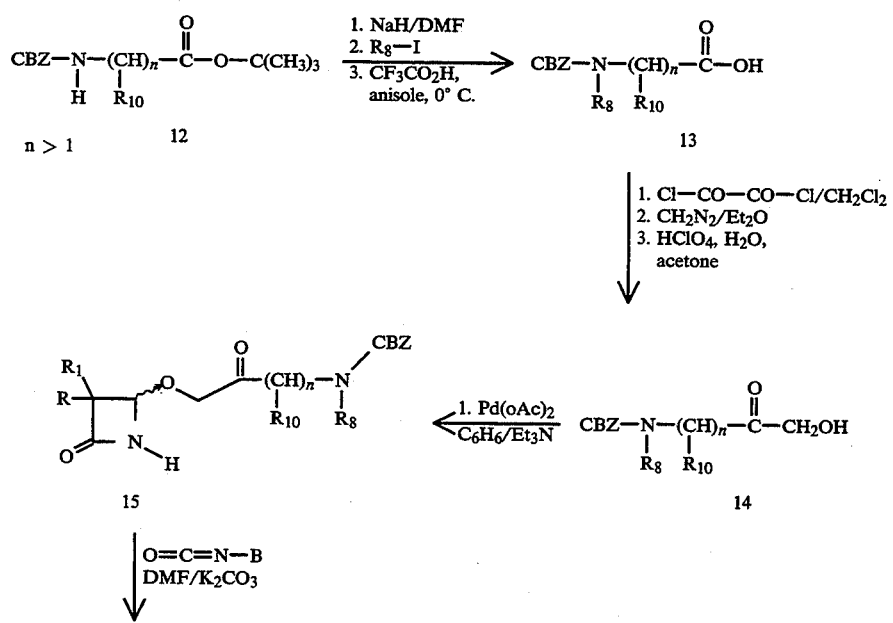

SCHEME 6 -continued

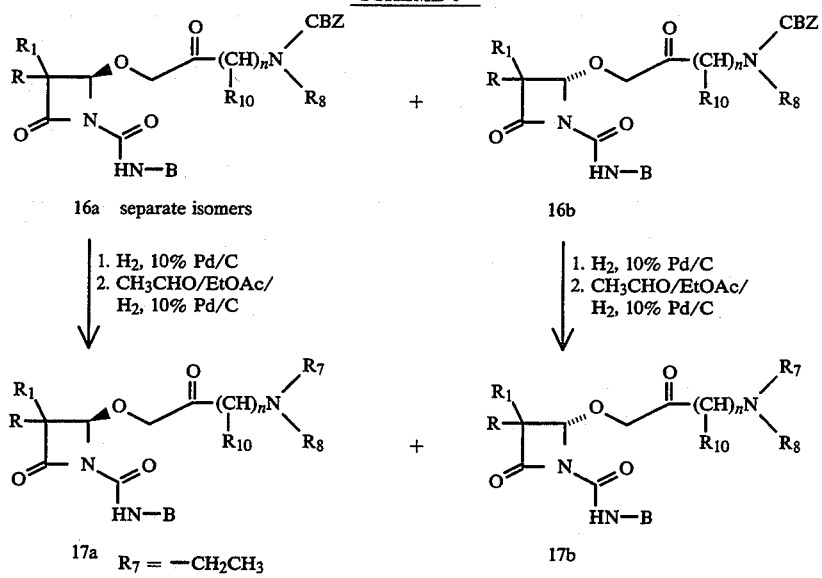

16a separate isomers      16b

1. H₂, 10% Pd/C
2. CH₃CHO/EtOAc/ H₂, 10% Pd/C

17a   $R_7 = -CH_2CH_3$      17b

The compounds of the present invention in which Y is a substituted amine (i.e. forming an amide bond) can be prepared by the general routes outlined in Schemes 1–5. Thus, the key intermediate acidic derivatives 5 can be prepared starting from the acyloxyazetidinone 1 and the benzyl ester of an appropriate hydroxyacid 2. The substituted azetidinone 3 so formed can then be reacted with an appropriate isocyanate to give the isomeric mixture 4a and 4b. When the isocyanate so used contains a chiral center (i.e. M not hydrogen) and is a single enantiomer, and when R=R₁ (or a single stereoisomer is present at C3 of the azetidinone), then the diastereomeric mixture 4a and 4b can be separated at this point, usually by chromatographic methods. Removal of the benzyl blocking group by catalytic hydrogenation gives the acid 5. The individual acids 5 can then be reacted with oxalyl chloride to give the corresponding acyl chlorides which can in turn be reacted with an appropriate amine to give the products 6. Depending upon the desired substitutions on the terminal amine, in some instances additional reactions may be needed to further functionalize the amino group (see Scheme 5, Method D and F).

In order to preclude the chromatographic separation of the diastereomers 4a and 4b (when R=R₁), an alternative route which utilizes the preparation of the individual enantiomers of 3 (R=R₁) is shown in Scheme 2. Thus, racemic 3 is first deblocked by catalytic hydrogenation and the racemic free acid 7 can be fractionally crystallized and separated into the individual enantiomers 7a and 7b as the appropriate α-methylbenzylamine salt. Acidification of the separated enantiomers and formation of the individual benzyl esters in the usual fashion, gives rise to the individual enantiomers 3a and 3b which can now be utilized in place of the racemate in the reactions shown in Scheme 1.

An alternative route to the key intermediates 5a and 5b are shown in Scheme 3. Thus, the acyloxyazetidinone 1 is treated with allyl alcohol at 70°–75° C. in the presence of magnesium to give the allyl ether 8. As before, this can be reacted with the appropriate isocyanate (M not allyl) to give the isomeric mixture 9a and 9b. As in Scheme 1, when the isocyanate so used contains a chiral center (i.e. M not hydrogen) and is a single enantiomer, and when R=R₁ (or a single stereoisomer is present at C3 of the azetidinone), then the diastereomeric mixture 9a and 9b can be separated at this point and the individual isomers can then be oxidized with RuO₂/NaIO₄ to give 5a and 5b, respectively.

Also shown in Scheme 3 is an alternate route to resolved acids 7a and 7b. Thus, oxidation of the allyl ether 8 with RuO₂/NaIO₄ leads directly to the glycollic acid derivative 7 (R₅=R₆=H) which can be resolved by fractional crystallization as the appropriate α-methylbenzylamine salt as described in Scheme 2.

Depending on the exact nature of the functionalities present on B in the isocyanate utilized in the preparation of 5a and 5b, it may be appropriate in some instances to utilize a blocking group other than benzyl on the carboxylic acid moiety during the various transformations shown in Scheme 1. A particular instance is shown in Scheme 4 where B is the (R)-1-(benzofuran-5-yl)-butyl group. In this case, the catalytic hydrogenation step necessary for the removal of the benzyl ester blocking group during the conversion of 4 to 5 gives rise to concomitant reduction of the benzofuran ring to give a dihydrobenzofuran. Thus, as shown in Scheme 4, the allyl ester can be utilized in place of the benzyl ester. In this case the allyl group can be removed by treatment of 11 with palladium (O) tetrakis triphenylphospine to give 5b which can then be used in Scheme 1 as before.

The procedures necessary to prepare the amines utilized in Scheme 1 to prepare compounds such as 6 from 5 are readily accessible to one skilled in the art of organic synthesis and some representative preparations utilized in making the compounds of the present invention are shown in Scheme 5. In addition, Scheme 5, Methods D and F show examples of modifications of the terminal amine after incorporation onto the lactam moiety.

The compounds of the present invention in which Y is an ester can be prepared from acids 5a and 5b by treatment with oxalyl chloride or formation of their active esters and subsequent reaction with the appropriate amino alcohol.

The compounds of the present invention in which Y is a short chain $C_{2-4}$ alkyl can be prepared by the general route shown in Scheme 6. Thus, an appropriate aminoalkylcarboxylic acid 12, blocked on the amino group with the CBZ moiety and on the carboxylate with a t-butyl ester, can be alkylated on nitrogen by conventional means to introduce the $R_8$ functionality and then the ester is deblocked to give 13. This free acid can then be converted to an acyl chloride by conventional means and treated with diazomethane followed by hydrolysis to give the hydroxymethyl ketone 14. Reaction with the acyloxyazetidinone 1 gives the ketone derivative 15. This can be treated with the appropriate isocyanate to give 16 as an isomeric mixture. When the isocyanate so used contains a chiral center (i.e. M not hydrogen) and is a single enantiomer, and when $R=R_1$ (or a single stereoisomer is present at C3 of the azetidinone), then the diastereomeric mixture 16a and 16b can be separated at this point, usually by chromatographic methods. The CBZ group can then be removed from the individual isomers by catalytic hydrogenation and the $R_7$ group can be introduced, preferably by reductive amination, to provide the required 17.

This invention also relates to a method of treating inflammation in patients using a compound of Formula (I), particularly a preferred compound as the active constituent.

As illustrated by the results obtained for the compounds of Formula (A) as summarized in the following Tables, it has been found that the compounds of Formula (I) are effective inhibitors of the proteolytic function of human neutrophil elastase

TABLE 1

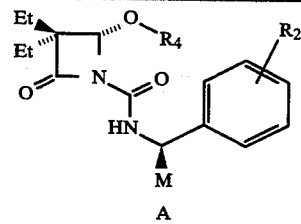

A wherein M is n-propyl; and $R_2$ is 4-methyl; and $R_4$ is $-CH(R_5)-CO-Y-N(R_7)R_8$

| Y | $R_5$ | $R_7$ | $R_8$ | $k_{obs}/[I]$ [$M^{-1}$, $Sec^{-1}$] |
|---|---|---|---|---|
| $-NHCH_2CH_2-$ | H | $-Et$ | $-Et$ | 220,000 |
| $-NHCH_2CH_2-$ | H | $-iPr$ | $-iPr$ | 105,000 |
| $-NHCH_2CH_2-$ | H | \multicolumn{2}{l|}{$-CH_2CH_2-O-CH_2CH_2-$} | 115,000 |
| $-NHCH_2CH_2-$ | H | $-Et$ | $-CH_2CH_2OMe$ |  |
| $-N(Me)CH_2CH_2-$ | H | $-Me$ | $-Me$ | 114,000 |
| $-N(Me)CH_2CH_2-$ | H | $-Et$ | $-Et$ | 150,000 |
| $-N(Me)CH_2CH_2-$ | H | $-iPr$ | $-iPr$ | 115,000 |
| $-N(Me)CH_2CH_2-$ | H | $-CH(CH_3)-(CH_2)_3-CH(CH_3)-$ | | 80,000 |
| $-N(Me)CH_2CH_2-$ | H | $-CH_2CH_2OMe$ | $-CH_2CH_2OMe$ | 165,000 |
| $-N(Me)CH_2CH_2-$ | H | $-Et$ | $-CH_2CH_2OMe$ | 110,000 |
| $-N(Me)CH_2CH_2-$ | H | $-iPr$ | $-CH_2CH_2OEt$ | 140,000 |
| $-N(Me)CH_2CH_2-$ | H | $-Me$ | $-iPr$ |  |
| $-N(Me)CH_2CH_2CH_2-$ | H | $-Me$ | $-Me$ | 115,000 |
| $-N(Et)CH_2CH_2-$ | H | $-Me$ | $-Me$ | 120,000 |
| $-N(Et)CH_2CH_2-$ | H | $-Et$ | $-Et$ | 177,000 |
| $-N(Et)CH_2CH_2-$ | H | $-iPr$ | $-iPr$ | 189,000 |
| $-N(Et)CH_2CH_2-$ | H | $-Me$ | $-CH_2CH_2OMe$ |  |
| $-N(Et)CH_2CH_2-$ | H | $-Et$ | $-CH_2CH_2OMe$ | 185,000 |
| $-N(Et)CH_2CH_2-$ | H | $-iPr$ | $-CH_2CH_2OEt$ | 195,000 |
| $-N(Et)CH_2CH_2-$ | H | $-CH_2CH_2-O-CH_2CH_2-$ | | 245,000 |
| $-N(Pr)CH_2CH_2-$ | H | $-iPr$ | $-CH_2CH_2OEt$ | 185,000 |
| $-N(Pr)CH_2CH_2-$ | H | $-Et$ | $-Et$ | 170,000 |
| $-N(Pr)CH_2CH_2-$ | H | $-Et$ | $-CH_2CH_2OMe$ |  |
| $-N(Pr)CH_2CH_2-$ | H | $-CH_2CH_2OMe$ | $-CH_2CH_2OMe$ |  |
| $-N(iPr)CH_2CH_2-$ | H | $-Me$ | $-Me$ | 175,000 |
| $-N(iPr)CH_2CH_2-$ | H | $-Et$ | $-Et$ | 175,000 |
| $-N(iPr)CH_2CH_2-$ | H | $-Et$ | $-CH_2CH_2OMe$ | 250,000 |
| $-N(iPr)CH_2CH_2-$ | H | $-iPr$ | $-iPr$ |  |
| $-NHCH_2CH_2-$ | Me | $-Me$ | $-Me$ | 1,036,000 |
| $-NHCH_2CH_2-$ | Me | $-Et$ | $-Et$ | 1,350,000 |
| $-NHCH_2CH_2-$ | Me | $-iPr$ | $-iPr$ | — |
| $-N(Me)CH_2CH_2-$ | Me | $-Me$ | $-Me$ | 1,650,000 |
| $-N(Me)CH_2CH_2-$ | Me | $-Et$ | $-Et$ | 1,800,000 |
| $-N(Et)CH_2CH_2-$ | Me | $-Me$ | $-Me$ | 1,770,000 |
| $-NHCH_2CH_2-$ | Me | $-CH_2CH_2-O-CH_2CH_2-$ | |  |
| co-valent bond | H | $-Et$ | $-Et$ | 315,000 |
| co-valent bond | H | $-H$ | $-H$ |  |
| co-valent bond | H | $-Me$ | $-Me$ | 125,000 |
| co-valent bond | H | $-CH_2CH_2-O-CH_2CH_2-$ | | 400,000 |

The following compounds are those of Formula A above wherein M is n-propyl; $R_2$ is 3,4-methylenedioxy; and $R_4$ is $CH(R_5)-C(O)-Y-N(R_7)R_8$

| Y | R$_5$ | R$_7$ | R$_8$ | $k_{obs}/[I]$ [M$^{-1}$.Sec$^{-1}$] |
|---|---|---|---|---|
| —N(Et)CH$_2$CH$_2$— | H | —Me | —Me | 425,000 |
| —N(Et)CH$_2$CH$_2$— | H | —CH$_2$CH$_2$—O—Me | | 450,000 |
| —N(iPr)CH$_2$CH$_2$— | H | —Me | —Me | 500,000 |

The following compounds are those of Formula A above wherein M is n-propyl; and R$_4$ is

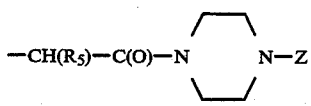

| R$_2$ | R$_5$ | Z | $k_{obs}/[I]$ [M$^{-1}$.Sec$^{-1}$] |
|---|---|---|---|
| -4-Me | H | cyclopropyl | 225,000 |
| -4-Me | H | —Me | 150,000 |
| -3,4-methylenedioxy- | H | cyclopropyl | 560,000 |
| -3,4-methylenedioxy- | H | —Me | 530,000 |
| -4-Me | H | H | 250,000 |
| -3,4-methylenedioxy- | H | H | 515,000 |
| -4-Me | H | CH$_2$CH$_2$OH | 300,000 |

Enzyme Assays for the Inhibition of Human Polymorphonuclear Leukocyte Elastase Via Hydrolysis of N-t-Boc-alanyl-alanyl-prolylalanine-p-nitroanilide (Boc-AAPAN) or N-t-Boc-alanyl-prolylvaline-p-nitroanilide (Boc-AAPVN) Reagent:

0.05M TES (N-tris[hydroxymethyl]methyl-2-aminoethanesulfonic acid) Buffer, pH 7.5.

0.2 mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

Results in Table I were reported as ID$_{50}$, effective dosage in micrograms per milliliter (μg/ml) for 50% inhibition of the enzyme activity 2 minutes after zero time.

Results were also expressed as Ki, the micromolar concentration of the inhibitor (μM) giving 50% of the control enzyme activity; or as $k$obs/I which is the second order rate constant in per mole per second for inactivation of the enzyme.

The elastase activity in the crude PMN extract may vary from one preparation to another. A control of each new batch is run, and the volume added in the assay procedure is adjusted according to activity.

TABLE 2

SECOND ORDER RATE CONSTANTS FOR THE INHIBITION OF HUMAN PROTEINASE 3

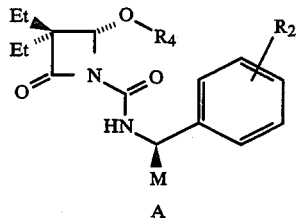

wherein M is n-propyl; and R$_2$ is 4-methyl;
and R$_4$ is —CH(R$_5$)—CO—Y—N(R$_7$)R$_8$

| Y | R$_5$ | R$_7$ | R$_8$ | SORC [M$^{-1}$, Sec$^{-1}$] |
|---|---|---|---|---|
| —N(Et)CH$_2$CH$_2$— | H | —Me | —Me | 7,900 |
| —N(Et)CH$_2$CH$_2$— | H | —Me | —CH$_2$CH$_2$OMe | 13,700 |
| —N(R$_8$)CH$_2$CH$_2$— | H | —Me | —CH$_2$CH$_2$ | 14,800 |

ASSAY

The PR3 catalyzed hydrolysis of MeO-Succ-AAPV-pNA was measured in a spectrophotometer monitoring absorbance at 410 n,m. The enzymatic activity was determined in 45 mM TES at pH 7.5, 450 mM NaCl and 10% DMSO. The data were fit by non-linear regression to equation 1 to obtain the initial rates. The nonlinear progress curves observed with time dependent inhibitors were fit to equation 2 to obtain the first order rate constant K$_{obs}$. Results were expressed as $k_{obs/I}$ which is the second order rate constant (SORC) in per mole per second for inactivation of the enzyme.

EQN 1 $Y = v_i X + B$

EQN 2 $Y = v_s{}^* X + [(v_o - v_s)(1 - e^{(-K_o{}^* X)})/K_o] + A_o$

Kinetic constants for the inhibition of PR3 catalyzed hydrolysis of 0.2 mM MoO-succ-AAPV-pNA were determined by varying the concentration of inhibitor present in the reaction vessel.

Accordingly, the compounds of Formula (I), can be used to reduce inflammation and/or relieve pain in diseases such as emphysema, rheumatoid arthritis, osteoarthritis, gout, bronchial inflammation, chronic or acute bronchitis, cystic fibrosis, adult respiratory, distress syndrome, atherosclerosis, sepsis, septicemia, shock, periodontitis, glomerular nephritis or nephosis, myocardial infarction, reperfusion injury, infectious arthritis, rheumatic fever and the like, and may reduce hemorrhage in acute promyelocytic leukemia and the like.

In this capacity, and as appreciated by those of skill in the art, therapy comprising administration of compounds of Formula I may actually include co-administration of one or more additional active agents. Classes of active agents include, but are not limited to β$_2$-adrenergic agonists; anti-cholinergic agents; steroids; nonsteroidal Anti-inflammatory agents (NSAID's); mucolytic agents; most all stabilizers; and antibacterials.

For purposes of this specification, $\beta_2$-adrenergic agonists are intended to include, but are not limited to, metaproterenol, terbutaline, isoetharine, albuterol, and ritodrine, carbuterol, fenoterol, quinterenol, rimiterol, salmefamol, soterenol, and tretoquinol.

For purposes of this specification, anticholinergic agents are intended to include, but are not limited to, attopine, and iptratropium-bromide.

For purposes of this specification, mucolytic agents are intened to include, but are not limited to acetylcysteine and guattenesin.

For purposes of this specification, steroids are intended to include, but are not limited to, prednisone, beclomethasone, budesonide, solumedrol, triamcinolone, and methyl-prednisolone.

For purposes of this specification most cell stabilizers are intended to include, but are not limited to cromolyn and ketotafin.

For purposes of this specification, nonsteroidal anti-inflammatory agents are intended to include, but are not limited to aspirin, diflunisal, naphthylsalicylate, phenylbutazolone, oxyphenbutazolone, indomethacin, sulindac, mefenamic acid, meclofenamate sodium, tolmetin, ibuprofen, naproxen, fenoprofen and piroxicam.

For the purposes of this specification, antibacterial agents are intended to include the broad classes of penicillins, cephalosporins and other beta-lactams, aminoglycosides, quinolones, macrolides, tetracyclines, sulfonamides, lincosamides and polymyxins. The penicillins, in turn, are intended to include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams are intended to include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxome, ceftizoxime, cetriaxone, cephoperazone, ceftazidime, imipenem and aztreonam. The aminoglycosides are intended to include, but are not limited to streptomycin, gentamicin, tobramycin, amikacin, netilmicin, kanamycin and neomycin. The quinolones are intended to include, but are not limited to nalidixic acid, norfloxacin, enoxacin, ciprofloxacin, ofloxacin, sparfloxacin and temafloxacin. The macrolides are intended to include, but are not limited to erythomycin, spiramycin and azithromycin. The tetracyclines are intended to include, but are not limited to doxycycline, minocycline and tetracycline. The sulfonamides are intended to include, but are not limited to sulfanilamide, sulfamethoxazole, sulfacetamide, sulfadiazine, sulfisoxazole and co-trimoxazole (trimethoprim/sulfamethoxazole). The lincosamides are intended to include, but are not limited to clindamycin and lincomycin. The polymyxins (polypeptides) are intended to include, but are not limited to polymyxin B and coilstin.

Alternatively, compounds of Formula I are useful in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocyte leukemia (FAB MS), erythroleukemia, chronic myelogenous leukemia, chronic myelomonocytic leukemia, chronic monocytic leukemia and conditions associated with leukemia involving activity of PMN neutral proteases e.g. disseminated intravascular coagulation.

Similarly, compounds of Formula I are useful for the inhibition of proteinase 3/myeloblastin, inhibition of elastase, inhibition of proliferation of leukemia cells, inducing differentiation of leukemia cells and remission of the disease state of leukemia.

Moreover, as described above, such treatment may optionally comprise the co-administration of an agent such as a compound selected from the group consisting of epsilon-aminocaproic acid, heparin, trasylol, prednisolone, cytosine arabinoside, b-mercaptopurine, cytarabine, an anthracycline and a vitamin A derivative.

For each of the uses, the compounds of Formula (I) and optional treatment agents, may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

For treatment as described above the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution glucose in water and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient(s) that may be combined with the carrier materials to produce a single dosage form will vary depending upon the host treated and the particular mode of administration. For example, a formulation intended for the oral administration of humans may contain from 5 mg to 2000 mg or 5000 mg of each active agent(s) compounded with an appropriate and convenient amount of carrier material which may vary from about 5 to about 95 percent of the total composition. For purposes of this specification, this broad dosage range is specifically intended to include, but is not limited to, range of 5 mg to 2000 mg; 25 mg to 2000 mg; 5 mg to 1000 mg; 25 mg to 1000 mg; 5 mg to 500 mg; and 25 mg to 500 mg. Dosage unit forms will generally contain between from about 25 mg to about 500 mg of active ingredient(s).

Furthermore, it is also possible that most effective treatment may warrent administration of an initial dosage of one range (e.g. 1–5 mg of active agent per kg of patient weight) followed by administration of a second range (e.g. 0.1 to 1 mg of active agent per kg of patient weight).

It will be understood., however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following example illustrates the preparation of the compounds useful in the method of treatment of the present invention, but does not limit the scope of the invention.

EXAMPLE 1

Benzyl glycolate

Into a solution of glycolic acid (35 gm, 46 mmol) in benzyl alcohol (200 mL) was bubbled anhydrous hydrogen chloride for 1 hr at 0° C. The reaction was then stirred for an additional 4 hrs at 0° C. before it was poured into a mixture of ice water and ether. The layers were separated and the aqueous layer was reextracted with ether. The ether layers were sequentially washed with sodium bicarbonate and brine, combined, dried over sodium sulfate and evaporated. Distillation of the residue at 103°–110° C. 0.5 mm afforded 59 gm (77%) of benzyl glycolate as a clear liquid.

EXAMPLE 2

(R,S)-2-(2-Benzyloxy-2-oxoethoxy)-3,3-diethylazetidin-4-one (3; $R=R_1=Et$, $R_5=R_6=H$)

Benzyl glycolate (16.6 gm, 0.1 mol) and (R,S)-2-acetoxy-3,3-diethyl-azetidin-4-one (1, 24.0 gm, 0.13 mol) were dissolved in benzene (150 mL) and Et$_3$N (21 mL, 0.15 mol) was added followed by Pd(OAc)$_2$ (1.0 gm). This mixture was stirred at room temperature for 20 hr when an additional 6.0 gm of 1 was added. After stirring for an additional 4 hr, the reaction was diluted with Et$_2$O and poured onto a mixture of ice-H$_2$O, 2N HCl (100 mL) and Et$_2$O. The layers were separated and the aqueous layer was further extracted with Et$_2$O. The pooled Et$_2$O layers were washed with brine, dried over Na$_2$SO$_4$, filtered and evaporated to dryness. The crude product so obtained was purified by LC (two portions) on silica gel using EtOAc/hexane (1:4 to 2:3) as eluent, to give 26 gm of the title compound suitable for use in the next step.

NMR (CDCl$_3$, δ from TMS): 0.92 (t, 3H, J=8 Hz), 0.96 (t, 3H, J=8 Hz), 1.5–1.9 (m, 4 H), 4.21 (ABq, 2 H, J=14 Hz) 4.69 (s, 1H), 5.16 (s, 2H), 6.45 (br. s, 1H), 7.33 (br. s, 5H).

EXAMPLE 3

(4S)-2-(2-Benzyloxy-2-oxoethoxy)-3,3-diethylazetid-4-one (3b; $R=R_1=Et$, $R_5=R_6=H$).

Step A: Preparation of 2-(S)-Carboxymethoxy-3,3-diethyl-azetidin-4-one, (R)-α-methylbenzylamine salt (7b; $R=R_1=Et$, $R_5=R_6=H$, $Z=(R)$-α-methylbenzylamine)

(R,S)-2-(2-Benzyloxy-2-oxoethoxy)-3,3-diethyl-azetidin-4-one (56 gm, 0.19 mol) prepared as described in Example 2 was dissolved in ethanol (400 mL) and hydrogenated over 10% palladium on carbon (5.0 gm) at 40 psi for 2 hrs. The reaction was filtered and evaporated. The crude acid was dissolved in ethyl acetate (1000 mL) and warmed to 70° C. while a solution of (R)-α-methylbenzylamine (11.0 gm, 0.09 mol, 0.5 eq) in ethyl acetate (100 mL) was slowly added. The solution was aged at rt overnight to allow crystallization and was then filtered and washed with ethyl acetate and air dried to give 22.2 gm of material which is enriched in the desired (4S) isomer. [α]$_D$ (EtOH, c=0.56)=+4.5. This (4S) enriched material could be used directly or further enriched by recrystallization from n-propanol or treated as below.

A portion of the above salt (16 gm, 0.050 mol) was dissolved in ice water containing 50 mL of 2N HCl and was extracted with 4×100 mL of ethyl acetate. Each ethyl acetate layer was consecutively washed with a portion of brine, then combined, dried over sodium sulfate and evaporated to an oil. This oil was taken up in hot ethyl acetate (400 mL) and (R)-α-methylbenzylamine (2.5 gm, 0.02 mol, 0.4 eq) added. The solution was seeded and then aged at rt for 4 hrs before the Solid was filtered, washed with ethyl acetate and air dried to afford 4.7 gm of the title compound having [α]$_D$ (EtOH)=−12. A second crop was mostly the (4R) isomer, [α]$_D$ (EtOH)=+22.

A second batch of pure material (4.0 gm) was obtained by extraction of the free acid as above from the combined mother liquors, using (S)-α-methylbenzylamine to remove most of the (4R) isomer and repeating the above extraction and crystallization process. The combined yield of available title compound as the (4S) salt was then 34%.

Step B: Preparation of (4S)-2-(2-Benzyloxy-2-oxoethoxy)-3,3-diethyl-azetidin-4-one (3b; $R=R_1=Et$, $R_5=R_6=H$)

Using the acidification/extraction process described above in Example 3, Step A, 8.3 gm of (4S) 2-((3,3-diethyl-4-oxo-2-azetidinyl)oxy)acetic acid, (R)-α-methylbenzylamine was converted to 5.2 gm (100%) of the free acid, [α]$_D$ (EtOH, c=1.5)=−31. To a solution of this free acid (4.2 gm, 0.021 mol) and benzyl bromide (5.4 gm, 0.031 mol) in DMF (50 mL) was added powdered potassium carbonate (4.3 gm, 0.042 mol).

The mixture was stirred at rt for 5 hrs and was then poured into ice water and extracted with two portions of ether. The ether layers were washed with brine, combined, dried over sodium sulfate and evaporated. Flash chromatography (20–40% ethyl acetate/hexanes) afforded 6.0 gm (98%) of the title compound. [α]$_D$ (EtOH, c=2.43)=−30.

EXAMPLE 4

2-(R)-[2-Benzyloxy-1-((S)-methyl)-2-oxoethoxy]-3,3-diethyl-azetidin-4-one (3; $R=R_1=Et$, $R_5=H$, $R_6=Me$)
and
2-(S)-[2-Benzyloxy-1-((S)-methyl)-2-oxoethoxy]-3,3-diethyl-azetidin-4-one (3; $R=R_1=Et$, $R_5=H$, $R_6=Me$)

(S)-Benzyl lactate (4.9 gm, 27 mmol) and (R,S)-2-acetoxy-3,3-diethyl-azetidin-4-one (7.0 gm, 38 mmol) were dissolved in benzene (25 mL) and Et$_3$N (3.8 mL, 27 mmol) was added followed by Pd(OAc)$_2$ (0.600 gm). This mixture was stirred at room temperature for 6 hr and then diluted with Et$_2$O. This solution was washed successively with 2N HCl and brine and then dried over Na$_2$SO$_4$, filtered and evaporated to dryness. The crude products so obtained were purified by LC on silica gel using EtOAc/hexane (3:7) as eluent to give first an isomeric mixture of the (2R) and (2S) products, and then 5.0 gm of pure (2S) title compound were obtained as an oil suitable for use in the next step. The mixed fractions could then be separated by rechromatography on thick layer silica plates.

Main product (2S), lower Rf isomer:
NMR (CDCl$_3$, δ from TMS): 0.92 (t, 3H, J=8 Hz), 1.00 (t, 3H, J=8 Hz), 1.49 (d, 3H, J=8 Hz), 1.5–1.9 (m, 4H), 4.14 (q, 1 H, J=8 Hz), 4.64 (s, 1H), 5.19 (ABq, 2H, J=12 Hz), 6.24 (br, s, 1H), 7.38 (br s, 5H). Minor product (2R), higher Rf isomer on TLC:

NMR (CDCl$_3$, δ from TMS): 0.89 (t, 3H, J=8 Hz), 1.0 (t, 3H, J=8 Hz), 1.46 (d, 2H, J=8 Hz), 1.5–1.9 (m, 4H), 4.18 (q, 2H, 8 Hz), 4.80 (s, 1H), 5.18 (ABq, 2H, 12 Hz), 6.35 (br s, 1H), 7.38 (br s, 5H).

EXAMPLE 5

2-(S)-(2-Benzyloxy-2-oxoethoxy)-3,3 1diethyl-N-[1-(R)-(4-methylphenyl)but-3-enyl]-4-oxo-1-azetidinecarboxamide (4b; $R=R_1=Et$, $R_5=R_6=H$, $M=$allyl, $R_2=H$, $R_3=4$-Me)

Method A:

The material prepared above in Example 2 (29 gm, 0.1 mol) and (R)-α-allyl-4-methylbenzyl isocyanate (see EPO 337 549, 22.4 gm, 0.12 mol) were dissolved in $CH_2Cl_2$ (100 mL) and $Et_3N$ (21 mL, 0.15 mol) and DMAP (1.0 gm) were added. The reaction was stirred at 45° C. overnight under nitrogen and then was poured into a mixture of 2N HCl and ice-$H_2O$. The mixture was extracted with $CH_2Cl_2$ (twice) and the pooled organic layers were washed with brine, dried over $Na_2SO_4$, filtered and evaporated to dryness. This crude product mixture of diastereomers was purified by LC on silica gel (two portions) using $EtOAc/CH_2Cl_2$/hexane (4–5:5:90) and 12.9 gm of the required high Rf isomer. (2S) was isolated and used in the next step.

NMR ($CDCl_3$, δ from TMS): 0.93 (t, 3H, J=8 Hz), 1.03 (t, 3H, J=8 Hz), 1.5–1.9 (m, 4H), 2.31 (s, 3H), 2.55 (t, 2H, 7 Hz), 4.64 (ABq, 2H, 18 Hz), 4.88 (q, 1H, J=8 Hz), 5.11 (s, 1H), 5.05–5.25 (m, 2H), 5.6–5.8 (m, 1H), 7.04 (br d, 1H, 8 Hz), 7.14 (br s, 4H), 7.38 (br s, 5H).

Method B:

The material prepared above in Example 2 (26.8 gm, 0.092 mol) was dissolved in DMF (70 mL) and ground $K_2CO_3$ (2.8 gm) was added followed by (R)-α-allyl-4-methylbenzyl isocyanate (21 gm, 0.11 mol), rinsing in with 22 mL of DMF. The reaction mixture was stirred at room temperature under nitrogen for 30 min and then was quenched with $H_2O$. This mixture was extracted with $Et_2O$ (three times) and the pooled organic layers were successively washed with $H_2O$ and brine before being dried over $Na_2SO_4$, filtered and evaporated to dryness to give 45 gm of the diastereomeric mixture. This was separated by preparative LC using a silica gel column using $EtOAc/CH_2Cl_2$/hexane (5:5:90) as eluent and the title compound, higher Rf isomer (2S) was obtained (13 gm) as well as the lower Rf isomer (2R) (22.6 gm). The title compound was identical in all respects to material prepared as described above in Method A.

Method C:

Starting with material prepared as described above in Example 3 ([α]$_D$= −30) (4.0 gm) and using the methods described above in Example 5, Method A, 6.0 gm (91%) of the desired isomer title compound were obtained. This material was identical in all respects to material prepared as described above in Methods A and B.

EXAMPLE 6

2-(S)-(2-Benzyloxy-1-((S)-methyl)2-oxoethoxy)-3,3-diethyl-N-[1-(R)-(4-methylphenyl)but-3-enyl]-4-oxo-1-azetidinecarboxamide(4b; $R=R_1$=Et, $R_5$=H, $R_6$=Me, M=allyl, $R_2$=H, $R_3$=4-Me)

The lower Rf material prepared above in Example 4 (200 mg, 0.66 mmol) and (R)-α-allyl-4-methylbenzyl isocyanate (185 mg, 1.0 mmol) were dissolved in $CH_2Cl_2$ (2 mL) and $Et_3N$ (0.15 mL) and a trace of DMAP were added. The reaction was stirred at 40° C. for 16 hr under nitrogen and then was poured into a mixture of 2N HCl and ice-$H_2O$. The mixture was extracted with $CH_2Cl_2$ (twice) and the pooled organic layers were washed with brine, dried over $Na_2SO_4$, filtered and evaporated to dryness. This crude product mixture was purified by preparative thick layer chromatography on silica gel plates developed with EtOAc/hexane (1:9) to give 160 mg of the title compound as a clear oil suitable for use in the next step.

NMR ($CDCl_3$, δ from TMS): 0.88 (t, 3H, J=8 Hz), 1.01 (t, 3H, 8 Hz), 1.44 (d, 3H, J=8 Hz), 1.5–1.9 (m, 4H), 2.32 (s, 3H), 2.56 (t, 2H, J=7 Hz ), 4.88 (q, 1H, J=7 Hz ), 4.94 (q, 1H, J=8 Hz), 5.07 (s, 1H), 5.0–5.3 (m, 2H), 5:6–5.8 (m, 1H), 7.04 (br d, 1H, J=8 Hz), 7.14 (br s, 4H), 7.32 (br s, 5H).

EXAMPLE 7

2-(S)-Carboxymethoxy-3,3-diethyl-N-[1-(R)-(4-methylphenyl)butyl]-4-oxo-1-azetidinecarboxamide (5b; $R=R_1$=Et, $R_5=R_6$=H, M=Pr, $R_2$=H, $R_3$=4-Me)

The high Rf material prepared above in Example 5, Methods A, B or C (12.9 gm) was dissolved in EtOH (50 mL) and 10% Pd on carbon (600 mg) was added. This mixture was hydrogenated at 40 p.s.i. for 3 hr and then was filtered through Celite and the filtrate was evaporated to dryness to give 10.0 gm of the title compound as an oil suitable for use in the next step.

NMR ($CDCl_3$, δ from TMS): 0.94 (t, 3H, J=8 Hz), 0.96 (t,3H, J=8 Hz), 1.05 (t, 3H, J=8 Hz), 1.1–1.4 (m, 2H), 1.5–2.0 (m, 6H), 2.34 (s, 3H), 4.55 (ABq, 2H, J=18 Hz), 4.81 (q, 1H, J=8 Hz), 5.06 (s, 1H), 6.93 (br d, 1H, J=8 Hz), 7.16 (br s, 4H).

EXAMPLE 8

2-(S)-(1-(S)-Carboxyethoxy)-3,3-diethyl-N-[1-(R)-(4-methylphenyl)butyl]-4-oxo-1-azetidinecarboxamide (5b; $R=R_1$=Et, $R_5$=H, $R_6$=Me, M=Pr, $R_2$=H, $R_3$=4-Me)

The material prepared above in Example 6 (0.16 gm) was dissolved in EtOH (50 mL) and 10% Pd on carbon (10 mg) was added. This mixture was hydrogenated at 40 p.s.i. for 2 hr and then was filtered through Celite and the filtrate was evaporated to dryness and then purified on thick layer silica plates developed with EtOAc/hexane/AcOH (30:70: 1)to give 0.085 gm of the title compound as an oil suitable for use in the next step.

NMR ($CDCl_3$, δ from TMS): 0.92 (br t, 6H, J=8 Hz), 1.04 (t, 3H, J=8 Hz), 1.2–1.45.(m, 2H), 1.46 (d, 3H, J=8 Hz), 1.6–2.0 (m, 6H), 2.31 (s, 3H), 4.78 (q, 1H, 8 Hz), 4.95 (q, 1H, J=8 Hz),. 5.11 (s, 1H), 7.0 (br d, 1H, 8 Hz), 7.13 (br s, 4H).

EXAMPLE 9

2-(S)-[2-[[2-(Dimethylamino)ethyl]ethylamino]-2-oxoethoxy]-3,3-diethyl-N-[1-(R)-(4-methylphenyl)butyl]-4-oxo-1-azetidinecarboxamide (6b; $R=R_1$=Et, $R_5=R_6$=H, M=Pr, $R_2$=H, $R_3$=4-Me, $R_9$=Et, $R_{10}$=H, $R_7=R_8$=Me, n=2)

A solution of the material prepared as described above in Example 7 (10.0 gm, 0.026 mol) in methylene chloride (100 mL) containing 2 drops of dimethylformamide was cooled in an ice bath and oxalyl chloride (2.5 mL, 0.028 mol) was slowly added. The ice bath was then removed and the reaction was stirred at rt for 1 hr and then evaporated in vacuo to remove HCl and excess oxalyl chloride. The residue was again taken up in methylene chloride (100 mL) and added over 10 min to a cold solution of N,N-dimethyl-N'-ethylethylenediamine (4.5 gm, 0.039 mol) and triethylamine (5.5 mL, 0.039 mol) in methylene chloride (100 mL) while cooled in an ice bath. The reaction was stirred a further 1 hr and then poured into ice water and extracted twice with methylene chloride. The methylene chloride layers were washed with brine, combined, dried over sodium sulfate and evaporated. The residue was purified by flash chromatography eluting first with ethyl acetate and then 2% triethylamine/10% methanol/88% ethyl acetate to give 10.1 gm (81%) of the title compound as an oil.

NMR (CDCl₃ δ from TMS): 0.9–1.2 (m, 12H), 1.2–1.4 (m, 2H), 1.6–2.0 (m, 6H), 2.28 (s, 3H), 2.36 (s, 6H), 2.3–2.6 (m, 2H), 3.1–3.5 (m, 4H), 4.69 (ABq, 2H, J=16 Hz), 4.78 (q, 1H, J=8 Hz), 5.10 and 5.13 (2 s, 1H), 7.04 (br d, 1H, J=8 HZ), 7.13 (br s, 4H).

EXAMPLE 10

2-(S)-[2-[[2-(Dimethylamino)ethyl]ethylamino]-2-oxoethoxy]-3,3-diethyl-N-[1-(R)-(4-methylphenyl)butyl]-4-oxo-1-azetidinecarboxamide, L-malic acid salt (6b, malic acid salt; $R=R_1=Et$, $R_5=R_6=H$, $M=Pr$, $R_2=H$, $R_3=4$-Me, $R_9=Et$, $R_{10}=H$, $R_7=R_8=Me$, n=2)

To a solution of L-malic acid (5.0 gm, 0.037 mol) in ethyl acetate (300 mL) was added the material prepared as described above in Example 9 (17 gm, 0.035 mol) in ethyl acetate (100 mL). The solution was seeded and stirred at rt for 1 hr at which time the salt began to precipitate. The volume was reduced in vacuo at 30° C. to a thick slurry and then diluted with ethyl acetate to 100 mL final volume. To the rapidly stirred slurry was then slowly added 300 mL of ether and after aging a further 30 min the precipitate was filtered, washed with 10% ethyl acetate/ether, then ether and air dried to afford 17.69 gm of the title compound as a white solid, mp 109°–110.5° C.

EXAMPLE 11

2-(S)-[2-[[2-((2-Methoxyethyl)-methylamino)ethyl]ethylamino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=4$-Me, $R_9=Et$, $R_{10}=H$, $R_7=Me$, $R_8=CH_2CH_2OMe$, n=2)

A solution of the material prepared as described above in Example 7 (8.0 gm, 0.021 mol) in methylene chloride (50 mL) containing a trace of dimethylformamide was cooled in an ice bath and oxalyl chloride (2.2 mL, 0.025 mol) was slowly added in two equal portions. The ice bath was then removed and the reaction was stirred at rt for 1.5 hr and then evaporated in vacuo to remove HCl and excess oxalyl chloride. The residue was then dissolved in methylene chloride (50 mL) and cooled to 0° C. To this solution was added, over 5 min, a cold solution (in two equal portions) of N-methyl-N-(2-methoxyethyl)-N'-ethylethylenediamine (5.0 gm, 0.030 mol, prepared as described in Example 14a) and triethylamine (3.0 gm, 0.030 mol) in methylene chloride (50 mL) while cooled in an ice bath. The reaction was stirred a further 1 hr and then poured into ice water and extracted twice with methylene chloride. The methylene chloride layers were washed with brine, combined, dried over sodium sulfate and evaporated. The residue was purified by flash chromatography eluting first with ethyl acetate and then 2% triethylamine/10% methanol/88% ethyl acetate to give 8.07 gm of the title compound.

NMR (CDCl₃ δ from TMS): 0.9–1.1 (m, 12H), 1.2–1.4 (m, 2H), 1.6–2.0 (m, 6H), 2.32 (s, 6H), 2.5–2.7 (m, 4H), 3.1–3.5 (m, 4H), 3.33 and 3.34 (2 s, 3H), 3.46 (t, 2H, J=6 Hz), 4.66 (ABq, 2H, J=16 Hz), 4.78 (m, 1H), 5.10 and 5.13 (2 s, 1H), 7.02 (m, 1H), 7.14 (br s, 4H).

EXAMPLE 12

2-(S)-[2-[[2-(Diethylamino)ethyl]methylamino]-2oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=4$-Me, $R_9=Me$, $R_{10}=H$, $R_7=R_8=Et$, n=2)

A solution of the material prepared in Example 7 (0.28 gm, 0.72 mmol) in CH₂Cl₂ (3 mL) was cooled to 0° C. and a few drops of dimethylformamide (DMF) were added. Oxalyl chloride (0.125 mL) was then added and the solution was allowed to warm up to room temperature under nitrogen. After 30 min the mixture was evaporated to dryness and the residue was redissolved in CH₂Cl₂ (3 mL). N,N-Diethylamino-N'-methylethylenediamine (0.28 gm) was added and the reaction was stirred at room temperature for 2 hr. CH₂Cl₂ (100 mL) was then added and the solution was washed successively with aqueous K₂CO₃ (50 mL) and brine (50 mL) before being dried over Na₂SO₄, filtered and evaporated to dryness. The crude product so obtained was purified by chromatography on silica gel using MeOH-/EtOAc (1:9) as eluent to afford 200 mg of the title compound.

NMR (CDCl₃; δ from TMS): 0.95–1.2 (m, 15H), 1.2–1.5 (m, 2H), 1.6–2.0 (m, 6H), 2.32 (s, 3H), 2.52 (q, 4H, J=8 Hz), 2.5–2.7 (m, 2H), 2.93 (s, 3H), 3.1–3.5 (m, 2H), 4.62 and 4.71 (2 ABq, 2H, J=16), 4.80 (q, 1H, J=8 Hz), 5.09 and 5.13 (2 s, 1H), 7.01 and 7.04 (2 br d, J=8 Hz), 7.14 (br s, 4H).

Following substantially the same procedure as described in Example 12, but using an appropriately substituted diamine, compounds (a)–(x) were prepared:

(a)  2-(S)-[2-[[2-(Diethylamino)ethyl]amino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=4$-Me, $R_9=R_{10}=H$, $R_7=R_8=Et$, n=2)

NMR (CDCl₃; δ from TMS): 0.9–1.1 (m, 15H), 1.1–1.4 (m, 2H), 1.5–2.0 (m, 6H), 2.31 (s, 3H), 2.4–2.7 (m, 6H), 3.2–3.5 (m, 2H ), 4.30 (ABq, 2H, J=16 Hz), 4.78 (q, 1H, J=8 Hz ), 5.01 (s, 1H), 6.88 (br 2, 1H, J=8 Hz), 7.13 (br s, 4H), 7.50 (v br s, 1H).

(b) 2-(S)-[2-[[2-(Diisopropylamino)ethyl]amino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=4$-Me, $R_9=R_{10}=H$, $R_7=R_8=iPr$, n=2)

NMR (CDCl₃ δ from TMS): 0.85–1.1 (m, 21H), 1.1–1.4 (m, 2H), 1.5–2.0 (m, 6H), 2.32 (s, 3H), 2.5–2.65 (m, 2H), 2.9–3.1 (m, 2H), 3.2–3.35 (m, 2H), 4.32 (ABq, 2H, J=16 Hz), 4.79 (q, 1H, J=8 Hz), 4.96 (s, 1H), 6.78 (br d, 1H, J=4 Hz), 7.14 (br s, 8H), 7.36 (v br s, 1H).

(c) 2-(S)-[2-[[2-(morpholin-1-yl)ethyl]amino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=4$-Me, $R_9=R_{10}=H$, $R_7$ and $R_8$ joined together form morpholine moiety, n=2)

NMR (CDCl₃; δ from TMS): 0.93 (t, 3H, J=8 Hz), 0.95 (t, 3H, J=8 Hz), 1.08 (t, 3H, J=8 Hz), 1.2–1.4 (m, 2H), 1.6–2.0 (m, 6H), 2.32 (s, 3H), 2.4–2.6 (m, 4H), 3.43 (ABq, 2H, J=6 Hz), 3.68 (t, 4H, J=6 Hz), 4.24 (ABq, 2H, J=16 Hz), 4.78 (q, 1H, J=8 Hz), 4.98 (s, 1H, 6.90 (br d, 1H, J=8 Hz), 7.14 (br s, 4H), 7.47 (v. br t, 1H, J=4 Hz).

(d) 2-(S)-[2-[[2-((2-Methoxyethyl)methylamino)ethyl]amino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=$R_{10}$=H, $R_7$=Et, $R_8$=$CH_2CH_2OMe$, n=2)

NMR ($CDCl_3$; δ from TMS): 0.9–1.1 (m, 12H), 1.2–1.4 (m, 2H), 1.5–2.0 (m, 6H), 2.32 (s, 3H), 2.4–2.9 (m, 6H), 3.32 (s, 3H), 3.2–3.6 (m, 4H), 4.30 (ABq, 2H, J=16 Hz), 4.78 (q, 1H, J=8 Hz), 5.08 and 5.14 (2 s, 1H), 6.92 and 7.03 (2 br d, J=8 Hz, 1H), 7.14 (br s, 4H)

(e) 2-(S)-[2-[[2-(Dimethylamino)ethyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$=H, $R_7$=$R_8$=Me, n=2)

NMR ($CDCl_3$; δ from TMS): 0.92 (t, 3H, J=8 Hz), 0.96 (t, 3H, J=8 Hz), 1.06 (t, 3H, J=8 Hz), 1.1–1.4 (m, 2H), 1.5–2.0 (m, 6H), 2.32 (s, 3H), 2.29 and 2.36 (2 s, 3H), 2.44 (br s, 3H), 2.5–2.7 (m, 2H), 2.94 and 2.97 (2 s, 3H), 3.1–3.6 (m, 2H), 4.68 (ABq, 2H, J=18 Hz), 4.78 (q, 1H, J=8 Hz), 5.12 (br s, 1H), 7.04 (br d, 1H, J=8 Hz), 7.14 (br s, 4H).

(f) 2-(S)-[2-[[2-(Diisopropylamino)ethyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$=H, $R_7$=$R_8$=iPr, n=2)

NMR ($CDCl_3$; δ from TMS): 0.8–1.1 (m, 21H), 1.1–1.4 (m, 2H), 1.5–2.0 (m, 6H), 2.32 (s, 3H), 2.3–2.6 (m, 2H), 2.8–3.4 (m, 7H) 4.60 and 4.80 (2 ABq, 2H, J=16 Hz), 4.78 (q, 1H, J=8 Hz), 5.08 and 5.16 (2 s, 1H), 7.00 and 7.04 (2 br d, J=8 Hz, 1H), 7.14 (br s, 4H).

(g) 2-(S)-[2-[[2-(2,6-dimethylpiperidin-1-yl)ethyl]methylamino]-2-oxoethoxy]-3,3-diethyl-N-[1-(R)-(4-methylphenyl)butyl] -4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$H, $R_7$ and $R_8$ joined together form 2,6-dimethyeridine moiety, n=2)

NMR ($CDCl_3$; δ from TMS ): 0.8–1.5 (m, 2H), 1.5–2.0 (m, 8H), 2.32 (s, 3H), 2.4–2.6 (m, 2H), 2.6–3.0 (m, 2H), 2.92 (br s, 3H), 3.1–3.4 (2m, 2H), 4.60 and 4.80 (2 ABq, 2H, J=16 Hz), 4.78 ( q, 1H, J=8 Hz), 5.08 and 5.16 ( 2 b r s, 1H), 7.00 and 7.04 (2 br d, J=8 Hz, 1H), 7.14 (br s, 4H).

(h) 2-(S)-[2-[[3-(Dimethylamino)propyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Me, $R_{10}$=H, $R_7$=$R_8$=Me, n=3)

NMR ($CDCl_3$; δ from TMS): 0.92 (t, 3H, J=8 Hz), 0.95 (t, 3H, J=8 Hz), 1.06 (t, 3H, J=8 Hz), 1.2–1.4 (m, 2H), 1.6–2.0 (m, 6H), 2.26 (s, 3H), 2.32 (s, 3H), 2.42 (s, 3H), 2.2–2.4 and 2.5–2.65 (2m, 2H), 2.91 (s, 3H), 3.1–3.3 and 3.3–3.5 (2m, 2H), 4.62 and 4.72 (2ABq, 2H, J=16 Hz), 4.78 (q. 1H, J=8 Hz), 5.11 and 5.13 (2s, 1H), 7.03 (br d, 1H, J=8 Hz), 7.13 (br s, 4H).

(i) 2-(S)-[2-[[2-(Di-(2-methoxyethyl)amino)ethyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$=H, $R_7$=$R_8$=$CH_2CH_2OMe$, n=2)

NMR ($CDCl_3$; δ from TMS): 0.92 (t, 3H, J=8 Hz), 0.96 (t, 3H, J=8 Hz), 1.06 (t, 3H, J=8 Hz), 1.2–1.5 (m, 2H), 1.6–2.0 (m, 6H), 2.33 (s, 3H), 2.6–2.9 (m, 6H), 2.93 (s, 3H), 3.32 (s, 3H), 3.33 (s 3H), 3.0–3.5 (m, 6H), 4.62 and 4.72 (2 ABq, 2H, J=16 Hz), 4.78 (q, 1H, J=8 Hz), 5.09 and 5.14 (2 s, 1H), 7.00 and 7.04 (2 br d, 1H, J=8 Hz), 7.14 (br s, 4H).

(j) 2-(S)-[2-[[2-((2-Methoxyethyl)-ethylamino)ethyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$=H, $R_7$=Et, $R_8$=$CH_2CH_2OMe$, n=2)

NMR ($CDCl_3$; δ from TMS): 0.90–1.10 (m, 12H), 1.2–1.4 (m, 2H), 1.6–2.0 (m, 6H), 2.30 (s, 3H), 2.4–2.8 (m, 6H), 2.92 and 2.93 (2s, 3H), 3.0–3.6 (m, 2H), 3.32 (br s, 3H), 4.63 and 4.71 (2 ABq, 2H, J=16 Hz), 4.78 (q, 1H, J=8 Hz), 5.08 and 5.12 (2s, 1H), 7.00 and 7.04 (2 br d, 1 H, J=8 Hz), 7.12 (br s, 4H).

(k) 2-(S)-[2-[[2-((2-Ethoxyethyl)-isopropylamino)ethyl]methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Me, $R_{10}$=H, $R_7$=iPr, $R_8$=$CH_2CH_2OEt$, n=2)

NMR ($CDCl_3$; δ from TMS): 0.9–1.2 (m, 18H), 1.2–1.4 (m, 2H), 1.6–2.0 (m, 6H), 2.25 (s, 3H), 2.5–2.7 (m, 4H), 2.8–3.0 (m, 1H), 2.87 and 2.89 (2 s, 3H), 3.0–3.6 (m, 7H), 4.63 and 4.71 (2 ABq, 2H, J=16 Hz), 4.78 (q, 1H, J=8 Hz), 5.04 and 5.10 (2 s, 1H), 6.96 and 7.00 (2 br d, 1H, J=8 Hz), 7.14 (br s, 4H).

(l) 2-(S)-[2-[[2-(Diethylamino)ethyl]ethylamino]-2-oxoethoxy]-3,3-di ethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Et, $R_{10}$=H, $R_7$=$R_8$=Et, n=2)

NMR ($CDCl_3$ δ from TMS): 0.8–1.2 (m, 18H), 1.2–1.4 (m, 2H), 1.6–2.0 (m, 6H), 2.30 (s, 3H), 2.4–2.6 (m, 6H), 3.0–3.5 (2 m, 4H), 4.5–4.8 (2 AB q, 2H, J=16 Hz), 4.7 (m, 1H), 5.02 and 5.06 (2 s, 1H), 7.0 (m, 1H), 7.14 (br s, 4H).

(m) 2-(S)-[2-[[2-(Diisopropylamino)ethyl]ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Et, $R_{10}$=H, $R_7$=$R_8$=iPr, n=2)

NMR ($CDCl_3$; δ from TMS): 0.8–1.4 (m, 26H), 1.6–2.0 (m, 6H), 2.31 (s, 3H), 2.4–2.8 (m, 4H), 2.8–3.4 and 3.7–3.9 (3 m, 4H), 4.5–4.9 (2 ABq, 2H, J=16 Hz), 4.78 (m, 1H), 5.08 and 5.18 (2 s, 1H), 7.0 (m, 1H), 7.14 (br s, 4H).

(n) 2-(S)-[2-[[2-((2-Methoxyethyl)-ethylamino)ethyl]ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_{3=4}$-Me, $R_9$=Et, $R_{10}$=H, $R_7$=Et, $R_8$=$CH_2CH_2OMe$, n=2)

NMR ($CDCl_3$; δ from TMS): 0.9–1.2 (m, 15H), 1.2–1.4 (m, 2H), 1.6–2.0 (m, 6H), 2.31 (s, 3H), 2.5–2.7 (m, 6H), 3.1–3.5 (m, 6H), 3.33 and 3.35 (2 s, 3H), 4.5–4.9 (2 ABq, 2H, J=16 Hz), 4.80 (m, 1H), 5.10 and 5.16 (2 s, 1H), 7.04 (m, 1H), 7.14 (br s, 4H).

(o) 2-(S)-[2-[[2-((2-Methoxyethyl)-isopropylamino)ethyl]ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Et, $R_{10}$=H, $R_7$=iPr, $R_8$=$CH_2CH_2OEt$, n=2)

NMR ($CDCl_3$; δ from TMS): 0.9–1.2 (m, 21H), 1.2–1.4 (m, 2H), 1.6–2.0 (m, 6H), 2.32 (s, 3H), 2.5–2.7 (m, 4H), 2.90 (m, 1H), 3.0–3.6 (m, 8H), 4.5–4.9 (2 AB q, 2H, J=16 Hz), 4.78 (m, 1H), 5.10 and 5.16 (2 s, 1H), 7.02 (m, 1H), 7.14 (br s, 4H).

(p) 2-(S)-[[2-(Morpholin-1-yl)ethyl]ethylamino]-2oxoethoxy]-3,3-diethyl-N-[1-(R)-(4-methylphenyl)-butyl]-4-oxo-1-azetidinecarboxamide (6b ; R=R$_1$=Et, R$_5$=R$_6$=H, M=Pr, R$_2$=H, R$_3$=4-Me, R$_9$=Et, R$_{10}$=H, R$_7$ and R$_8$ joined together form morpholine moiety, n=2)

NMR (CDCl$_3$; δ from TMS): 0.8–1.4 (m, 14H), 1.4–2.0 (m, 6H), 2.33 (s, 3H), 2.3–2.6 (m, 6H), 3.1–3.6 (m, 4H), 3.6–3.8 (m, 4H), 4.5–4.9 (2 AB q, 2H, J=16 Hz), 4.78 (m, 1H), 5.09 and 5.10 (2 s, 1H), 7.02 (br d, 1H), 7.14 (br s, 4H).

(q) 2-(S)-[2-[[2-((2-Ethoxyethyl)-isopropylamino)ethyl]-propylamino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=Pr, R$_{10}$=H, R$_7$=iPr, R$_8$=CH$_2$CH$_2$OEt, n=2)

NMR (CDCl$_3$; δ from TMS): 0.8–1.2 (m, 21H), 1.2–1.4 (m, 2H), 1.4–1.6 (m, 2H), 1.6–2.0 (m 6H), 2.31 (s, 3H), 2.5–2.7 (m, 4H), 2.90 (m, 1H), 3.0–3.6 (m, 8H), 4.5–4.9 (2 AB q, 2H, J=16 Hz), 4.78 (m, 1H), 5.10 and 5.15 (2 s, 1H), 7.04 (m, 1H), 7.14 (br s, 4H).

(r) 2-(S)-[2-[[2-(Diethylamino)ethyl]propylamino]-2-oxoethoxy]-3,3-diethyl-N-[1- (R)-(4-methylphenyl)-butyl]-4-oxo-1-azetidinecarboxamide (6b; R=R$_1$=Et, R$_5$=R$_6$=H, M=Pr, R$_2$=H, R$_3$=4-Me, R$_9$=Pr, R$_{10}$=H, R$_7$=R$_8$=Et, n=2)

NMR (CDCl$_3$; δfrom TMS): 0.8–1.1 (m, 18H), 1.2–1.4 (m, 2H), 1.4–1.6 (m, 2H), 1.6–2.0 (m, 6H), 2.32 ( s, 3H), 2.4–2.6 (m, 6H), 3.0–3.5 ( m, 4H ), 4.5–4.9 ( 2 ABq, 2H, J=16 Hz ), 4.78 (m, 1H), 5.10 and 5.14 (2 s, 1H), 7.00 (m, 1H), 7.14 (br s, 4H)

(s) 2-(S)-[2-[[2-((2-Methoxyethyl)-ethylamino)ethyl]-isopropylamino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=iPr, R$_{10}$=H, R$_7$=Et, R$_8$=CH$_2$CH$_2$OMe, n=2)

NMR (CDCl$_3$; δ from TMS) 0.85–1.2 (m, 18H), 1.2–1.4 (m, 2H), 1.6–2.0 (m, 6H), 2.32 ( s, 3H), 2.5–2.8 (m, 6H), 3.1–3.5 (m, 4H), 3.34 (s, 3H), 3.78 (m, 1H), 4.5–4.9 (2 AB q, 2H, J=16 Hz), 4.78 (m, 1H), 5.06 and 5.15 (2 s, 1H), 7.0 (m, 1H), 7.14 (br s, 4H)

(t) 2-(S)-[2-[2-(4-Methyl)piperazin-1-yl]-2-oxoethoxy]-3,-3-diethyl-N-[1-(R)-(4-methylphenyl)-butyl]4-oxo-1-azetidinecarboxamide (6b; R=R$_1$=Et, R$_5$=R$_6$=H, M=Pr, R$_2$=H, R$_3$=Me, R$_9$ and R$_8$ are joined together to form a piperazine ring, R$_7$=Me, R$_{10}$=H, n=2)

NMR (CDCl$_3$ from TMS): 0.92, 0.97, 1.06 (3t, J=8 Hz, 9H), 1.2–1.5 (m, 2H), 1.6–2.0 (m, 6H), 2.30 (s, 3H), 2.32 (s, 3H), 2.37 (t, J=6 Hz, 4H), 3.35 (br t, J=6 Hz, 2H), 3.61 (br t, J=6 Hz, 2H), 4.67 (ABq, J=14 Hz, 2H), 4.76 (q, J=8 Hz, 1H), 5.07 (s, 1H), 7.02 (br d, J=8 Hz, 1H), 7.14 (br s, 4H).

(u) 2-(S)-[2-[2-(4-Cyclopropyl)piperazin-1-yl]-2-oxoethoxy]-3,-3-diethyl-N-[1-(R)-(4-methylphenyl)-butyl]-4-oxo-1-azetidinecarboxamide (6b; R=R$_1$=Et. R$_5$=R$_6$=H, M=Pr, R$_2$=H, R$_3$=Me, R$_8$ and R$_9$ are joined together to form a piperazine ring, R$_7$=cyclopropyl, R$_{10}$=H, n=2)

NMR (CDCl$_3$; δ from TMS); 0.35–0.5 (m, 4H), 0.92, 0.96, 1.06 (3t, J=8 Hz, 9H), 1.1–1.5 (m, 2H), 1.5–2.0 (m, 6H), 2.31 (s, 3H), 2.56 (t, J=5 Hz, 4H), 3.18 (br t, J=5 Hz, 2H), 3.54 (br t, J=5 Hz, 2H), 4.67 (ABq, J=14 Hz, 2H), 4.76 (q, J=8 Hz, 1H), 5.08 (s, 1H), 7.02 (br d, J=8 Hz, 1H), 7.14 (br s, 4H).

(v) 2-(S)-[2-[2-(4-Ethyl)piperazin-1-yl]-2-oxo ethoxy]-3,-3-diethyl-N-[1-(R)-(4-methylphenyl)-butyl]-4-oxo-1-azetidinecarboxamide (6b; R=R$_1$=Et, R$_5$=R$_6$=H, M=Pr, R$_2$=H, R$_3$=Me, R$_8$ and R$_9$ are joined together to form a piperazine ring, R$_7$=Et, R$_{10}$=H, n=2)

NMR (CDCl$_3$; δ from TMS); 0.93, 0.97, 1.07, 1.10 4t, J=8 Hz, 9H), 1.2–1.5 (m, 2H), 1.6–2.0 (m, 6H), 2.33 (s, 3H), 2.37 (m, 6H), 3.35 (br t, J=6 Hz, 2H), 3.62 (br t, J=6 Hz, 2H), 4.67 ( ABq, J=14 Hz, 2H ), 4.77 (q, J=8 Hz, 1H), 5.09 (s, 1HJ), 7.02 (br d, J=8 Hz, 1H), 7.15 (br s, 4H).

(w) 2-(S)-[2-[2-(4-Isopropyl)piperazin1-yl]-2-oxoethoxy]-3,-3-diethyl-N-[1-(R)-(4-methylphenyl)-butyl-4-oxo-1-azetidinecarboxamide (6b; R=R$_1$=Et, R$_5$=R$_6$=H, M=Pr, R$_2$=H, R$_3$=Me, R$_8$ and R$_9$ are joined together to form a piperazine ring, R$_7$=i-Pr, R$_{10}$=H, n=2)

NMR (CDCl$_3$; δ from TMS); 0.8–1.1 (m, 15H), 1.2–1.5 (m, 2H), 1.5–2.0 (m, 6H), 2.30 (s, 3H), 2.37 (m, 4H), 2.52 (m, 1H), 3.35 (m, 2H), 3.61 (m, 2H), 4.67 (ABq, J=14 Hz, 2H), 4.76 (q, J=8 Hz, 1H), 5.08 (s, 1H), 7.02 (br d, J=8 Hz, 1H), 7.14 (br s, 4H).

(x) 2-(S)-[2-[2-(4-(2-Hydroxy)ethyl)piperazin-1-yl]-2-oxoethoxy]-3,-3-diethyl-N[1-(R)-(4-methylphenyl)-butyl]-4-oxo-1-azetidinecarboxamide (6b; R=R$_1$=Et, R$_5$=R$_6$=H, M=Pr, R$_2$=H, R$_3$=Me, R$_9$ and R$_8$ are joined together to form a piperazine ring, R$_7$=CH$_2$CH$_2$OH, R$_{10}$=H, n=2)

NMR (CDCl$_3$; δ from TMS); 0.92, 0.96, 1.06 (3t, J=8 Hz, 9H), 1.2–1.5 (m, 2H), 1.6–2.0 (m, 6H), 2.32 (S, 3H), 2.50 (t,J=5 Hz, 4H), 2.57 (t, J=5 Hz, 2H), 3.37 (br t, J=5 Hz, 2H), 3.64 (m, 4H), 4.68 (ABq, J=14 Hz, 2H), 4.77 ( q, J=8 Hz, 1H), 5.09 (s, 1H), 7.02 (br d, J=8 Hz, 1H), 7.14 (s, 4H).

EXAMPLE 13

2-(S)-[2-[[2-(Diethylamino)ethyl]methylamino]-2-oxo-(1-(S)-methyl)ethoxy]-3,3-diethyl-N-[1-(R)-(4-methylphenyl)butyl]-4-oxo-1-azetidinecarboxamide (6b; R=R$_1$=Et, R$_5$=H, R$_6$=Me, M=Pr, R$_2$=H, R$_3$=4-Me, R$_9$=Me, R$_{10}$=H, R$_7$=R$_8$=Et, n=2)

A solution of the material prepared in Example 8 (320 mg. 0.79 mmole) in CH$_2$Cl$_2$ (5 ml) was cooled to 0° C. and 2 drops of DMF were added. Oxalyl chloride (0.140mL, 1.58 mmol) was then added and the reaction was allowed to warm to room temperature under nitrogen. After 1 hour the reaction was evaporated in vacuo and an additional portion of CH$_2$Cl$_2$ added and evaporated to remove excess oxalyl chloride.

The residue was taken up in CH$_2$Cl$_2$ (10 mL) and cooled to 0° C. in an ice bath. N,N-Diethylamino-N'-methyl-ethylenediamine (310 mg, 2.37 mmol) in CH$_2$Cl$_2$ (5mL) was added slowly and the reaction was allowed to warm to room temperature. After 1 hr the reaction was diluted with CH$_2$Cl$_2$ and the solution was washed successively with aqueous K$_2$CO$_3$ and then brine before being dried over Na$_2$SO$_4$, filtered and evaporated to dryness.

The residue was purified by chromatography on silica gel using a gradient of EtOAc to MeOH/EtOAc (1:9) to afford 268 mg of the title compound.

NMR (CDCl$_3$, δ from TMS): 0.9–1.1 (m, 15H), 1.2–1.5 (m and d (J=8 Hz), 5H), 1.6–2.0 (m, 6H), 2.32 (s, 3H), 2.4–2.8 (m and q (J=8 Hz), 6H), 2.95 and 2.06 (2 s, 3H), 3.1–3.7 (m, 2H), 4.80 (q, 1H, J=8 Hz), 4.84 (s, 1H), 5.19 (q, 1H, J=8 Hz), 6.96 and 7.05 (2 br d, 1H, J=8 Hz), 7.14 (br s, 4H).

Following substantially the same procedure as described in Example 13, but using an appropriately substituted diamine, compounds (a)-(f) were prepared:

(a) 2-(S)-[2-[[2-(Dimethylamino)ethyl]methylamino]-2-oxo-(1-(S)-methyl)ethoxy]-3,3-diethyl-N-[1-(R)-(4-methylphenyl)butyl]-4-oxo-1-azetidinecarboxamide (6b; R=$R_1$=Et, $R_5$=H, $R_6$=Me, M=Pr, $R_2$=H, $R_3$=4-Me, $R_9$=Me, $R_{10}$=H, $R_7$=$R_8$=Me, n=2)

NMR (CDCl$_3$, δ from TMS): 0.92 (t, 6H, J=8 Hz), 1.07 (t, 3H, J=8 Hz), 1.1-1.4 (m, 2H), 1.35 (d, 3H, J=6 Hz), 1.5-2.0 (m, 6H), 2.24 (s, 6H), 2.33 (s, 3H), 2.3-2.6 (2 m, 2H), 2.93 and 3.05 (2s, 3H), 3.2-3.7 (m, 2H), 4.80 (m, 1H), 4.84 (s, 1H), 5.20 (q, 1H, J=6 Hz), 6.98 and 7.06 (2 br d, J=8 Hz, 1H), 7.14 (br s, 4H).

(b) 2-(S)-[2-[[2-(Diethylamino)ethyl]amino]-2-oxo-(1-(S)-methyl)ethoxy]-3,3-diethyl-N-[1-(R)-(4-methylphenyl)butyl]-4-oxo-1-azetidinecarboxamide (6b; R=$R_1$=Et, $R_5$=H, $R_6$=Me, M=Pr, $R_2$=H, $R_3$=4-Me, $R_9$=$R_{10}$=H, $R_7$=$R_8$=Et, n=2)

NMR (CDCl$_3$, δ from TMS): 0.91 (t, 3H, J=8 Hz), 0.93 (t, 3H, J=8 Hz), 1.0-1.2 (m, 9H), 1.2-1.5 (m, 2H), 1.45 (d, 3H, J=6 Hz), 1.6-2.0 (m, 6H), 2.31 (s, 3H), 2.6-2.8 (m, 6H), 3.40 (m, 2H), 4.62 (q, 1H, J=6 Hz), 4.78 (q, 1H, J=8 Hz), 5.04 (s, 1H), 6.95 (br d, 1H, J=8 Hz), 7.14 (br s, 4H).

(c) 2-(S)-[2-[[2-(Dimethylamino)ethyl]amino]-2-oxo-(1-(S)-methyl)ethoxy]-3,3-diethyl-N-[1-(R)-(4-methylphenyl)butyl]-4-oxo-1-azetidinecarboxamide (6b; R=$R_1$=Et, $R_5$=H, $R_6$=Me, M=Pr, $R_2$=H, $R_3$=4-Me, $R_9$=$R_{10}$=H, $R_7$=$R_8$=Me, n=2)

NMR (CDCl$_3$, δ from TMS): 0.90 (t, 3H, J=8 Hz), 0.92 (t, 3H, J=8 Hz), 1.05 (t, 3H, J=8 Hz), 1.2-1.4 (m, 2H), 1.44 (d, 3H, J=6 Hz), 1.5-2.0 (m, 6H), 2.20 (s, 6H), 2.32 (s, 3H), 2.39 (t, 2H, J=6 Hz), 3.31 (br q, 2H, J=6 Hz), 4.59 (q, 1H, 6 Hz), 4.79 (q, 1H, J=8 Hz), 5.01 (s, 1H), 6.90 (m, 2H), 7.14 (br s, 4H).

(d) 2-(S)-[2-[[2-(Morpholin-1-yl)ethyl]amino]-2-oxo-(1-(S)-methyl)ethoxy]-3,3-diethyl-N-[1-(R)-(4-methylphenyl)butyl]-4-oxo-1-azetidinecarboxamide (6b; R=$R_1$=Et, $R_5$=H, $R_6$=Me, M=Pr, $R_2$=H, $R_3$=4-Me, $R_9$=$R_{10}$=H, $R_7$ and $R_8$ joined together form morpholine moiety, n=2)

NMR (CDCl$_3$, δ from TMS): 0.70 (t, 3H, J=8 Hz), 0.94 (t, 3H, J=8 Hz), 0.99 (t, 3H, J=8Hz), 1.16 (d, 3H, J=7 Hz), 1.2-1.5 (m, 2H), 1.6-1.8 (m, 6H), 2.32 (s, 3H), 2.4-2.6 (m, 6H), 3.2-3.5 (m, 6H), 4.05 (m, 1H), 4.63 (m, 1H), 5.08 and 5.18 (2 s, 1H), 6.52 (br d, 1H, J=8 Hz), 6.96 (m, 1 H), 7.14 (m, 4H).

(e) 2-(S)-[2-[[2-(Diisopropylamino)ethyl]amino]-2-oxo-(1-(S)-methyl)ethoxy]-3,3-diethyl-N-[1-(R)-(4methylphenyl)butyl]-4-oxo-1azetidinecarboxamide (6b; R=$R_1$=Et, $R_5$=H, $R_6$=Me, M=Pr, $R_2$=H, $R_3$=4-Me, $R_9$=H, $R_{10}$=H, $R_7$=$R_8$=iPr, n=2)

NMR (CDCl$_3$, δ from TMS): 0.8-1.2 (m, 24H), 1.2-1.5 (m, 6H), 1.6-2.0 (m, 6H), 2.31 (s, 3H), 2.4-2.5 (m, 2H), 3.00 (m, 2H), 3.1-3.3 (m, 2H), 4.00 (q, 1H, J=8 Hz), 4.62 (q, 1H, J=8 Hz), 5.10 and 5.15 (2 s, 1H), 6.7-6.9 (m, 2H), 7.14 (m, 4H).

(f) 2-(S)-[2-[[2-(Dimethylamino)ethyl]ethylamino]-2-oxo-(1-(S)-methyl)ethoxy]-3,3-diethyl-N-[1-(R)-(4-methylphenyl)butyl]-4-oxo-1-azetidinecarboxamide (6b; R=$R_1$=Et, $R_5$=H, $R_6$=Me, M=Pr, $R_2$=H, $R_3$=4-Me, $R_9$=Et, $R_{10}$=H, $R_7$=$R_8$=Me, n=2)

NMR (CDCl$_3$, δ from TMS): 0.93 (t, 6H, J=8 Hz), 1.08 (t, 3H, J=8 Hz), 1.1-1.4 (m, 5H), 1.37 (d, 3H, J=6 Hz), 1.5-2.0 (m, 6H), 2.28 (s, 3H), 2.30 (s, 3H), 2.32 (s, 3H), 2.3-2.8 (2 m, 2H), 3.0-3.6 (m, 4H), 4.78 (m, 1H), 4.79 (s, 1H), 5.17 (br q, 1H, J=6H), 7.00 (m, 1H) 7.14 (m, 4H).

EXAMPLE 14

N,N-Diisopropyl-N'-ethyl-ethylenediamine

Step A: Preparation of N,N-diisopropyl-N'-benzyloxy-carbonyl-ethylenediamine

N,N-Diisopropyl-ethylenediamine (4.94 gm, 0.034 mol) was dissolved in CH$_2$Cl$_2$ (20 mL) and cooled to 0° C. under nitrogen. Triethylamine (4.7 mL) and benzyloxycarbonyl chloride (4.9 mL) were then added and the mixture was stirred overnight while being allowed to reach room temperature. The mixture was then poured into Et$_2$O (250 mL) and K$_2$CO$_3$ was added. This mixture was then washed successively with H$_2$O and brine and the pooled aqueous layers were back-extracted with Et$_2$O. The pooled organic layers were dried over Na$_2$SO$_4$, filtered and evaporated to dryness. This crude reaction product was then purified on a silica gel column using initially EtOAc/hexane (1:1) as eluent followed by MeOH/EtOAc (3:7) containing 2% Et$_3$N to afford 2.9 gm of the title compound suitable for use in the next step.

NMR (CDCl$_3$, δ from TMS): 1.06 (m, 6H), 1.17 (d, 6H, J=8 Hz), 2.2-2.9 (m, 4H), 3.1-3.3 (m, 2H), 4.30 (v br s, 1H), 5.15 (s, 2H), 7.38 (br s, 5H).

Step B: Preparation of N,N-diisopropyl-N'-ethyl-N'-benzyloxycarbonyl-ethylenediamine The material prepared above in Step A (1.24 gm, 4.5 mmol) was dissolved in DMF (15 mL) and cooled to 0° C. under nitrogen. At this point, ethyl iodide (1.0 gm, 9 mmol) was added and NaH (9 mmol) was added in portions. The stirred reaction mixture was then allowed to rise to room temperature and after 3.5 hr an additional 1.5 mmol each of both ethyl iodide and NaH were added. After 4 hr, the reaction was evaporated to dryness and the product was purified by chromatography on a silica gel column developed with EtOAc, to give 1.1 gm of the title compound.

NMR (CDCl$_3$, δ from TMS): 0.8-1.2 (m, 8H), 1.15 (d, 6H, J=8 Hz), 2.2-2.6 (m, 4H), 2.6-3.2 (2 m, 4H), 5.16 (s, 2H), 7.34 (br s, 5H).

Step C: Preparation of N,N-diisopropyl-N'-ethyl-ethylenediamine

The material prepared above in Step B (1.10 gm, 3.6 mmol) was dissolved in thiophene free THF (17 mL) and 200 mg of 10% Pd on carbon was added. This mixture was hydrogenated at 40 p.s.i. for 2 hr, at which point tlc showed complete reaction to the title compound, and then was filtered through Celite. The filtrate so obtained was not concentrated but was used directly in subsequent reactions.

Following substantially the same procedure as described in Example 14, the following diamines (a)-(i) were prepared:

(a) N,N-Diisopropyl-N'-methyl-ethylenediamine.
(b) N-Methyl-N-[2-(2,6 dimethylpiperidin-1-yl) ethyl]-amine
(c) N,N-Di-(2-methoxyethyl)-N'-methyl-ethylenediamine
(d) N,N-Diethyl-N'-ethyl-ethylenediamine
(e) N-Diisopropyl-N'-ethyl-ethylenediamine
(f) N-Ethyl-N-[2-(morpholin-1-yl)ethyl]-amine
(g) N,N-Di-(2-methoxyethyl)-N'-ethyl-ethylenediamine
(h) N-Propyl-N-[2-(morpholin-1-yl)ethyl]-amine
(i) N,N-Diethyl-N'-propyl-ethylenediamine

EXAMPLE 15

N-Ethyl-N-(2-methoxyethyl)-N'-ethyl-ethylenediamine

Step A: Preparation of N-benzyloxycarbonyl-N'-ethyl-N'-(2-methoxyethyl)-glycine amide A solution of N-Benzyloxycarbonylglycine (5.0 gm, 24 mmol) in $CH_2Cl_2$ (50 mL) was cooled to 0° C. and a few drops of dimethylformamide (DMF) were added. Oxalyl chloride (2.3 mL) was then added and the solution was allowed to warm up to room temperature under nitrogen. After 1 hr the mixture was evaporated to dryness and the residue was redissolved in $CH_2Cl_2$ (50 mL) and cooled in an ice-bath. A mixture of diisopropylethylamine (8.4 mL) and 2-methoxyethyl-ethylamine (3.7 gm) in $CH_2Cl_2$ (25 mL) was then added slowly. After 30 min the mixture was poured into dil. HCl/ice and extracted 2× with $CH_2Cl_2$. The pooled organic layers were then washed With brine, dried over $Na_2SO_4$, filtered and evaporated to dryness. The crude product so obtained was purified by chromatography on silica gel using EtOAc/hexane (step gradient of 1:1 to 4:1) as eluent. This gave 5.0 gm of the title compound as an oil which was used in the next step.

NMR ($CDCl_3$; δ from TMS): 1.1–1.3 (m, 3H), 3.33 (s, 3H), 3.3–3.6 (m, 6H), 4.07 (m, 2H), 5.13 (s, 2H), 5.83 (br m, 1H), 7.34 (m, 5H).

Step B: Preparation of N-benzyloxycarbonyl-N-ethyl-N'-ethyl-N'-(2-methoxyethyl)-glycine amide The material prepared above in Step A (5.0 gm, 17 mmol) was dissolved in DMF (100 mL) and cooled in an ice-bath under nitrogen. Ethyl iodide (2.7 mL, 34 mmol) was added and then NaH (26 mmol) was added in portions over 15 min. After an additional 30 min the mixture was poured into 2N HCl/ice and this mixture was then extracted twice with $Et_2O$. The pooled organic layers were washed with brine and then dried over $Na_2SO_4$, filtered and evaporated to dryness. The crude product so obtained was then purified by chromatography on silica gel using EtOAc/hexanes (gradient of 1:1 to 4:1) as eluent to give 4.75 gm of the title compound as an oil.

NMR ($CDCl_3$; δ from TMS): 1.0–1.3 (m, 6H), 3.2–3.6 (m, 11H), 3.95–4.2 (m, 2H), 5.12 and 5.17 (2 s, 2H), 7.2–7.4 (m, 5H)

Step C: Preparation of N-benzyloxycarbonyl-N-ethyl-N'-(2-methoxyethyl)-N,'-ethyl-ethylenediamine The material prepared as described above in Step B .(4.5 gm, 14 mmol) was dissolved in THF (50 mL) under nitrogen and $BH_3.Me_2S$ (42 mL of 1M solution, 42 mmol) was added. This mixture was stirred at room temperature under nitrogen for 20 hr and then MeOH (30 mL) was added slowly. After addition was complete, this mixture was stirred at room temperature for 3 days and then was evaporated to dryness. The residue so obtained was purified by chromatography on silica gel using initially EtOAc as eluent and then MeOH-/EtOAc (1:9) containing 2% $Et_3N$ to give 3.5 gm of the title compound as a pure oil.

NMR ($CDCl_3$: δ from TMS): 0.9–1.2 (m, 3H), 1.13 (br t, 3H, J=7 Hz), 2.4–2.8 (m, 6H), 3.2–3.5 (m, 9H), 5.12 (s, 2H), 7.34 (m, 5H).

Step D: Preparation of N-ethyl-N-(2-methoxyethyl)-N'-ethyl-ethylenediamine

This oil was dissolved in thiophene free THF (20 mL) and and 200 mg of 10% Pd on carbon was added. This mixture was hydrogenated at 40 p.s.i. for 2.5 hr, at which point tlc showed complete reaction to the title compound, and then was filtered through Celite. The filtrate so obtained was not concentrated but was used directly in subsequent reactions.

Following substantially the same procedure as described in Example 15, the following diamines (a)–(e) were prepared:
(a) N-Methyl-N-(2-methoxyethyl)-N'-ethyl-ethylenediamine
(b) N-Isopropyl-N-(2-ethoxyethyl)-N'-ethyl-ethylenediamine
(c) N-Isopropyl-N-(2-ethoxyethyl)-N',propyl-ethylenediamine
(d) N,N-Di-(2-methoxyethyl)-N'-propyl-ethylenediamine
(e) N-Ethyl-N-(2-methoxyethyl)-N'-propyl-ethylenediamine Following substantially the same procedure as described in Example 15, except that ethylamine was used in place of 2-methoxyethyl-ethylamine in Step A, and omitting Steps B and Step D, N-benzyloxycarbonyl-N'-ethyl-ethylenediamine was prepared.

Following substantially the same procedure as described in Example 15, except that N-benzyloxycarbonylsarcosine was used as the starting material and ethylamine was used in place of 2-methoxyethylethylamine in Step A, and omitting Steps B and D, N-benzyloxycarbonyl-N-methyl,N'-ethyl-ethylenediamine was prepared.

Following substantially the same procedure as described in Example 15, except that N-benzyloxycarbonylsarcosine was used as the starting material, and omitting Step B, the following diamines (a)–(b) were prepared:
(a) N-Ethyl-N-(2-methoxyethyl)-N'-methyl-ethylenediamine
(b) N-Isopropyl-N-(2-ethoxyethyl)-N'-methyl-ethylenediamine

EXAMPLE 16

N-Ethyl-N-(2-methoxyethyl)-ethylenediamine

N-Ethyl-N-(2-methoxyethyl)-ethylenediamine (500 mg) was dissolved in acetone (1 mL) and THF (10 mL) and 150 mg of 10% Pd on carbon was added. The mixture was hydrogenated at 40 p.s.i. for 1–2 hr and then was filtered through Celite and the filtrate was evaporated to dryness to give the title compound (600 mg) as a tlc pure product which was suitable for use in subsequent steps.

NMR ($CDCl_3$; δ from TMS): 0.96 (t, 3H, J=8 Hz), 1.00 (d, 6H, J=6 Hz), 2.4–2.8 (m, 10H), 3.28 (s, 3H), 3.38 (t, 2H, J=8 Hz).

Following substantially the same procedure as described in Example 16, the following diamines (a)–(d) were prepared:
(a) N,N-Dimethyl-N'-isopropyl-ethylenediamine
(b) N,N-Diethyl-N'-isopropyl-ethylendiamine
(c) N,N-Diisopropyl-N'-isopropyl-ethylenediamine
(d) N-[2-(pryrrolidin-1-yl)ethyl-isopylamine

EXAMPLE 17

2-(S)-[2-[[2-(Isopropylmethylamino)ethyl]methylamino]-2-oxoethoxy]-3,3-diethyl-N-[1-(R)-(4-methylphenyl)-butyl]-4-oxo-1-azetidinecarboxamide (6b; $R=R_1=Et$, $R_5=R_6=H$, $M=Pr$, $R_2=H$, $R_3=4$-Me, $R_9=Me$, $R_{10}=H$, $R_7=R_8=iPr$, $n=2$)

Method A:

Step A: Preparation of 2-(S)-[2-[[2-(Methylamino)ethyl]methylamino]-2-oxoethoxy]-3,3-diethyl-N-[1-(R)-(4-methylphenyl)butyl]-4-oxo-1-azetidinecarboxamide As described in Example 12, material from Example 7 (600 mg, 1.5 mmol) was converted to its acid chloride with oxalyl chloride (0.20 mL, 2.3 mmol) in $CH_2Cl_2$ (30 mL). The crude acid chloride was dissolved in $CH_2Cl_2$ (15 mL) and added over 5 min to a mixture of diisopropylethylamine (0.54 mL, 3.1 mmol) and sym-dimethyl-ethylenediamine (400 mg, 4.6 mmol) in $CH_2Cl_2$ (50mL) at 0° C. After 1 hour the reaction was poured into aqueous $K_2CO_3$ and extracted with 2 portions of $CH_2Cl_2$. The combined organic layers were washed with brine, dried over $Na_2SO_4$, filtered and evaporated to dryness. The residue was purified by chromatography on silica gel eluting first with EtOAc/hexanes (1:1) and then with MeOH/EtOAc/$Et_3N$ (10:90:1) to give 100 mg of the title compound as an oil which was suitable for use in the next step.

NMR ($CDCl_3$; δ from TMS): 0.92 (t, 3H, J=8 Hz), 0.96 (t, 3H, J=8 Hz), 1.06 (t, 3H, J=8 Hz), 1.2–1.5 (m, 2H), 1.6–2.0 (m, 6H), 2.32 (s, 3H), 2.43 (br s, 3H), 2.76 (m, 2H), 2.94 (s, 3H), 3.2–3.6 (2m, 2H), 4.5–4.9 (m, 2H), 5.13 (s, 1H), 7.04 (m, 1H), 7.14 (br s, 4H).

Step B: Preparation of 2-(S)-[2-[[2-(Isopropylmethylamino)ethyl]methylamino]-2-oxoethoxy]-3,3-diethyl-N-[1-(R)-(4-methylphenyl)butyl]-4oxo-1-azetidinecarboxamide A solution of the material from Example 17, Step A (100 mg) was dissolved in THF (5 mL) and hydrogenated under 40 p.s.i. of $H_2$ in the presence of acetone (1 mL) and 10% Pd on carbon (100 mg) for 6 hr. The reaction mixture was filtered through Celite, concentrated and the residue was then purified by preparative TLC eluting with MeOH/EtOAc/hexanes/$Et_3N$ (5:70:25:1) to afford 80 mg of the title compound.

NMR ($CDCl_3$; δ from TMS): 0.9–1.1 (m, 15H), 1.2–1.5 (m, 2H), 1.6–2.0 (m, 6H), 2.23 and 2.27 (2 s, 3H), 2.32 (s, 3H), 2.4–2.6 (m, 2H), 2.7–3.0 (m, 1H), 2.94 and 2.95 (2 s, 3H), 3.0–3.5 (m, 2H), 4.5–4.9 (m, 2H), 5.10 and 5.13 (2 s, 1H), 7.04 (m, 1H), 7.14 (br s, 4H).

Method B:

Step A: Preparation of 2-(S)-[2-[[2-((Benzyloxycarbonyl)methylamino)ethyl]-methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Me, $R_{10}$=H, $R_7$=Me, $R_8$=CO—OCH$_2$C$_6$H$_5$, n=2)

As described in Example 12, material from Example 7 (2.2 gm, 0.0056 mol) was converted to it's acid chloride with oxalyl chloride (0.62 mL, 0.0071 mol) in methylene chloride (25 mL) containing a trace of dimethylformamide. The crude acid chloride so obtained was dissolved in methylene chloride (50 mL) and cooled in an ice-bath. A solution of N-benzyloxycarbonyl-N,N'-dimethyl-ethylenediamine, prepared as described in Example 32 (1.3 gm, 0.0056 mol) and diisopropylethylamine (2.1 mL, 0.0122 mol) in methylene chloride (10 mL) was added slowly over 1min and reaction was then stirred at 0° C. until complete. The reaction was then worked-up in the usual fashion to give 2.8 gm of the title compound as an oil that was suitable for use in the next step.

Step B: Preparation of 2-(S)-[2-[[2-(Isopropylmethylamino)ethyl]-methylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$ =H, M=Pr, $R_2$=H, $R_3$=4-Me, $R_9$=Me, $R_{10}$=H, $R_7$=Me, $R_8$=iPr, n=2)

A solution of the material prepared as described above in Example 17, Method B, Step A (2.7 gm, 0.0045 mol) in methanol (50 mL) and acetone (10 mL) was hydrogenated over 10% Pd/carbon (250 mg) at 40 psi for 5 hrs. The reaction mixture was then filtered and the filtrate was evaporated to dryness. The residue so obtained was purified by flash chromatography on silica gel using EtOAc, then $Et_3N$/MeOH/EtOAc (1:5:94), and finally, $Et_3N$/MeOH/EtOAc (2:10:88) as eluants. This gave the title compound (1.6 gm) as an oil which was identical in all respects to material prepared above by Example 17, Method A.

EXAMPLE 18

2-(S)-[2-[[2-(Ethylmethylamino)ethyl]-ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Et, $R_{10}$=H, $R_7$=Me, $R_8$=Et, n=2)

Step A: Preparation of 2-(S)-[2-[[2-((Benzyloxycarbonyl)ethylamino)ethyl]]-ethylamino ]-2-oxoethoxy]-3,3-diethyl-N-[1-(R)-(4-methylpheny)butyl]-4-oxo- 1-azetidinecarboxamide (6b; R=$R_1$=Et, $R_5$=$R_6$=H, M=Pr, $R_2$= H, $R_3$=4-Me, $R_9$=Et, $R_{10}$=H, $R_7$=Et, $R_8$=CO—OCH$_2$C$_6$H$_5$, n=2)

This was prepared as described above in Example 17, Method B, Step A, except that N-benzyloxycarbonyl-N,N'-diethyl-ethylenediamine, prepared as described in Example 32, was used as the diamine in place of N-benzyloxycarbonyl-N,N'-dimethyl-ethylenediamine. The title compound was obtained as an oil that was suitable for use in the next step.

Step B: Preparation of 2-(S)-[2-[[2-(ethylmethylamino)ethyl]-ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Et, $R_{10}$=H, $R_7$=Me, $R_8$=Et, n=2)

This was prepared as described above in Example 17, Method B, Step B, except that 2-(S)-[2-[[2-((benzyloxycarbonyl)ethylamino)ethyl]-ethylamino]-2-oxoethoxy]-3,3-diethyl-N-[1-(R)-(4-methylphenyl)butyl]-4-oxo-1-azetidinecarboxamide, prepared as described above in Example 18, Step A was used as the starting material, and formaldehyde was used in place of acetone. This gave the title compound as pure oil.

NMR ($CDCl_3$ δ from TMS): 0.9–1.4 (m, 17H), 1.6–2.0 (m, 6H), 1.14 and 2.18 (2s, 3H, 2.51 (s, 3H), 2.4–2.6 (m, 4H) 3.1–3.5 (2m, 4H), 4.67 (ABq, J=14 Hz, 2H) 4.76 (m, 1H), 5.09 and 5.12 (2s, 1H), 7.04 (m, 1H), 7.13 (s, 4H).

EXAMPLE 19

2-(S)-[2-[[2-Methylaminoethyl]-ethylamino]-2-oxoethoxy]-3,3-diethyl-N-[1-(R)-(4-methylphenyl)butyl]-4-oxo-1-azetidinecarboxamide (6b; R=$R_1$=Et, $R_5$=$R_6$=H, M=Pr, $R_2$=H, $R_3$=4-Me, $R_9$=Et, $R_{10}$=H, $R_7$=Me, $R_8$=H, n=2) and
2-(S)-[2-[[2-ethylaminoethyl]-methylamino]-2-oxoethoxy]-3,3-diethyl-N-[1-(R)-(4-methylphenyl)butyl]-4-oxo-1-azetidinecarboxamide (65; R=$R_1$=Et, $R_5$=$R_6$=H, M=Pr, $R_2$=H, $R_3$=4-Me, $R_9$=Me, $R_{10}$=H, $R_7$=Et, $R_8$=H, n=2)

Step A: Preparation of 2-(S)-[2-[[2-((Benzyloxycarbonyl)ethylamino)ethyl]-ethylamino]-2-oxoethoxy]-3,3- diethyl-N-[1-(R)-(4-methylphenyl)butyl]-4-oxo-1-azetidinecarboxamide (6b; R=R$_1$=Et, R$_5$=R$_6$=H, M=Pt, R$_2$=H, R$_3$=4-Me, R$_9$=Et, R$_{10}$=H, R$_7$=Me, R$_8$=CO—OCH$_2$C$_6$H$_5$, n=2)

As described in Example 12, material from Example 7 (0.25 gm, 0.00064 mol) was converted to it's acid chloride with oxalyl chloride (0.085 mL) in methylene chloride (5 mL) containing a trace of dimethylformamide. After evaporation to dryness of the reaction mixture, the crude acid chloride so obtained was dissolved in methylene chloride (10 mL) and cooled in an ice-bath. A solution of N-benzyloxycarbonyl-N-methyl-N'-ethyl-ethylenediamine, prepared as described in Example 15 (0.2 gm,) and triethylamine (0.2 mL) in methylene chloride was added and reaction was then stirred at rt for 1 hr. The reaction was then diluted with methylene chloride, and the solution was washed successively with 2N HCl and brine, dried over Na$_2$SO$_4$, filtered, and evaporated to dryness. Preparative TLC (silica gel developed with EtOAc/hexanes, 1:1) afforded the title compound (0.15 gm) as an oil which was suitable for use in the next step. NMR (CDCl$_3$ d from TMS): 0.9–1.1 (m, 12H), 1.1–1.5 (m, 2H), 1.5–2.0 (m, H), 2.31 (s, 3H), 2.97 (br s, 3H), 2.8–3.6 (m, H), 4.4–4.9 (m, 3H), 5.0–5.2 (m, 3H), 7.02 (br d, 1H, J=8 Hz), 7.13 (br s, 4H), 7.31 (br s, 5H).

Step B: 2-(S)-[2-[[2-Methylaminoethyl]-ethylamino]-2-oxoethoxy]-3,3-diethyl-N-[1-(R)-(4-methylphenyl)-butyl]-4-oxo-1-azetidinecarboxamide (6b; R=R$_1$=Et, R$_5$=R$_6$=H, M=Pr, R$_2$=H, R$_3$=4-Me, R$_9$=Et, R$_{10}$=H, R$_7$=Me, R$_8$=H, n=2) and 2-(S)-[2-[[2-ethylaminoethyl]-methylamino]-2-oxoethoxy]-3,3diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=Me, R$_{10}$=H, R$_7$=Et, R$_8$=H, n=2)

The material prepared as described above in Example 19, Step A (0.15 gm,, 0.025 mol) was dissolved in methanol (5 mL) and L-malic acid (0.035 gm, 0.025 mol) was added followed by 10% Pd/carbon (0.05 gm). This mixture was hydrogenated at 40 psi for 2 hr when TLC indicated complete reaction. The mixture was filtered and evaporated to dryness to afford the L-malic acid salt of the title compound, 2-(S)-[2-[2-methylaminoethyl]-ethylamino]-2-oxoethoxy]-3,3-diethyl-N-[1-(R)-(4-methylphenyl)butyl]-4-oxo-1azetidinecarboxamide, as an oil.

NMR of free amine (CDCl$_3$ δ from TMS): 0.9–1.1 (m, 12H), 1.1–1.4 (m, 2H), 1.6–1.9 (2 m's, 4H), 2.29 (s, 3H), 2.42 (d, 3H, J=6 Hz), 2.6–2.9 (m, 2H), 3.3–3.6 (m, 4H), 4.5–4.8 (m, 3H), 5.10 (br s, 1H), 7.03 (m, 1H), 7.12 (br s, 4H).

Upon extended storage of the above mentioned salt at rt the material rearranges to an isomeric equilibrium mixture of 2-(S)-[2-[[2-methylaminoethyl]ethylamino]-2-oxoethoxy]-3,3-diethyl-N-[1-(R)-(4methylphenyl)-butyl]-4-oxo-1-azetidinecarboxamide and 2-(S)-[2-[[2-ethylaminoethyl]-methylamino]-2-oxoethoxy]-3,3-diethyl-N-[1-(R)-(4-methylphenyl)butyl]-4-oxo-1-azetidinecarboxamide which can be separated by chromatography. NMR (CDCl$_3$ δ from TMS): 0.9–1.0 (m, 6H), 1.0–1.1 (m, 6H), 1.2–1.4 (m, 2H), 1.6–1.95(2 m's, 6H), 2.30 (s, 3H), 2.6–2.9 (2 m's, 4H), 2.92 and 2.94 (2 s, 3H), 3.2–3.4 (m, 2H), 3.52 (br t, 2H, J=8 Hz), 4.5–4.8 (m, 3H), 5.11 (br s, 1H), 7.04 (2 d's, 1H, J=8Hz), 7.13 (br S, 4H).

EXAMPLE 20

2-(S)-[2-[[2-Aminoethyl]-ethylamino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=Et, R$_{10}$=H, R$_7$=R$_8$=H, n=2) and
2-(S)-[2-[[2-ethylaminoethyl]-amino]-2oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=R$_{10}$=H, R$_7$=Et, R$_8$=H, n=2)

Step A: Preparation of 2-(S)-[2-[[2-((Benzyloxycarbonyl)amino)ethyl]-ethylamino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=Et, R$_{10}$=H, R$_7$=Me, R$_8$=CO—OCH$_2$C$_6$H$_5$, n=2)

This was prepared as described above for Example 19, Step A, except that N-benzyloxycarbonyl-N'-ethyl-ethylenediamine, prepared as described in Example 15, was used in place of N-benzyloxycarbonyl-N-methyl-N,-ethyl-ethylenediamine. This gave the title compound as an oil suitable for use in the next step. NMR (CDCl$_3$ d from TMS): 0.9–1.2 (m, 12H), 1.2–1.4 (m, 2H), 1.5–2.0 (m, H), 2.30 (s, 3H), 3.1–3.6 (m, 6H), 4.65 (ABq, 2H, J=16 Hz), 4.75 (m, 1H), 5.0–5.15 (m, 3H), 5.45–5.65 (2 br t's, 1H), 6.95–7.05 (m, 1H), 7.10–7.20 (m, 4H), 7.30 (br s, 5H).

Step B: 2-(S)-[2-[[2-Aminoethyl]-ethylamino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=Et, R$_{10}$=H, R$_7$=R$_8$=H, n=2) and 2-(S)-[2-[[2-ethylaminoethyl]-amino]-2-oxoethoxy]-3,3-diethyl-N-[1-(R)-(4-methylphenyl)butyl]-4-oxo-1-azetidinecarboxamide (6b; R=R$_1$=Et, R$_5$=R$_6$=H, M=Pr, R$_2$=H, R$_3$=4-Me, R$_9$=R$_{10}$=H, R$_7$=Et, R$_8$=H, n=2)

The material prepared as described above in Example 20, Step A was hydrogenated as described in Example 19, Step B to afford the L-malic acid salt of 2-(S)-[2-[[2-aminoethyl]-ethylamino]-2-oxoethoxy]-3,3-diethyl-N-[1-(R)-(4-methylphenyl)butyl]-4-oxo-1-azetidinecarboxamide as an oil. As described for the material prepared in Example 19, Step B, this material also rearranged upon storage to an equilibrium mixture of isomers consisting of 2-(S)-[2-[[2-aminoethyl]ethylamino]-2-oxoethoxy]-3,3-diethyl-N-[1-(R)-(4-methylphenyl)-butyl]-4-oxo-1-azetidinecarboxamide and 2-(S)-[2-[[2-ethylaminoethyl]amino]-2-oxoethoxy]-3,3-diethyl-N-[1-(R)-(4-methylphenyl)butyl]-4-oxo-1azetidinecarboxamide. This process could be evaluated by HPLC analysis.

EXAMPLE 21

3-(N-Benzyloxycarbonyl-N-ethyl)-aminopropionic acid (13: R$_8$=Et, R$_{10}$=H, n=2)

Sodium hydride (0.52 gm) was suspended in DMF (20mL) and N-benzyloxycarbonylaminopropionic acid t-butyl ester (12; R$_{10}$=H, n=2, 2.79 gm, 10 mmol) was added in portions. After stirring for 15 min gas evolution had ceased and ethyl iodide (1 mL) was added. After stirring for 1 hr an additional 0.2 gm of NaH was added, along with 0.5 mL of ethyl iodide. The mixture was stirred for an additional hr and then was poured into 1.2 N HCl. This mixture was extracted with Et$_2$O and the pooled organic layers were washed with H$_2$O dried over Na$_2$SO$_4$, filtered and evaporated to dryness to give a residue of 2.6 gm. The residue was dissolved in anisole (2mL) and cold CF$_3$CO$_2$H (10mL) was added. This solution was cooled in an ice-bath and stirred for 1 hr before being diluted with dichloroethane and evaporated to dryness in vacuo to give 3.85 gm of an oil containing a mixture of the title compound and anisole which was sufficiently pure for the next step.

NMR (CDCl$_3$; δ from TMS): 1.14 (t, 3H, J=7 Hz), 2.66 (m, 2H), 3.35 (q, 2H, J=7 Hz), 3.58 (t, 2H, J=7 Hz), 5.16 (s, 2H), 7.34 (s, 5H).

EXAMPLE 22

4-(N-Benzyloxycarbonyl-N-ethyl)-amino-1-hydroxybutan-2-one (14; R$_8$=Et, R$_{10}$=H, n=2)

The material prepared above in Example 21 (3.85 gm) was dissolved in CH$_2$Cl$_2$(25mL) and DMF (10 drops) was added followed by oxalyl chloride (0.9 mL). After 20 min additional oxalyl chloride (0.1 mL) was added and the reaction was stirred for 10 min more. The reaction mixture was then evaporated to dryness and the residue was dissolved in Et$_2$O (25 mL). Diazomethane (prepared from 4 gm of KOH and 7 gm of N-nitroso-N-methylurea) in Et$_2$O was then added in portions. The solution was stirred in an ice-bath for 20 min and then was concentrated to /25 mL and diluted with acetone (25 mL). The mixture was concentrated again to /15 mL and acetone (50 mL) and H$_2$O (5 mL) were added followed by a solution of HClO$_4$ (1 mL) in H$_2$O (10 mL). This mixture was heated at 60° C. for 30 min and then cooled to room temperature. The reaction mixture was then partitioned between H$_2$O and Et$_2$O and the organic layer was washed with H$_2$O and brine before being dried over Na$_2$SO$_4$, filtered and evaporated to dryness. The crude product so obtained was purified by chromatography on silica gel developed with EtOAc/hexane (1:1 to 3:1) to give the title compound (0.31 gm) as chromatographically pure material suitable for use in subsequent steps.

NMR (CDCl$_3$; δ from TMS): 1.2 (t, 3H, J=7 Hz), 2.76 (m, 3H), 3.32 (q, 2H, J=7 Hz), 3.54 (t, 2H, J=7 Hz), 4.13 (br s, 2H), 5.11 (s, 2H), 7.34 (s, 5H)

EXAMPLE 23

(R,S)-3,3-Diethyl-2-[4-(N-benzyloxycarbonyl-N-ethyl)-amino-2-oxo-butoxy]-azetidin-4-one (15; R=R$_1$=R$_8$=Et, R$_{10}$=H, n=2)

(R,S)-2-Acetoxy-3,3-diethyl-azetidin-4-one (0.3 gm) was dissolved in benzene (3 mL) and the material prepared in Example 22 (0.31 gm) was added followed by Pd(OAc)$_2$ (30 mg) and Et$_3$N (0.16 mL). This mixture was stirred overnight and an additional 0.2 gm of (R,S)-2-acetoxy-3,3-diethyl-azetidin-4-one was added and stirring was continued for 7 hr more. The reaction mixture was then diluted with Et$_2$O and this solution was washed successively with H$_2$O, 1.2N HCl brine and then dried over Na$_2$SO$_4$, filtered and evaporated to dryness. The crude product so obtained was purified by chromatography on a silica gel column developed with EtOAc/hexane (1:1 to 3:1) to give 0.167 gm of the title compound as pure material.

NMR (CDCl$_3$; δ from TMS): 0.95 (t, 3H, J=7 Hz), 1.02 (t, 3H, J=7 Hz), 1.13 (t, 3H, J=7 Nz), 1.6–2.0 (m, 4H), 2.71 (m, 2H), 3.32 (q, 2H, J=7 Hz), 3.54 (m, 2H), 5.12 (s, 2H), 5.15 (s, 1H), 7.36 (m, 6H).

EXAMPLE 24

2-(S)-[4-(N-Benzyloxycarbonyl-N-ethylamino)-2-oxo-butoxy]-3,3-diethyl-N-[1-(R)-(4-methylphenyl)but-3enyl]-4-oxo-1-azetidinecarboxamide (16b; R=R$_1$=R$_8$=Et, R$_{10}$=H, M=allyl, R$_2$=H, R$_3$=4-Me, n=2)

The material prepared above in Example 23 (0.167 gm) was dissolved in DMF (1mL) and treated with (R)-a-allyl-(4-methylbenzyl)isocyanate (see EPO 37 549, 0.15 gm) and powdered K$_2$CO$_3$ (0.01 gm). After stirring for 1 hr the reaction mixture was diluted with Et$_2$O and this mixture was washed successively with H$_2$O (2×) and brine before being dried over Na$_2$SO$_4$, filtered and evaporated to dryness. The crude product so obtained was purified by chromatography on preparative thick layer silica gel plates developed with EtOAc/hexane (3: 7) to give 0.094 gm of the title compound as the chromatographically pure, higher Rf isomer suitable for use in the next step.

NMR (CDCl$_3$; δ from TMS): 0.9–1.2 (m, 9H), 1.6–2.0 (m, 4H), 2.31 (s, 3H), 2.55 (t, 2H, J=7 Hz), 2.66 (m, 2H), 3.29 (m, 2H), 3.49 (m, 2H), 4.58 (m, 2H), 4.8–5.2 (m, 6H), 5.66 (m, 1H), 6.9–7.4 (m, 10H).

EXAMPLE 25

2-(S)-[4-Ethylamino-2-oxo-butoxy]-3,3-diethyl-N-[1-(R)-(4-methylphenyl)butyl]-4-oxo-1-azetidinecarboxamide (17b; R=R$_1$=R$_8$=Et, R$_7$=H, R$_{10}$=H, M=propyl, R$_2$=H, R$_3$=4-Me, n=2)

The material prepared above in Example 24 (0.094 gm) was dissolved in EtOH (2 mL) and 20 mg of 10% Pd on carbon was added. This mixture was hydrogenated at 40 p.s.i. for 1 hr and then was filtered through Celite, washing the pad with EtOAc, and the filtrate was evaporated to dryness to give 0.090 gm of the title compound as chromatographically pure material which was suitable for subsequent use without further purification.

NMR (CDCl$_3$; δ from TMS): 0.8–1.2 (m, 12H), 1.2–1.46 (m, 2H), 1.6–2.0 (m, 6H), 2.32 (s, 3H), 2.4–3.20 (m, 6H), 4.4–5.1 (m, 4H), 6.9–7.3 (m, 6H).

EXAMPLE 26

2-(S)-[4-Diethylamino-2-oxo-butoxy]-3,3-diethyl-N-[1-(R)-(4-methylphenyl)butyl]-4-oxo-1-azetidinecarboxamide(17b; R=R$_1$=R$_7$=R$_8$=Et, R$_{10}$=H, M=propyl, R$_2$=H, R$_3$=4-Me, n=2)

The material prepared above in Example 25 (0,090 gm) was dissolved in EtOAc (3 mL) and acetaldehyde (0.2 mL) was added followed by 25 mg of 10% Pd on carbon. This mixture was hydrogenated at 40 p.s.i. for 2 hr and then was filtered through Celite, washing the pad with EtOAc, and the filtrate was evaporated to dryness. The crude product so obtained was purified by chromatography on a silica gel column, using EtOAc/Et$_3$N (49:1) as the eluent. The title compound (24 mg) was isolated as a chromatographically pure product.

NMR (CDCl$_3$; δ from TMS): 0.8–1.1 (m, 15H), 1.2–1.46 (m, 2H), 1.6–2.0 (m, 6H), 2.32 (s, 3H), 2.3–2.9 (m, 8H), 4.5–5.1 (m, 4H), 6.92 (br s, 1H), 7.0–7.2 (m, 4H).

EXAMPLE 27

2-(S)-[2-[2-diisopropylamino)ethyloxy]-2-oxoethoxy]-3,3-diethyl-N-[1-(R)-(4-methylphenyl)butyl]-4-oxo-1-azetidinecarboxamide A solution of the material prepared in Example 7 (0.171g, 0.44 mmol) in 2 ml of $CH_2Cl_2$ was cooled to 0° C. was then added and the solution was allowed to warm up to room temperature under lo nitrogen. After 30 min. the mixture was evaporated to dryness and the residue was dissolved in 2 ml of $CH_2Cl_2$. The solution was cooled to 0° and N,N-diisopropylaminoethanol (0.086. ml) and N,N-diisopropylethylamine (0.085 ml) were added. After stirring the reaction mix for 1 hr, it was diluted with $CH_2Cl_2$. and the solution was successively washed with 10% $Na_2CO_3$, water and brine before being dried over $Na_2CO_3$, filtered and evaporated to dryness. The cruded product so obtained was purified by chromatography using 10–30% EtOAr-hexane to afford 0.109 g of the title compound.

NMR ($CDCl_3$; δ from TMS): 0.8–1.1 (m, 21H), 1.32 (m, 2H), 1.6–2.0 (m, 6H), 2.31 (s, 3H), 2.62 (t, 3H, J=7 Hz), 2.98 (m, 2H), 4.04 (t, 2H, J=7 Hz), 4.58 (ABq, 2H, J=17 Hz), 4.75 (q, 1H, J=7 Hz), 5.09 (s, 1H), 6.95 (d, 1H, J=7 Hz), 7.12 (br s, 4h).

EXAMPLE 28

Benzyl 2-hydroxyisobutyrate

2-Hydroxyisobutyric acid (15 gm) was dissolved in benzyl alcohol (80 mL) at 0° C. and the solution was saturated with HCl gas. This solution was stored at rt overnight and then was poured into sat. $NaHCO_3$ solution. This was extracted twice with $CHCl_3$ and the combined organic extracts were dried ($Na_2SO_4$), filtered and evaporated to dryness. The residue so obtained was fractionally distilled and the title compound was obtained as a fraction that boiled at 85°–100° C. at 0.2 mm.

EXAMPLE 29

(R,S)-2-(2-Benzyloxy-1,1-dimethyl-2-oxoethoxy)-3,3-diethyl-azetidin-4-one (3; R=$R_1$=Et $R_5$=$R_6$=Me)

This was prepared as described above in Example 2 except that the benzyl 2-hydroxyisobutyrate prepared in Example 28 was used in place of the benzyl glycollate utilized in Example 2. The title compound was obtained as a pure oil after chromatography and was suitable for use in the next step.

NMR ($CDCl_3$δ from TMS): 0.90 (t, J=7 Hz, 3H), 0.99 (t, J=7 Hz, 3H), 1.48 (s, 6H), 1.5–1.9 (m, 4H), 4.78 (s, 1H), 5.17 (ABq, J=12 Hz, 2H), 7.36 (br s, 5H).

EXAMPLE 30

2-(S)-(1-Carboxy-1-methylethoxy)-3,3-diethyl-N-[1-(R)-(4-methylphenyl)butyl]-4-oxo-1-azetidinecarboxamide (5b; R=$R_1$=Et, $R_5$ =$R_6$=Me, M=Pr, $R_2$=H, $R_3$=4-Me).

Step A: Preparatin of 2-(S)-(2-Benzyloxy-1,1-dimethyl-2-oxoethoxy)-3,3-diethyl-N-[1-(R)-(4-methylphenyl)but-3-enyl]-4-oxo-1-azetidinecarboxamide (4b; R=$R_1$=Et, $R_5$=$R_6$=Me, M=allyl, $R_2$=H, $R_3$=4-Me).

This was prepared as described above in Example 5. The title compound was isolated after chromatography as the higher $R_f$product and was suitable for use in the next step as the higher $R_f$isomer.

Step B: Preparation of 2-(S)-(1-carboxy-1-methylethoxy)-3,3-diethyl-N-[1-(R)-(4-methylphenyl)butyl]-4-oxo-1-azetidinecarboxamide (5b; R=$R_1$=Et, $R_5$=$R_6$=Me, M=Pr, $R_2$=H, $R_3$=4-Me).

The material prepared above in Example 30, Step A was deblocked in the usual fashion by hydrogenation at 40psi over 5% Pd/carbon to give the title compound.

NMR ($CDCl_3$δ from TMS): 0.9–1.0 (m, 9H), 1.2–1.5 (m, 2H), 1.46 (s, 3H), 1.56 (s, 3H), 1.6–2.0 (m, 6H), 2.32 (s, 3H), 4.83 (q, J=8 Hz, 1H), 5.10 (s, 1H), 7.15 (ABq. J=8 Hz, 4H), 8.44 (br s, 1H), 8.72 (br d, J=8 Hz, 1H).

EXAMPLE 31

2-(S)-[2-[[2-(Dimethylamino)ethyl]ethylamino]-2-oxo-1,1-dimethyl-ethoxy]-3,3-diethyl-N-[1-(R)-(4-methylphenyl)butyl]-4-oxo-1-azetidinecarboxamide (6b; R=$R_1$=Et, $R_5$=$R_6$=Me, M=Pr, $R_2$=H, $R_3$=4-Me, $R_9$=Et, $R_{10}$=H, $R_7$=$R_8$=Me, n=2)

This can be prepared as described above in Example 9, except that the material prepared as described in Example 30 is used as the starting material in place of the 2-(S)-carboxymethoxy-3,3-diethyl-N-[1-(R)-(4-methylphenyl)butyl]-4-oxo-1azetidinecarboxamide used in Example 9.

Following substantially the same procedure as described in Example 31, but using an appropriately substituted diamine, compounds (a)–(d) can be prepared:

(a) 2-(S)-[2-[[2-(Dimethylamino)ethyl]methylamino]-2-oxo- 1,1-dimethyl-ethoxy]-3,3-diethyl-N-[1-(R)- (4-methylphenyl)butyl]-4-oxo-1-azetidinecarboxamide (6b; R=$R_1$=Et, $R_5$=$R_6$=Me, M=Pr, $R_2$=H, $R_3$=4-Me, $R_9$=Me, $R_{10}$=H, $R_7$=$R_8$=Me, n=2).

(b) 2-(S)-[2-[[2-(Diethylamino)ethyl]ethylamino]-2-oxo-1,1-dimethyl-ethoxy]-3,3-diethyl-N-[1-(R)-(4-methylphenyl)butyl]-4-oxo-1-azetidinecarboxamide (6b; R=$R_1$=Et, $R_5$=$R_6$=Me, M=Pr, $R_2$=H, $R_3$=4-Me, $R_9$=Et, $R_{10}$=H, $R_7$=$R_8$=Et, n=2).

(c) 2-(S)-[2-[[2-(Isopropylmethylamino)ethyl]methylamino]-2-oxo-1,1-dimethyl-ethoxy]-3,3-diethyl-N-[1-(R)-(4-methylphenyl)butyl]-4-oxo-1-azetidinecarboxamide (6b; R=$R_1$=Et, $R_5$=$R_6$=Me, M=Pr, $R_2$=H, $R_3$=4-Me, $R_9$=Me, $R_{10}$=H, $R_7$=Me, $R_8$=iPr, n=2).

(d) 2-(S)-[2-[[2-((2-Methoxyethyl)-methylamino)ethyl]ethylamino]-2-oxo-1,1-dimethyl-ethoxy]-3,3-diethyl-N-[1-(R)-(4-methylphenyl)butyl]-4-oxo-1-azetidinecarboxamide (6b; R=$R_1$=Et, $R_5$=$R_6$=Me, M=Pr, $R_2$=H, $R_3$=4-Me, $R_9$=Et, $R_{10}$=H, $R_7$=Me, $R_8$=$CH_2CH_2OMe$, n=2).

EXAMPLE 32

N-Benzyloxycarbonyl-N,N'-diethyl-ethylenediamine

A solution of N-N'-dibenzyloxycarbonyl-N, N'-diethylethylenediamine (15 gm, 39 mmol) in MeOH (100 ML) was hydrogenated at 40 p.s.i. over 1 gm of 10% Pd/C until ½ of the theoretical $H_2$ had been taken up (about 2 min). The reaction was filtered and evaporated. The residue was chromatographed (EtOAc, then 2% $EtN_3$/10% MeOH/88% EtOAc) to give 7.5 gm of recovered starting material and 2.6 gm of title compound.

Following substantially the same procedure as described in Example 32, except that N,N'-dibenzyloxycarbonyl-N,N'-dimethylethylenediamine was used as starting material, N-benzyloxycarbonyl-N, N'-dimethyl-ethylenediame was prepared.

Following substantially the same procedure as described in Examle 32, except that N,N'dibenzyloxycarbonylpiperazine was used as starting material, N-benzyloxycarbonylpiperazine was prepared.

EXAMPLE 33

2-(S)-[2-[[2-((Aminocarbonylmethyl)ethylamino)ethyl]-ethylamino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=Me$, $R_9=Et$, $R_{10}=H$, $R_7=Et$, $R_8=CH_2CONH_2$, $n=2$).

Step A: 2-(S)-[2-[[2-(Ethylamino)ethyl]-ethylamino]-2-oxoethoxy]-3,3-diethyl-N-[1-(R)-(4-methylphenyl)-butyl]-4-oxo-1-azetidinecarboxamide, citric acid salt (6b; $R=R_1=Et$, $R_5=R_6=H$, $M=Pr$, $R_2=H$, $R_3=Me$, $R_9=Et$, $R_{10}=H$, $R_7=Et$, $R_8=H$, $n=2$).

A solution of 2-(S)-[2-[[2-((benzyloxycarbonyl)ethylamino)ethyl]-ethylamino]-2-oxoethoxy]3,3-diethyl-N-[1-(R)-(4-methylphenyl)butyl]-4-oxo-1-azetidinecarboxamide, prepared as described in Example 18, Step A (3.5 gm, 5.6 mmol) was hydrogenated in EtOH (100%) (25 mL) at 40 p.s.i. over 10% Pd/C for 1 hr. The solution was filtered and evaporated. The residue was purified by flash chromatography using first EtOAc, then 2% Et₃N/10% MeOH/88% EtOAc to afford the title compound (2.4gm) as an oil. A portion of this oil (2.3 gm, 4.7 mmol) was taken up in MeOH (25 mL) and citric acid (900 mg, 4.7 mmol) added. After all the citric acid was in solution, the volatiles were removed in vacuo to afford the title compound (3.2 gm) as an oil.

Step B: 2-(S)-[2-[[2-((Aminocarbonylmethyl)ethylamino)ethyl]ethylamino]-2-oxoethoxy]-3,3-diethyl-N-[1-(R)-(4-methylphenyl)butyl]-4-oxo-1-azetidinecarboxamide (6b; $R=R_1=Et$, $R_5=R_6=H$, $M=Pr$, $R_2=H$, $R_3=Me$, $R_9=Et$, $R_{10}=H$, $R_7=Et$, $R_8=CH_2CONH_2$, $n=2$).

To a solution of material from Example 33, Step A (150 mg, 0.22 mmol) in CH₃CN (1 mL) was added iodoacetamide (60 mg, 0.33 mmol) and diisopropylethylamine (0.20 mL; 1.1 mmol). The solution was stirred at room temperature for 3 hrs. and was then concentrated in vacuo. The residue was chromatographed on 3×1000 μm silica gel plates using 2% Et₃N/10% MeOH/78% EtOAc as eluent to give 110 mg of title compound as an oil.

NMR (CDCl₃ δ from TMS): 0.9–1.2 (m, 15H), 1.2–1.4 (m, 2H), 1.6–1.9 (m, 6H), 2.30 (s, 3H), 2.5–2.7 (m, 4H), 3.09 and 3.11 (2s, 2H), 3.1–3.4 and 3.5–3.6 (2 m, 4H), 4.66 (ABq, J =15 Hz, 2H), 4.7–4.8 (m, 1H), 5.08 and 5.10 (2 s, 1H), 5.55 (br s, 1H), 7.01 (d, J=8 Hz, 1H), 7.15 (s, 4H), 7.18 (br s, 1H).

EXAMPLE 34

2-(S)-Carboxymethoxy-3,3-diethyl-N-[1-(R)-benzofuran-5-yl)butyl]-4-oxo-1-azetidinecarboxamide (5b; $R=R_1=Et$)

Step A:
4-(S)-2-(2-Allyloxy-2-oxoethoxy)-3,3-diethylazetidin-4-one (10; $R=R_1=Et$)

Using the acidification/extraction process described above in Example 3, Step A, 4-(S)-2-((3,3-diethyl-4-oxo-2-azetidinyl)oxy)acetic acid, (R)-α-methylbenzylamine (8.3 gm) was converted to 5.2 gm (100%) of the free acid, $[\alpha]_D$ (EtOH, c=1.5)= −31. To a solution of this free acid (1.0 gm, 5.0 mmol) and allyl bromide (0.75 gm, 6.0 mmol) in DMF (10 mL) was added powdered K₂CO₃ (1.0 gm, 10 mmol). The mixture was stirred at rt for 6 hrs. and was then poured into ice water and extracted with two portions of ether. The ether layers were washed with brine, combined, dried over Na₂SO₄ and evaporated. Flash chromatography (20–40% EtOAc/hexanes) afforded 1.0 gm (83%) of the title compound. $[\alpha]_D$ (EtOH, c=1.28)= −44.

Step B: 2-(S)-(2-Allyloxy-2-oxoethoxy-3,3-diethyl-N-[1-(R)-(benzofuran-5-yl)butyl]-4-oxo-1-azetidinecarboxamide (11; $R=R_1=Et$)

To a solution of material prepared in Example 34, Step A ( 2.3 gm, 9.5 mmol) and (R)-1-(benzofuran-5-yl)butylisocyanate (see EPO 337,549) (2.8 gm, 13 mmol) in CH₂Cl₂ (10 ml) was added Et₃N ( 2.0 mL, 13 mmol) and DMAP ( cat.). The solution was heated at 50° C. for 24 hours. The reaction was diluted with CH₂Cl₂ and washed with ice water containing 2N HCl (10 mL). The CH₂Cl₂ layer was washed with brine, dried over Na₂SO₄ and concentrated. The residue was purified by preparative LC (8% EtOAc/5% CH₂Cl₂/87% hexanes) to afford 2.0 gm (47%) of the title compound as an oil. The desired isomer was the higher R_f product.

NMR (CDCl₃, δ from TMS): 0.9–1.1 (3t, J=8 Hz, 9H), 1.1–1.4 (m, 2H), 1.6–2.0 (m, 6H), 4.68 (ABq, J=18 Hz, 2H), 4.69 (br d, J=4 Hz, 2H), 4.95 (q, J=8 Hz, 1H), 5.08–6.0 (m, 1H), 5.1–5.3 (m, 2H), 5.8–6.0 (m, 1H), 6.72 (m, 1H), 7.01 ( d, J=8 Hz, 1H), 7.1–7.2 (m, 1H), 7.4–7.5 (m, 2H), 7.80 ( d, J=2 Hz, 1H ).

Step C:
2-(S)-Carboxymethoxy-3,3-diethyl-N-[1-(R)-(benzofuran-5-yl)butyl]-4-oxo-1-azetidinecarboxamide (5b: $R=R_1=Et$).

A solution of material prepared in Example 34, Step B (1.9 gm, 4.2 mmol), Ph₃P (100 mg) and HOAc (1.5 mL) was degassed and placed under N₂. To this solution was added (Ph₃P)₄-Pd(O) (100 mg). The reaction was stirred at room temperature for 7 hours and then concentrated. The residue was purified by flash chromatography (30% EtOAc/70% hexanes) to give 150 mg of the starting allyl ester. Further elution with 1% HOAc/49% EtOAc/50% hexanes then afforded 1.6 gm (92%) of the title compound as an oil.

NMR (CDCl₃, δ from TMS): 0.93 (t, J=7 Hz, 6H), 1.03 (t, J=7 Hz, 3H), 1.2–1.5 (m, 2H), 1.6–2.0 (m, 6H), 4.54 (ABq, 18 Hz, 2H), 4.92 (q, J=8 Hz, 1H), 5.06 (s, 1H), 6.74 (dd, J=3 Hz, 1 Hz, 1H), 7.01 (br d, J=8 Hz, 1H), 7.20 (dd, J=2 and 8 Hz), 7.46 (d, J=8 Hz, 1H), 7.50 (br d, J=2 Hz, 1H), 7.61 (d, J=3 Hz, 1H).

EXAMPLE 35

2-(S)-[2-[[2-(Dimethylamino)ethy]-ethylamino]-2-oxoethoxy]-3,3-diethyl-N-[1-(R)-(benzofuran-5-yl)butyl]-4-oxo-1-azetidinecarboxamide (6b; $R=R_1=Et$, $R_5=R_6=H$, $M=Pt$, $R_2$ and $R_3=-OCHCH-$, $R_9=Et$, $R_{10}=H$, $R_7=R_8=Me$, $n=2$).

A solution of material prepared in Example 34, Step C (1.7 gm, 4.1 mmol) in CH₂Cl₂ (25 mL) was converted to its acid chloride with oxalyl chloride (0.54 mL, 6.1 mmol) as described in Example 9. The crude acid chloride was dissolved in CH₂Cl₂ (50 mL) and N,N-dimethyl-N'-ethyl-ethylenediamine (1.0 gm, 8.2 mmol) in CH₂Cl₂ (5 mL) was added while the reaction was cooled in an ice bath. After 1 hr, the reaction was poured into ice water containing K₂CO₃ solution and extracted twice with CH₂Cl₂. The CH₂Cl₂ layers were washed with brine, pooled, dried over Na₂SO₄ and evaporated. The residue was purified by flash chromatography eluting first with EtOAc, then with 2% Et₃N/10% MeOH/88% EtOAc to give 1.90 gm (90%) of the title compound as an oil.

NMR (CDCl₃; δ from TMS ): 0.9–1.2 (m, 12H), 1.2–1.5 (m, 2H), 1.6–2.0 (m, 6H), 2.15 and 2.26 ( 2s, 3H), 2.36 ( s, 3H), 2.3–2.6 (m, 2H), 3.1–3.6 (m, 4H), 4.72 (ABq, J=16 Hz, 2H), 4.8–4.95 (m, 1H), 5.08 and 5.10 (2 s, 1H), 6.51 (m, 1H), 7.08 (br d, J=8 Hz, 1H), 7.18 (dd, J=8 and 2 Hz, 1H), 7.43 (d, J=8 Hz, 1H), 7.46 (m, 1H), 7.58 (d, J=3 Hz).

Following substantially the same procedure as described in Example 35, but using an appropriately substituted diamine, compounds (a)–(c) were prepared.

(a) 2-(S)-[2-[[2-(Diethylamino)ethyl]-ethylamino]-2-oxoethoxy]-3,3-diethyl-N-[1-(R)-(benzofuran-5-yl)butyl]-4-oxo-1-azetidinecarboxamide (6b; R=R₁=Et, R₅=R₆=H, M=Pr, R₂ and R₃=—OCHCH—, R₉=Et, R₁₀=H, R₇=R₈=Et, n=2).

NMR ( CDCl₃; δ from TMS): 0.9–1.2 (m, 18H), 1.2–1.4 (m, 2H), 1.6–2.0 (m, 6H), 2.4–2.6 (m, 6H), 3.1–3.5 (m, 4H), 4.5–4.9 (m and 2 ABq, 3H), 5.08 and 5.12 (2 s, 1H), 6.51 (br d, J=3 Hz, 1H), 7.0–7.1 (m, 1H), 7.20 (dd, J=8 and 2Hz), 7.45 ( d, J=8 Hz ), 7.49 (br s, 1H), 7.60 ( d, J=3 Hz ).

(b) 2-(S)-[2-[[2-(Diethylamino)ethyl]-methylamino]-2-oxoethoxy]-3,3-diethyl-N-[1-(R)-(benzofuran-5-yl)butyl]-4-oxo-1-azetidinecarboxamide (6b; R=R₁=Et, R₅=R₆=H, M=Pr, R₂ and R₃=—OCHCH—, R₉=Me, R₁₀=H, R₇=R₈=Et, n=2).

NMR (CDCl₃; δ from TMS): 0.9–1.2 (m, 15H), 1.2–1.5 (m, 2H), 1.6–2.0 (m, 6H), 2.4–2.8 (m, 6H), 2.93 (br s, 3H), 3.0–3.5 (2 m, 2H), 4.5–4.9 (2 ABq, 2H), 4.90 ( q, J=8 Hz, 1H), 5.08 and 5.12 ( 2 s, 1H), 6.73 (br d, J=3 Hz, 1H), 7.05–7.15 (m, 1H), 7.19 (dd, J=8 and 2 Hz, 1H), 7.44 (d, J=8H, 1H), 7.49 (br s, 1H), 7.60 (d, J=3 Hz, 1H).

(c) 2-(S)-[2-[[2-(Dimethylamino)ethyl]-methylamino]-2-oxoethoxy]-3,3-diethyl-N-[1-(R)-(benzofuran-5-yl)butyl]-4-oxo-1-azetidinecarboxamide (6b; R=R₁=Et, R₅=R₆=H, M=Pr, R₂ and R₃=—OCHCH—, R₉=Me, R₁₀=H, R₇=R₈=Me, n=2).

NMR (CDCl₃; δ from TMS): 0.9–1.2 (m, 9H), 1.2–1.5 (m, 2H), 1.6–2.0 (m, 6H), 2.32 (br s, 6H), 2.4–2.5 (m, 2H), 2.92 (br s, 3H), 3.2–3.5 (2 m, 2H), 4.5–4.8 (2 ABq, J=16 Hz, 2H), 4.90 (q, J=8 Hz, 1H), 5.10 and 5.12 (2 s, 1H), 6.72 (br s, 1H), 7.1–7.2 (m, 1H), 7.20 (br d, J=8 Hz, 1H), 7.44 (d, J=8 Hz, 1H), 7.49 (br s, 1H), 7.60 (d, J=3 Hz, 1H).

EXAMPLE 36

2-(S)-Carboxymethoxy-3,3-diethyl-N-[1-(R)-(3,4-methylenedioxyphenyl)butyl]-4-oxo-1-azetidinecarboxamide (5b; R=R₁=Et, R₅=R₆=H, M=Pr, R₂ and R₃=—OCH₂O.

Step A:

2-(S)-(2-Benzyloxy-2-oxoethoxy)-3,3-diethyl-N-[1-(R)-(3,4-methylenedioxyphenyl)butyl]-4-oxo-1-azetidinecarboxamide (4b; R=R₁=Et, R₅=R₆=H, M=Pr, R₂ and R₃=—OCH₂O.

To a solution of material prepared in Example 3, Step B (3.5 gm, 12.0 mmol) and (R)-α-allyl-3,4-methylenedioxybenzyl isocyanate (see EPO 337,549) (3.3 gm, 15.2 mmol) in CH₂Cl₂ (50 mL) was added Et₃N (4.3 mL, 24 mmol) and DMAP (cat.). The reaction was heated at 50° C. for 16 hrs and then poured into ice water containing 2N HCl (10 mL) and was then extracted twice with CH₂Cl₂. The CH₂Cl₂ layers were washed with brine, combined, dried over Na₂SO₄ and evaporated. The residue was purified by flash chromatography eluting with 5% CH₂Cl₂/5% EtOAc/90% hexanes, then 5% CH₂Cl₂/10% EtOAc/85% hexanes to afford 5.2 gm (85%) of the title compound as an oil. Only a trace of the lower R_f isomer was formed.

NMR (CDCl₃; δ from TMS): 0.93 (t,J=8 Hz 3H) 1.01 (t, J=8 Hz, 3H), 1.5–1.9 (m, 4H), 2.49 (t, J=8 Hz, 2H), 4.59 (ABq, J=17 Hz, 2H), 4.76 (q, J=8 Hz, 1H), 5.07 (s, 1H), 5.13 (ABq, J=14 Hz, 2H), 5.0–5.2 (m, 2H), 5.6–5.7 (m, 1H), 5.9 (s, 2H), 6.65–6.75 (m, 3H), 6.97 (d, J=8 Hz, 1H), 7.3–7.4 (m, 5H).

Step B:

2-(S)-Carboxymethoxy-3,3-diethyl-N-[1-(R)-(3,4-methylenedioxyphenyl)butyl]-4-oxo-1-azetidinecarboxamide (5b; R=R₁=Et, R₅=R₆=H, M=Pr, R₂ and R₃=—OCH₂O.

The major higher R_f material prepared above in Example 36, Step A (5.0 gm, 0.10 mmol) was dissolved in EtOH (50 mL) and 10% Pd/C (600 mg) was added. This mixture was hydrogenated at 40 p.s.i. for 3 hrs and was then filtered through Celite and the filtrate was evaporated to dryness to give 4.0 gm (97%) of the title compound as an oil suitable for use in the next step.

NMR (CDCl₃, δ from TMS): 0.93 (t, J=8 Hz, 3H), 0.96 (t, J=8 Hz, 3H), 1.05 ( t, J=8 Hz, 3H), 1.1–1.5 (m, 2H), 1.5–1.9 (m, 6H), 4.59 ( ABq, J=17 Hz, 2H ), 4.76 ( q, J=8 Hz, 1H ), 5.07 (s, 1H), 5.9 (s, 2H), 6.65–6.75 (m, 3H), 6.97 (d, J=8 Hz, 1H).

EXAMPLE 37

2-(S)-[2-[[2-(Dimethylamino)ethyl]-ethylamino]-2-oxoethoxy]-3,3-diethyl-N-[1-(R)-(3,4-methylenedioxyphenyl)butyl]-4-oxo-1-azetidinecarboxamide (6b; R=R₁=Et, R₅=R₆=H, M=Pr, R₂ and R₃=—OCH₂O—, R₉=Et, R₁₀=H, R₇=R₈=Me, n=2).

A solution of material prepared in Example 36, Step B (0.25 gm, 0.6 mmol) in CH₂Cl₂ (5 mL) was converted to its acid chloride with oxalyl chloride (0.080 mL, 0.9 mmol) as described in Example 9. The crude acid chloride was dissolved in CH₂Cl₂ (50 mL) and N,N-dimethyl-N'-ethyl-ethylenediamine (0.20 mL, 1.2 mmol) in CH₂Cl₂ (5 mL) was added while the reaction was cooled in an ice bath. After 1 hr, the reaction was poured into ice water containing K₂CO₃ solution and extracted twice with CH₂Cl₂. The CH₂Cl₂ layers were washed with brine, pooled, dried over Na₂SO₄ and evaporated. The residue was purified by preparative TLC eluting with 2% Et₃N/10% MeOH/88% EtOAc to give 0.25 gm (90%) of the title compound as an oil.

NMR (CDCl₃; δ from TMS): 0.9–1.2 (m, 12H), 1.2–1.5 (m, 2H), 1.6–2.0 (m, 6H), 2.15 and 2.26 (2 s, 3H), 2.3–2.6 (m, 2H), 3.1–3.6 (m, 4H), 4.72 (ABq, J=16 Hz, 2H), 4.8–4.95 (m, 1H), 5.08 and 5.10 (2 s, 1H), 5.9 (s, 2H), 6.65–6.75 (m, 3H), 6.97 (d, J=8 Hz, 1H).

Following substantially the same procedure as described in Example 37, but using an appropriately substituted diamine, compounds (a)–(e) were prepared.

(a) 2-(S)-[2-[[2-(Diethylamino)ethy]-ethylamino]-2-oxo-ethoxy]-3,3-diethyl-N-[1-(R)-(3,4-methylenedioxy-phenyl)butyl]-4-oxo-1-azetidinecarboxamide (6b; R=R$_1$=Et, R$_5$=R$_6$=H, M=Pr, R$_2$ and R$_3$=—OCH$_2$O—, R$_9$=Et, R$_{10}$=H, R$_7$=R$_8$=Et, n=2).

NMR (CDCl$_3$; δ from TMS): 0.9–1.2 (m, 15H), 1.2–1.5 (m, 2H), 1.6–2.0 (m, 6H), 2.3–2.6 (m, 6H), 3.1–3.6 (m, 4H), 4.73 (ABq, J=16 Hz, 2H), 4.8–5.0 (m, 1H), 5.08 and 5.11 (2 s, 1H), 5.90 (s, 2H), 6.65–6.75 (m, 3H), 6.97 (d, J=8 Hz, 1H).

(b) 2-(S)-[2-[[2-(2-Methoxyethyl)methylamino)ethy]e-thylamino]-2-oxoethoxy]-3,3-diethyl-N-[1-(R)-(3,4-methylenedioxyphenyl)butyl]-4-oxo-1-azetidine carboxamide (6b; R=R$_1$=Et, R$_5$=R$_6$=H, M=Pr, R$_2$ and R$_3$=—OCH$_2$O—, R$_9$=Et, R$_{10}$=H, R$_7$=CH$_2$CH$_2$OMe, R$_8$=Me, n=2).

NMR (CDCl$_3$; δ from TMS): 0.9–1.2 (m, 12H), 1.2–1.5 (m, 2H), 1.6–2.0 (m, 6H), 2.32 (s, 3H), 2.3–2.7 (m, 4H), 3.1–3.6 (m, 4H), 3.33 and 3.35 (2 s, 3H), 3.46 (t, J=6 Hz, 2H), 4.73 (ABq, J=16 Hz, 2H), 4.8–4.90 (m, 1H), 5.09 and 5.11 (2 s, 1H), 5.91 (s, 2H), 6.65–6.75 (m, 3H), 6.97 (d, J=8 Hz, 1H).

(c) 2-(S)-[2-[[2-(Dimethylamino)ethyl]-iso-propylamino]-2-oxoethoxyl]-3,-3-diethyl-N-[1-(R)-(3,4- methylenedioxyphenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$=i=Pr, R$_{10}$=H, R$_7$=R$_8$=Me, n=2)

NMR (CDCl$_3$; δ from TMS); 0.9–1.2 (m, 15), 1.2–1.5 (m, 2H), 1.6–2.0 (m, 6H), 2.15 and 2.26 (2s, 6H), 2.3–2.6 (m, 2H), 3.1–3.5 (m, 2H), 3.78 (m, 1H), 4.67 (ABq, J=14 Hz, 2H), 4.76 (q, J=8 Hz, 1H), 5.07 (s, 1H), 5.94 (s, 2H), 6.62 (m, 3H), 7.00 (br d, J=8 Hz, 1H).

(d) 2-(S)-[2-[2-(4-Methyl)piperazin-1-yl]-2-oxoethoxy]-3,-3-diethyl-N-[1-(R)-(3,4-methylenedioxyphenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$ and R$_8$ are joined together to form a piperazine ring, R$_7$=Me, R$_{10}$=H, n=2)

NMR (CDCl$_3$; δ from TMS); 0.94, 0.97, 1.05 (3 t, J=8 Hz, 9H), 1.2–1.4 (m, 2H), 1.6–2.0 (2m, 6H), 2.29 (s, 3H), 2.30 (s, 3H), 2.37 (t, J=6 Hz, 4H), 3.35 (br t, J=6 Hz, 2H), 3.60 (br t, J=6 Hz, 2H), 4.69 (ABq, J=14 Hz, 2H), 4.62 (q, J=8 Hz, 1H), 5.10 (s, 1H), 5.93 (s, 2H), 6.64 (m, 3H), 6.92 (br d, J=8 Hz, 1H).

(e) 2-(S)-[2-[2-(4-Cyclopropyl)piperazin-1-yl]-2-oxoe-thoxy]-3,3-diethyl-N-[1-(R)-(3,4-methylenedioxy-phenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$ and R$_8$ are joined together to form a piperazine ring, R$_7$=cyclopropyl, R$_{10}$=H, n=2)

EXAMPLE 38

2-(S)-[2-[2-(Piperazin-1-yl)-2-oxoethoxy]-3,3-diethyl-N-[1-(R)-(3,4-methylenedioxyphenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$ and R$_8$ are joined together to form a piperazine ring, R$_7$=H, R$_{10}$=H, n=2)

Step A:
2-(S)-[2-[2-(4-Benzyloxycarbonyl-piperazin-1-yl]-2-oxoethoxy]-3,3-diethyl-N-[1-(R)-(3,4-methylenedi-oxyphenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$ and R$_8$ are joined together to form a piperazine ring, R$_7$=CBz, R$_{10}$=H, n=2)

Following essentially the same procedure as Example 37, except using N-benzyloxycarbonylpiperazine, prepared in as Example, 32, the title compound was prepared.

Step B: 2-(S)-[2-[2-(Piperazin-1-yl]-2-oxoethoxy]-3,-3-diethyl-N-[1-(R)-(3,4-methylenedioxyphenyl)-butyl]-4-oxo-1-azetidinecarboxamide (6b; R=R$_1$=Et, R$_5$=R$_6$=H, M=Pr, R$_2$ and R$_3$=—OCH$_2$O—, R$_9$ and R$_8$ are joined together to form a piperazine ring, R$_7$=H, R$_{10}$=H, n=2)

Following essentially the same procedure as Example 33, Step A, except using the material prepared in Example 38, Step A, the title compound was prepared.

NMR (CDCl$_3$; δ from TMS); 0.92, 0.97, 1.06 (3 t, J=8 Hz, 9H), 1.2–1.4 (m, 2H), 1.6–2.0 (2m, 7H), 2.80 (t, J=6 Hz, 4H), 3.35 (br t, J=6 Hz, 2H), 3.65 (br t, J=6 Hz, 2H), 4.65 (ABq, J=14 Hz, 2H), 4.69 (q, J=8 Hz, 1H), 5.08 (s, 1H), 5.94 (s, 2H), 6.74 (m, 3H), 6.95 (br d, J=8 Hz, 1H).

EXAMPLE 39

2-(S)-[2-[2-(Piperazin-1-yl]-2-oxoethoxy]-3,-3-diethyl-N-[1-N-[1-(R)-(4-methylphenyl)-butyl]-4-oxo-1-azetidinecarboxamide (6b; R=R$_1$=Et, R$_5$=R$_6$=H, M=Pr, R$_2$=H, R$_3$=Me, R$_9$ and R$_8$ are joined together to form a piperazine ring, R$_7$=H, R$_{10}$=H, n=2

Step A: 2-(S)-[2-[2-(4-Benzyloxycarbonyl-piperazin-1-yl]-2-oxoethoxy]-3,-3-diethyl-N-[1-(R)-(4-methyl-phenyl)-butyl]-4-oxo-1-azetidinecarboxamide (6b; R=R$_1$=Et, R$_5$=R$_6$=H, M=Pr, R$_2$=H, R$_3$=Me, R$_9$ and R$_8$ are joined to form a piperazine ring, R$_7$=CBz, R$_{10}$=H, n=2)

Following essentially the same procedure as Example 18, Step A, except using N-benzyloxycarbonylpipera-zine, as prepared in Example 32, the title compound was prepared.

Step B: 2-(S)-[2-[2-(Piperazin-1-yl]-2-oxoethoxy]-3,-3-diethyl-N-[1-(R)-(3,4-methylenedioxyphenyl)-butyl]-4-oxo-1-azetidinecarboxamide (6b; R=R$_1$=Et, R$_5$=R$_6$=H, M=Pr, R$_2$=H, R$_3$=Me, R$_9$ and R$_8$ are joined together to form a piperazine ring, R$_7$=H, R$_{10}$=H, n=2)

Following essentially the same procedure as Example 33, Step A, except using the material prepared in Example 39, Step A, the title compound was prepared.

NMR (CDCl$_3$; δ from TMS); 0.92, 0.97, 1.06 (3 t, J=8 Hz, 9H), 1.2–1.4 (m, 2H), 1.6–2.0 (2m, 7H), 2.30 (s, 3H), 2.80 (t, J=6 Hz, 4H), 3.35 (br t, J=6 Hz, 2H), 3.65 (br t, J=6 Hz, H), 4.65 (ABq, J=14 Hz, 2H), 4.69 (q, J=8 Hz, 1H), 5.08 (s, 1H), 7.02 (br d, J=8 Hz, 1H), 7.14 (br s, 4H).

What is claimed is:

1. A compound of formula I

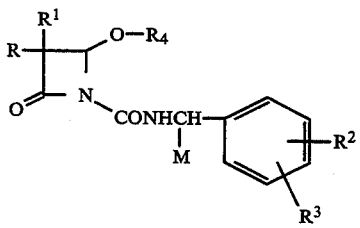

wherein

R is $C_{1-6}$ alkyl;

$R^1$ is $C_{1-6}$ alkyl or $C_{1-6}$ alkoxy-$C_{1-6}$ alkyl;

M is
- (1) hydrogen,
- (2) $C_{1-6}$ alkyl,
- (3) hydroxy $C_{1-6}$ alkyl,
- (4) halo $C_{1-6}$ alkyl,
- (5) $C_{2-6}$ alkenyl, or
- (6) $C_{1-6}$ alkoxy-$C_{1-6}$ alkyl;

$R^2$ and $R^3$ are each independently
- (1) hydrogen,
- (2) $C_{1-6}$ alkyl,
- (3) halo,
- (4) carboxy,
- (5) $C_{1-6}$ alkoxy,
- (6) phenyl,
- (7) $C_{1-6}$ alkylcarbonyl,
- (8) di-($C_{1-6}$ alkyl)amino, or $R^2$ and $R^3$ are joined together to form the group 3,4-methylenedioxy or a furan ring;

$R_4$ is

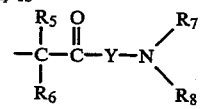

wherein $R_5$ and $R_6$ are each individually hydrogen or $C_{1-3}$ alkyl;

Y is (a)

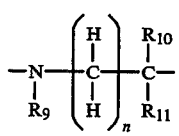

$R_7$ and $R_8$ are each individually
- (a) hydrogen,
- (b) $C_{1-6}$ alkyl,
- (c) hydroxy $C_{2-6}$ alkyl,
- (d) $C_{3-5}$ cycloalkyl,
- (e) $C_{1-6}$ alkylcarbonyl,
- (f) $C_{1-6}$ alkyloxy carbonyl,
- (g) amino carbonyl $C_{1-6}$ alkyl, wherein the amino is optionally mono or di substituted with $C_{1-6}$ alkyl, or
- (h) carboxy $C_{1-6}$ alkyl,
- (i) $C_{1-6}$ alkoxycarbonyl $C_{1-6}$ alkyl,
- (j) mono or di substituted benzyl or mono or di substituted pyridylmethyl, wherein the substituents are $X_1$ and $X_2$, wherein $X_1$ is
- (1) hydrogen,
- (2) halo,
- (3) $C_{1-6}$ alkyl,
- (4) halo-$C_{1-6}$ alkyl,
- (5) $C_{2-6}$ alkenyl,
- (6) hydroxy-$C_{1-6}$ alkyl,
- (7) $C_{1-6}$ alkylcarbonyl, or
- (8) $C_{1-6}$ alkylcarbonylamino; and $X_2$ is hydrogen, halo or $C_{1-6}$ alkyl;

n is 1, 2 or 3; and $R_9$, $R_{10}$ and $R_{11}$ are each independently selected from hydrogen, $C_{1-4}$ alkyl, and $C_{1-3}$ alkoxy $C_{1-3}$ alkyl; or wherein $R_7$ and $R_8$ are joined together to form mono or di substituted ring of 5, 6, or 7 atoms selected from
- (1) piperidinyl,
- (2) piperazinyl,
- (3) morpholinyl,
- (4) pyrroylidinyl,
- (5) pyrryl, and
- (6) imidazolyl, wherein the substituents are each selected from the group consisting of hydrogen and $C_{1-3}$ alkyl; or $R_8$ and $R_9$ are joined together with the nitrogens to which they are attached there is formed a saturated monocyclic ring of 6 to 7 atoms having two hetero atoms; or $R_9$ and $R_{10}$ are joined together with the nitrogen to which $R_9$ is attached there is formed a saturated monocyclic ring of 5 to 7 atoms having one hetero atom.

2. A compound which is
2-(S)-2[2-[4-methyl-piperazin-1-yl]-2-oxoethoxy]-3,3-diethyl-N-[1-(R)-(4-methylphenyl)butyl]-4-oxo-1-azetidinecarboxamide; or
2-(S)-2-[2-[4-methyl-piperazin-1-oxo-ethoxy]-3,3-diethyl-N-[1-(R)-(3,4-methylenedioxyphenyl)-butyl]-4-oxo-1-azetidinecarboxamide.

3. A compound according to claim 2 wherein at least one of $R_5$ and $R_6$ is other than hydrogen.

4. A compound of Formula I

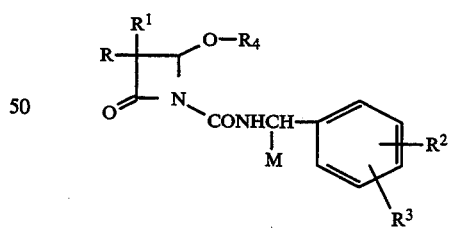

or a pharmaceutically acceptable salt thereof wherein:

wherein

R is $C_{1-3}$ alkyl;

$R_1$ is $C_{1-3}$ alkyl;

M is
- (a) $C_{1-6}$ alkyl, or
- (b) $C_{2-6}$ alkenyl;

$R^2$ is
- (a) hydrogen
- (b) $C_{1-6}$ alkyl, or $C_{1-6}$ alkoxy, and $R^3$ is hydrogen, or $R^2$ and $R^3$ are joined together to form the group 3,4-methylenedioxy or a furan ring;

R4 is

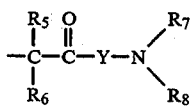

R5 is hydrogen or $C_{1-3}$ alkyl;
R6 is hydrogen;
Y is

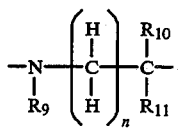

R7 and R8 are each independently selected from
  (a) hydrogen,
  (b) $C_{1-3}$ alkyl,
  (c) $C_{1-3}$ alkoxy $C_{2-3}$ alkyl,
  (d) aminocarbonylmethyl,
  (e) substituted benzyl wherein the substituents are $X_1$ and $X_2$
  wherein $X_1$ is hydrogen and $X_2$ is
    (1) hydrogen,
    (2) halo, or
    (3) $C_{1-3}$ alkyl;
  n is 1, 2 or 3, and
R9, R10 and R11 are each independently selected from
  hydrogen,
  $C_{1-4}$ alkyl, and $C_{1-3}$ alkoxy $C_{1-3}$ alkyl; or
R7 and R8 are joined together to form a substituted ring selected from
  (a) piperidinyl,
  (b) piperazinyl, and
  (c) morpholinyl; or
R8 and R9 are joined together with the nitrogens connecting them to form an unsubstituted saturated monocyclic ring of 6 to 7 atoms having two hetero atoms; or
R9 and R10 are joined together with the atoms connecting them to form an unsubstituted saturated monocyclic ring of 5 to 7 atoms having one hereto atom.

5. A compound according to claim 4 wherein
R is methyl or ethyl;
R1 is methyl or ethyl;
M is
  (a) $C_{1-4}$ alkyl, or
  (b) $C_{2-3}$ alkenyl;
$R^2$ is
  (a) hydrogen,
  (b) $C_{1-3}$ alkyl, or $C_{1-3}$ alkoxy, and
$R^3$ is hydrogen, or
$R^2$ and $R^3$ are joined together to form the group 3,4-methylenedioxy or a furan ring;
Y is

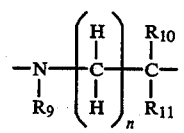

n is 1 or 2;
R7 and R8 are each independently selected from
  (a) hydrogen,
  (b) $C_{1-3}$ alkyl,
  (c) $C_{1-3}$ alkoxy $C_{2-3}$ alkyl,
  (d) aminocarbonylmethyl,
  (e) substituted benzyl wherein the substituents are $X_1$ and $X_2$
  wherein $X_1$ is hydrogen and $X_2$ is
    (1) hydrogen,
    (2) halo, or
    (3) $C_{1-3}$ alkyl;
R9, R10 and R11 are each independently selected from
  (a) hydrogen,
  (b) C1-3 alkyl, or
  (c) $Ci_{1-3}$ alkoxy $C_{1-3}$ alkyl,
R7 and R8 are joined together to form a substituted ring selected from
  (a) piperidinyl, and
  (c) morpholinyl.

6. A compound according to claim 2 wherein R5 and R6 are each hydrogen.

7. A compound according to claim 6 wherein
R is $C_{1-3}$ alkyl;
R1 is $C_{1-3}$ alkyl;
M is
  (a) $C_{1-6}$ alkyl, or
  (b) $C_{2-6}$ alkenyl;
$R^2$ is
  (a) hydrogen
  (b) $C_{1-6}$ alkyl, or $C_{1-6}$ alkoxy, and
$R^3$ is hydrogen, or
$R^2$ and $R^3$ are joined together to form the group 3,4-methylenedioxy or a furan ring;
Y is

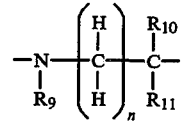

R7 and R8 are each independently selected from
  (a) hydrogen,
  (b) $C_{1-3}$ alkyl,
  (c) $C_{1-3}$ alkoxy $C_{2-3}$ alkyl,
  (d) aminocarbonylmethyl wherein the amino is optionally mono or di substituted with $C_{1-3}$ alkyl,
  (e) substituted benzyl or pyridylmethyl wherein the substituents are $X_1$ and $X_2$
  wherein $X_1$ is hydrogen and $X_2$ is
    (1) hydrogen
    (2) halo or
    (3) $C_{1-3}$ alkyl;
  n is 1, 2 or 3; and
R9, R10 and R11 are each independently selected from
  hydrogen, $C_{1-4}$ alkyl, and $C_{1-3}$ alkoxy $C_{1-3}$ alkyl; or
wherein R7 and R8 are joined together to form mono or di substituted ring of 5, 6, or 7 atoms selected from
  (1) piperidinyl,
  (2) piperazinyl,
  (3) morpholinyl,
  (4) pyrroylidinyl,
  (5) pyrryl, and
  (6) imidazolyl,
wherein the substituents are each selected from the group consisting of hydrogen and $C_{1-3}$ alkyl; or R8 and R9 are joined together with the nitrogens connecting them to form an unsubstituted saturated monocyclic ring of 6 to 7 atoms having two hetero atoms; or $R_9$ and $R_{10}$ are joined together with the atoms connecting them to form an unsubstituted saturated monocyclic ring of 5 to 7 atoms having one hetero atom.

8. A compound according to claim 7 wherein
R is methyl or ethyl;
$R_1$ is methyl or ethyl;
M is
   (a) $C_{1-4}$ alkyl, or
   (b) $C_{2-3}$ alkenyl;
$R^2$ is
   (a) hydrogen,
   (b) $C_{1-3}$ alkyl, or $C_{1-3}$ alkoxy, and
$R^3$ is hydrogen, or
$R^2$ and $R^3$ are joined together to form the group 3,4-methylenedioxy or a furan ring;
Y is

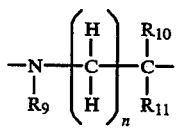

$R_7$ and $R_8$ are each independently selected frown
   (a) hydrogen,
   (b) $C_{1-3}$ alkyl,
   (c) $C_{1-3}$ alkoxy $C_{2-3}$ alkyl,
   (d) aminocarbonylmethyl
n is 1, 2 or 3; and
$R_9$, $R_{10}$ and $R_{11}$ are each independently selected from hydrogen,
   $C_{1-4}$ alkyl, and $C_{1-3}$ alkoxy $C_{1-3}$ alkyl; or
wherein $R_7$ and $R_8$ are joined together to form mono or di substituted ring of 5, 6, or 7 atoms selected from
   (1) piperidinyl,
   (2) morpholinyl, and
   (3) imidazolyl,
wherein the substituents are each selected from the group consisting of hydrogen and $C_{1-3}$ alkyl; or $R_8$ and $R_9$ are joined together with the nitrogens connecting them to form an unsubstituted saturated monocyclic ring of 6 to 7 atoms having two hereto atoms; or $R_9$ and $R_{10}$ are joined together with the atoms connecting them to form an unsubstituted saturated monocyclic ring of 5 to 7 atoms having one hetero atom.

9. A compound of the Formula (I)

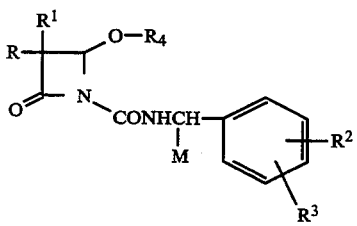

or a pharmaceutically acceptable salt thereof wherein:
R is $C_{1-6}$ alkyl;
$R^1$ is $C_{1-6}$ alkyl or $C_{1-6}$ alkoxy-$C_{1-6}$ alkyl;
M is
   (1) hydrogen,
   (2) $C_{1-6}$ alkyl,
   (3) hydroxy $C_{1-6}$ alkyl,
   (4) halo $C_{1-6}$ alkyl,
   (5) $C_{2-6}$ alkenyl, or
   (6) $C_{1-6}$ alkoxy-$C_{1-6}$ alkyl;
$R^2$ and $R^3$ are each independently
   (1) hydrogen,
   (2) $C_{1-6}$ alkyl,
   (3) halo,
   (4) carboxy,
   (5) $C_{1-6}$ alkoxy,
   (6) phenyl,
   (7) $C_{1-6}$ alkylcarbonyl,
   (8) di-($C_{1-6}$ alkyl)amino, or
$R^2$ and $R^3$ are joined together to form the group 3,4-methylenedioxy or a furan ring;
$R_4$ is

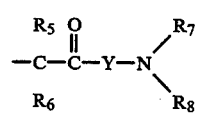

$R_5$ and $R_6$ are each individually hydrogen or $C_{1-3}$ alkyl;
Y is

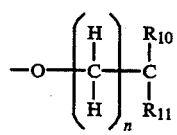

$R_7$ and $R_8$ are each individually
   (a) hydrogen,
   (b) $C_{1-6}$ alkyl,
   (c) $C_{1-6}$ alkyloxy $C_{2-6}$ alkyl;
n is 1, 2 or 3; and $R_{10}$ and $R_{11}$ are each independently selected from hydrogen, $C_{1-4}$ alkyl, and $C_{1-3}$ alkoxy $C_{1-3}$ alkyl; or
wherein $R_7$ and $R_8$ are joined together to form mono or di substituted ring of 5, 6, or 7 atoms selected from
   (1) piperidinyl,
   (2) piperazinyl,
   (3) morpholinyl,
   (4) pyrroylidinyl,
   (5) pyrryl, and
   (6) imidazolyl,
wherein the substituents are each selected from the group consisting of hydrogen and $C_{1-3}$ alkyl.

10. A compound according to claim 9 wherein $R_5$ and $R_6$ are each hydrogen.

11. A compound according to claim 10 wherein
R is $C_{1-3}$ alkyl;
$R_1$ is $C_{1-3}$ alkyl;
M is
   (a) $C_{1-6}$ alkyl, or
   (b) $C_{2-6}$ alkenyl;
$R^2$ is
   (a) hydrogen
   (b) $C_{1-6}$ alkyl, or $C_{1-6}$ alkoxy, and
$R^3$ is hydrogen, or
$R^2$ and $R^3$ are joined together to form the group 3,4-methylenedioxy or a furan ring;
Y is

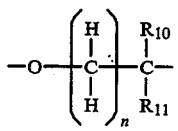

n is 1 or 2;
R7 and R8 are each independently selected from
(a) hydrogen,
(b) $C_{1-3}$ alkyl,
(c) $C_{1-3}$ alkoxy $C_{2-3}$ alkyl,
or
R7 and R8 are joined together to form a substituted ring selected from
(a) piperidinyl,
(b) piperazinyl,
(c) morpholinyl, and
(d) imidazolyl.

12. A compound according to claim 11 wherein
R is methyl or ethyl;
$R_1$ is methyl or ethyl;
M is
(a) $C_{1-4}$ alkyl, or
(b) $C_{2-3}$ alkenyl;
$R^2$ is
(a) hydrogen,
(b) $C_{1-3}$ alkyl, or $C_{1-3}$ alkoxy, and
$R^3$ is hydrogen, or
$R^2$ and $R^3$ are joined together to form the group 3,4-methylenedioxy or a furan ring;
Y is

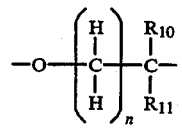

n is 1;
R7 and R8 are each independently selected from
(a) $C_{1-3}$ alkyl,
(b) $C_{1-3}$ alkoxy $C_{2-3}$ alkyl,
or
R7 and R8 are joined together to form a substituted ring selected from
(a) piperidinyl,
(b) morpholinyl, and
(c) imidazolyl.

13. A compound of the Formula (I)

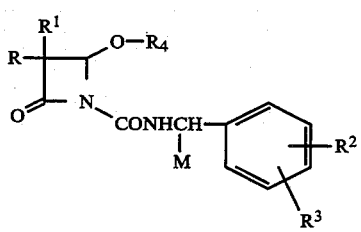

I or a pharmaceutically acceptable salt thereof wherein:
R is $C_{1-6}$ alkyl;
$R^1$ is $C_{1-6}$ alkyl or $C_{1-6}$ alkoxy-$C_{1-6}$ alkyl;
M is
(1) hydrogen,
(2) $C_{1-6}$ alkyl,
(3) hydroxy $C_{1-6}$ alkyl,
(4) halo $C_{1-6}$ alkyl,
(5) $C_{2-6}$ alkenyl, or
(6) $C_{1-6}$ alkoxy-$C_{1-6}$ alkyl;
$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) di-($C_{1-6}$alkyl)amino, or
$R_2$ and $R_3$ are joined together to form the group 3,4-methylenedioxy or a furan ring;
$R_4$ is

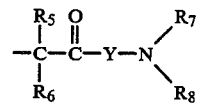

$R_5$ and $R_6$ are each individually hydrogen or $C_{1-6}$ alkyl;
Y is
(a)

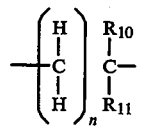

or
(b) a co-valent bond;
R7 and R8 are each individually
(a) hydrogen,
(b) $C_{1-6}$ alkyl,
(c) $C_{1-6}$ alkyloxy $C_{2-3}$ alkyl, or wherein R7 and R8 are joined together to form mono or di substituted ring of 5, 6, or 7 atoms selected from
(1) piperidinyl,
(2) piperazinyl,
(3) morpholinyl,
(4) pyrroylidinyl,
(5) pyrryl, and
(6) imidazolyl,
wherein the substituents are each selected from the group consisting of hydrogen and $C_{1-3}$ alkyl; and wherein n is 0, 1, 2 or 3 and wherein $R_{10}$ and $R_{11}$, are each independently selected from hydrogen, $C_{1-3}$ alkyl, and $C_{1-3}$ alkoxy $C_{1-3}$alkyl.

14. A compound according to claim 13 wherein $R_5$ and $R_6$ are each hydrogen.

15. A compound according to claim 14 wherein
R is $C_{1-3}$ alkyl;
$R_1$ is $C_{1-3}$ alkyl;
M is
(a) $C_{1-6}$ alkyl, or
(b) $C_{2-6}$ alkenyl;
$R^2$ is
(a) hydrogen
(b) $C_{1-6}$ alkyl, or $C_{1-6}$ alkoxy, and
$R^3$ is hydrogen, or
$R^2$ and $R^3$ are joined together to form the group 3,4-methylenedioxy or a furan ring;
Y is

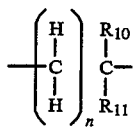

or
(b) a co-valent bond;
$R_7$ and $R_8$ are each independently selected from
  (a) hydrogen,
  (b) $C_{1-3}$ alkyl,
  (c) $C_{1-3}$ alkoxy $C_{2-3}$ alkyl,
or
$R_7$ and $R_8$ are joined together to form a substituted ring selected from
  (a) piperidinyl,
  (b) piperazinyl,
  (c) pyrrolidinyl,
  (d) morpholinyl, and
  (e) imidazolyl.

16. A compound according to claim 15 wherein
R is methyl or ethyl;
$R_1$ is methyl or ethyl;
M is
  (a) $C_{1-4}$ alkyl, or
  (b) $C_{2-3}$ alkenyl;
$R_2$ is
  (a) hydrogen,
  (b) $C_{1-3}$ alkyl, or $C_{1-3}$ alkoxy, and
$R_3$ is hydrogen, or
$R^2$ and $R^3$ are joined together to form the group 3,4-methylenedioxy or a furan ring;
$R_5$ and $R_6$ are each individually hydrogen;
Y is
  (a)

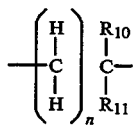

or
(b) a co-valent bond;
n is 0 or 1;
$R_7$ and $R_8$ are each independently selected from
  (a) $C_{1-3}$ alkyl,
  (b) $C_{1-3}$ alkoxy $C_{2-3}$ alkyl,
or
$R_7$ and $R_8$ are joined together to form a substituted ring selected from
  (a) piperidinyl,
  (b) morpholinyl, and
  (c) imidazolyl.

17. A compound selected from the group consisting of
(a) 2-(S)-[2-[[2-((Aminocarbonylmethyl)ethylamino)ethyl]-ethylamino]-2-oxoethoxy]-3,3-diethyl-N-[1-(R)-(4-methylphenyl)butyl]-4-oxo-1-azetidinecarboxamide;
(b) 2-(S)-[2-[[2-(Dimethylamino)ethy]-ethylamino]-2-oxo-ethoxy]-3,3-diethyl-N-[1-(R)-(benzofuran-5-yl) butyl]-4-oxo-1-azetidinecarboxamide;
(c) 2-(S)-[2-[[2-(Diethylamino)ethy]-ethylamino]-2-oxoethoxy]-3,3-diethyl-N-[1-(R)-(benzofuran-5-yl)butyl]-4-oxo-1-azetidinecarboxamide;
(d) 2-(S)-[2-[[2-(Diethylamino)ethy]-methylamino]-2-oxoethoxy]-3,3-diethyl-N-[1-(R)-(benzofuran-5-yl)butyl]-4-oxo-1-azetidinecarboxamide;
(e) 2-(S)-[2-[[2-(Dimethylamino)ethy]-methylamino]-2-oxoethoxy]-3,3-diethyl-N-[1-(R)-(benzofuran-5-yl)butyl]-4-oxo-1-azetidinecarboxamide;
(f) 2-(S)-[2-[[2-(Dimethylamino)ethy]-ethylamino]-2-oxo-ethoxyphenyl]-3,3-diethyl-N-[1-(R)-(3,4-methylenedioxyphenyl)-butyl]-4-oxo-1-azetidinecarboxamide;
(g) 2-(S)-[2-[[2-(Diethylamino)ethy]-ethylamino]-2-oxoethoxy]-3,3-diethyl-N-[1-(R)-(3,4-methylenedioxyphenyl)butyl]-4-oxo-1-azetidinecarboxamide; and
(h) 2-(S)-[2-[[2-(2-Methoxyethyl)methylamino)ethy]-ethylamino]-2-oxoethoxy]-3,3-diethyl-N-[1-(R)-(3,4-methylenedioxyphenyl)butyl]-4-oxo-1-azetidinecarboxamide.

18. A compound selected from the group consisting of
(1) 2-(S)-[2-[[2-(Diethylamino)ethyl]propylamino]-2-oxoethoxy]-3,3-diethyl-N-[1-(R)-(4-methylphenyl)butyl]-4-oxo-1-azetidinecarboxamide;
(2) 2-(S)-[2-[[2-((2-Methoxyethyl)-ethylamino)ethyl]isopropylamino]-2-oxoethoxy]-3,3-diethyl-N-[1-(R)-(4-methylphenyl)butyl]-4-oxo-1-azetidinecarboxamide;
(3) 2-(S)-[2-[[2-((2-Methoxyethyl)-methylamino)ethyl]ethylamino]-2-oxoethoxy]-3,3-diethyl-N-[1-(R)-(4-methylphenyl)butyl]-4-oxo-1-azetidinecarboxamide;
(4) 2-(S)-[2-[[2-(Isopropylmethylamino)ethyl]methylamino]-2-oxoethoxy]-3,3-diethyl-N-[1-(R)-(4-methylphenyl)butyl]-4-oxo-1-azetidinecarboxamide;
(5) 2-(S)-[2-[[2-(Dimethylamino)ethyl]methylamino]-2-oxo-(1-(S)-methyl)ethoxy]-3,3-diethyl-N-[1-(R)-(4-methylphenyl)butyl]-4-oxo-1-azetidinecarboxamide;
(6) 2-(S)-[2-[[2-(Diethylamino)ethyl]amino]-2-oxo-(1-(S)-methyl)ethoxy]-3,3-diethyl-N-[1-(R)-(4-methylphenyl)butyl]-4-oxo-1-azetidinecarboxamide;
(7) 2-(S)-[2-[[2-(Dimethylamino)ethyl]amino]-2-oxo-(1-(S)-methyl)ethoxy]-3,3-diethyl-N-[1-(R)-(4-methylphenyl)butyl]-4-oxo-1-azetidinecarboxamide;
(8) 2-(S)-[2-[[2-(Morpholin-1-yl)ethyl]amino]-2-oxo-1-(S)-methyl)ethoxy]-3,3-diethyl-N-[1-(R)-(4-methylphenyl)butyl]-4-oxo-1-azetidinecarboxamide;
(9) 2-(S)-[2-[[2-(Diisopropylamino)ethyl]amino]-2-oxo-(1-(S)-methyl)ethoxy]-3,3-diethyl-N-[1-(R)-(4-methylphenyl)butyl]-4-oxo-1-azetidinecarboxamide;
(10) 2-(S)-[2-[[2-(Dimethylamino)ethyl]ethylamino]-2-oxo-(1-(S)-methyl)ethoxy]-3,3-diethyl-N-[1-(R)-(4-methylphenyl)butyl]-4-oxo-1-azetidinecarboxamide; and
(11) 2-(S)-[2-[[2-(Diethylamino)ethyl]methylamino]-2-oxo-(1-(S)-methyl)ethoxy]-3,3-diethyl-N-[1-(R)-(4-methylphenyl)butyl]-4-oxo-1-azetidinecarboxamide;
(12) 2-(S)-[4-Ethylamino-2-oxo-butoxy]-3,3-diethyl-N-[1-(R)-(4-methylphenyl)butyl]-4-oxo-1-azetidinecarboxamide;
(13) 2-(S)-[4-Diethylamino-2-oxo-butoxy]-3,3-diethyl-N-[1-(R)-(4-methylphenyl)butyl]-4-oxo-1-azetidinecarboxamide;
(14) 2-(S)-[2-[[2-(Ethylmethylamino)ethyl]-ethylamino]-2-oxoethoxy]-3,3-diethyl-N-[1-(R)-(4-methyl-phenyl)-butyl]-4-oxo-1-azetidinecarboxamide;

(15) 2-(S)-[2-[[2-Methylaminoethyl]-ethylamino]-2-oxoeth-oxy]-3,3-diethyl-N-[1-(R)-(4-methylphenyl)butyl]-4-oxo-1-azetidinecarboxamide;

(16) 2-(S)-[2-[[2-ethylamino-ethyl]-methylamino]-2-oxo-ethoxy]-3,3-diethyl-N-[1-(R)-(4-methylphenyl)butyl]-4-oxo-1-azetidinecarboxamide;

(17) 2-(S)-[2-[[2-Aminoethyl]-ethylamino-2-oxo-ethoxy]-3,3-diethyl-N-[1-(R)-(4-methylphenyl)butyl]-4-oxo-1-azetidinecarboxamide;

(18) 2-(S)-[2-[[2-ethylaminoethyl]-amino]-2-oxoethoxy]-3,3-diethyl-N-[1-(R)-(4-methylphenyl)-butyl]-4-oxo-1-azetidinecarboxamide;

(19) 2-(S)-[2-[[2-(Dimethylamino)ethyl]ethylamino]-2-oxo-1,1-dimethyl-ethoxy]-3,3-diethyl-N-[1-(R)-(4-methyl-phenyl)butyl]-4-oxo-1-azetidinecarboxamide;

(20) 2-(S)-[2-[[2-(Dimethylamino)ethyl]methylamino]-2-oxo-1,1-dimethyl-ethoxy]-3,3-diethyl-N-[1-(R)-(4-methylphenyl)butyl]-4-oxo-1-azetidinecarboxamide;

(21) 2-(S)-[2-[[2-(Diethylamino)ethyl]ethylamino]-2-oxo-1,1-dimethyl-ethoxy]-3,3-diethyl-N-[1-(R)-(4-methylphenyl)butyl]-4-oxo-1-azetidinecarboxamide;

(22) 2-(S)-[2-[[2-(Isopropylmethylamino)ethyl]methylamino]-2-oxo-1,1-dimethyl-ethoxy]-3,3-diethyl-N-[1-(R)-(4-methylphenyl)butyl]-4-oxo-1-azetidinecarboxamide;

(23) 2-(S)-[2-[[2-((2-Methoxyethyl)-methylamino)-ethyl]ethylamino]-2-oxo-1,1-dimethyl-ethoxy]3,3-diethyl-N-[1-(R)-(4-methylphenyl)butyl]-4-oxo-1-azetidinecarboxamide; and

(24) 2-(S)-[2-(4-Morpholinyl)-2-oxoethoxy]-3,3-diethyl-N-[1-(R)-(4-methylphenyl)butyl]-4-oxo-1- azetidinecarboxamide.

19. A pharmaceutical composition for the inhibition of human leukocyte elastase which comprises a nontoxic therapeutically effective amount of a compound of claim 1 and a pharmaceutically acceptable carrier.

20. A method of treatment for the inhibition of human leukocyte elastase which comprises the administration to a subject in need of such inhibition a nontoxic therapeutically effective amount of a compound of claim 1.

21. A compound which is
2-(S)-[2-[[2-(Dimethylamino)ethyl]methylamino]-2-oxoethoxy]-3,3-diethyl-N-[1-(R)-(4-methylphenyl)butyl]-4-oxo-1-azetidinecarboxamide;
2-(S)-[2-[[2-(Dimethylamino)ethyl]ethylamino]-2-oxoethoxy]-3,3-diethyl-N-[1-(R)-(4-methylphenyl) butyl]-4-oxo-1-azetidinecarboxamide or the L-malic acid salt thereof; or
2-(S)-[2-[[2-((2-Methoxyethyl)-methylamino)ethyl] ethylamino]-2-oxoethoxy]-3,3-diethyl-N-[1-(R)-(4-methylphenyl)butyl]-4-oxo-1-azetidinecarboxamide.

22. A pharmaceutical composition for the inhibition of human leukocyte elastase which comprises a nontoxic therapeutically effective amount of a compound of claim 21 and a pharmaceutically acceptable carrier.

23. A compound of the Formula (I)

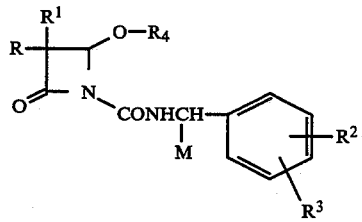

or a pharmaceutically acceptable salt thereof wherein:

R is $C_{1-6}$ alkyl;
$R^1$ is $C_{1-6}$ alkyl or $C_{1-6}$ alkoxy-$C_{1-6}$ alkyl;
M is
 (1) hydrogen,
 (2) $C_{1-6}$ alkyl,
 (3) hydroxy $C_{1-6}$ alkyl,
 (4) halo $C_{1-6}$ alkyl,
 (5) $C_{2-6}$ alkenyl, or
 (6) $C_{1-6}$ alkoxy-$C_{1-6}$ alkyl;
$R^2$ and $R^3$ are each independently
 (1) hydrogen,
 (2) $C_{1-6}$ alkyl,
 (3) halo,
 (4) carboxy,
 (5) $C_{1-6}$ alkoxy,
 (6) phenyl,
 (7) $C_{1-6}$ alkylcarbonyl,
 (8) di-($C_{1-6}$ alkyl)amino, or
$R^2$ and $R^3$ are joined together to form the group 3,4-methylenedioxy or a furan ring;
$R_4$ is

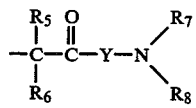

wherein
$R_5$ and $R_6$ are each individually hydrogen or $C_{1-3}$ alkyl;
Y is

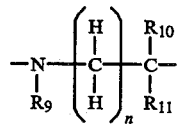

$R_7$ and $R_8$ are each individually
 (a) hydrogen,
 (b) $C_{1-6}$ alkyl,
 (c) hydroxy $C_{2-6}$alkyl,
 (d) $C_{3-5}$ cycloalkyl,
 (e) $C_{1-6}$ alkylcarbonyl,
 (f) $C_{1-6}$ alkyloxy carbonyl,
 (g) amino carbonyl $C_{0-6}$ alkyl, wherein the amino is optionally mono or di substituted with $C_{1-6}$ alkyl, or
 (h) carboxy $C_{1-6}$ alkyl,
 (i) $C_{1-6}$ alkoxycarbonyl $C_{1-6}$ alkyl,
 (j) mono or di substituted benzyl or mono or di substituted pyridylmethyl, wherein the substituents are $X_1$ and $X_2$,
wherein
$X_1$ is
 (1) hydrogen,
 (2) halo,
 (3) $C_{1-6}$ alkyl,
 (4) halo-$C_{1-6}$ alkyl,
 (5) $C_{2-6}$ alkenyl,
 (6) hydroxy-$C_{1-6}$ alkyl,
 (7) $C_{1-6}$ alkylcarbonyl, or
 (8) $C_{1-6}$ alkylcarbonylamino; and
$X_2$ is hydrogen, halo or $C_{1-6}$ alkyl;
n is 1, 2 or 3;
$R_9$, $R_{10}$ and $R_{11}$ are each independently selected from hydrogen, $C_{1-4}$ alkyl, and $C_{1-3}$ alkoxy $C_{1-3}$ alkyl; or wherein $R_7$ and $R_8$ are joined together to form mono or di substituted ring of 5, 6, or 7 atoms selected from
- (1) piperidinyl,
- (2) piperazinyl,
- (3) morpholinyl,
- (4) pyrroylidinyl,
- (5) pyrryl, and
- (6) imidazolyl, wherein the substituents are each selected from the group consisting of hydrogen and $C_{1-3}$ alkyl; or $R_8$ and $R_9$ may be joined together with the atoms connecting them to form a mono or di substituted monocyclic saturated ring of 6 to 7 atoms and having two hetero atoms including the nitrogens to which they are attached; $R_9$ and $R_{10}$ may be joined together with the atoms connecting them to form a mono or di substituted monocyclic saturated ring of 5 to 7 atoms and having one hetero atom including the nitrogen to which $R_9$ is attached; or $R_8$ and $R_{10}$ may be joined together with the atoms connecting them to form a mono or di substituted monocyclic saturated ring of 5 to 7 atoms including the atoms to which they are attached, said ring having one hetero atom;

wherein the substituents on the rings formed by $R_8$ and $R_{10}$ or $R_8$ and $R_9$ are selected from hydrogen, $C_{1-3}$ alkyl and cyclopropyl; and the substitutents on the ring formed by joining $R_9$ and $R_{10}$ is selected from hydrogen and $C_{1-3}$ alkyl.

24. A compound according to claim 23 wherein
R is $C_{1-6}$ alkyl;
$R^1$ is $C_{1-6}$ alkyl or $C_{1-6}$ alkoxy-$C_{1-6}$ alkyl;
M is
- (1) hydrogen,
- (2) $C_{1-6}$ alkyl,
- (3) hydroxy $C_{1-6}$ alkyl,
- (4) halo $C_{1-6}$ alkyl,
- (5) $C_{2-6}$ alkenyl, or
- (6) $C_{1-6}$ alkoxy-$C_{1-6}$ alkyl;

$R^2$ and $R^3$ are each independently
- (1) hydrogen,
- (2) $C_{1-6}$ alkyl,
- (3) halo,
- (4) carboxy,
- (5) $C_{1-6}$ alkoxy,
- (6) phenyl,
- (7) $C_{1-6}$ alkylcarbonyl,
- (8) di-($C_{1-6}$ alkyl)amino, or $R^2$ and $R^3$ are joined together to form the group 3,4-methylenedioxy or a furan ring;

$R_4$ is $$-\overset{R_5}{\underset{R_6}{C}}-\overset{O}{\overset{\|}{C}}-Y-N\overset{R_7}{\underset{R_8}{\diagup}}$$

wherein
$R_5$ and $R_6$ are each individually hydrogen or $C_{1-3}$ alkyl;
Y is $$-N{\underset{R_9}{\overset{|}{-}}}{\left(\underset{H}{\overset{H}{\underset{|}{\overset{|}{C}}}}\right)_n}{\underset{R_{11}}{\overset{R_{10}}{\underset{|}{\overset{|}{C}}}}}-$$

$R_7$ is
- (a) $C_{1-3}$ alkyl, 2-hydroxyethyl or cyclopropyl,
- (b) $C_{1-3}$ alkoxy $C_{2-3}$ alkyl,
- (c) acetyl,
- (d) $C_{1-3}$ alkoxycarbonylmethyl,
- (e) aminocarbonyl methyl,
- (f) hydrogen,
- (g) mono or di substituted benzyl or mono or di substituted pyridylmethyl, wherein the substitutents are $X_1$ and $X_2$, wherein
$X_1$ is
- (1) hydrogen,
- (2) halo,
- (3) $C_{1-6}$ alkyl,
- (4) halo-$C_{1-6}$ alkyl,
- (5) $C_{2-6}$ alkenyl,
- (6) hydroxy-$C_{1-6}$ alkyl,
- (7) $C_{1-6}$ alkylcarbonyl, or
- (8) $C_{1-6}$ alkylcarbonylamino; and $X_2$ is hydrogen, halo or $C_{1-6}$ alkyl;
n is 1, 2 or 3; and
$R_{10}$ and $R_{11}$ are each independently selected from hydrogen, $C_{1-4}$ alkyl, and $C_{1-3}$ alkoxy $C_{1-3}$ alkyl; and $R_8$ and $R_9$ are joined together so that together with the nitrogens to which they are attached there is formed a mono or di substituted saturated monocyclic ring which is piperazinyl or homopiperazinyl, wherein the substitutents are independently selected from H $C_{1-3}$ alkyl and cyclopropyl.

25. A compound according to claim 24 wherein $R_5$ and $R_6$ are each hydrogen and n is 1.

26. A compound according to claim 25 wherein
R is $C_{1-3}$ alkyl;
$R_1$ is $C_{1-3}$ alkyl;
M is
- (a) $C_{1-6}$ alkyl, or
- (b) $C_{2-6}$ alkenyl;

$R^2$ is
- (a) hydrogen
- (b) $C_{1-6}$ alkyl, or $C_{1-6}$ alkoxy, and $R^3$ is hydrogen, or
$R^2$ and $R^3$ are joined together to form the group 3,4-methylenedioxy or a furan ring;
Y is $$-N{\underset{R_9}{\overset{|}{-}}}{\left(\underset{H}{\overset{H}{\underset{|}{\overset{|}{C}}}}\right)_n}{\underset{R_{11}}{\overset{R_{10}}{\underset{|}{\overset{|}{C}}}}}-$$

$R_7$ is
- (a) $C_{1-3}$ alkyl, 2-hydroxyethyl or cyclopropyl,
- (b) $C_{1-3}$ alkoxy $C_{2-3}$ alkyl,
- (c) acetyl,
- (d) $C_{1-3}$ alkoxycarbonylmethyl,
- (e) aminocarbonyl methyl, (f) hydrogen,
(g) substituted benzyl wherein the substituents are $X_1$ and $X_2$
wherein $X_1$ is hydrogen and $X_2$ is
  (1) hydrogen,
  (2) halo, or
  (3) $C_{1-3}$ alkyl;
$R_{10}$ and $R_{11}$ are each independently selected from hydrogen, $C_{1-4}$ alkyl, and $C_{1-3}$ alkoxy $C_{1-3}$ alkyl; and
$R_8$ and $R_9$ are joined together so that together with the nitrogens to which they are attached there is formed a mono substituted saturated monocyclic ring which is substituted piperazinyl or homopiperazinyl wherein the substitutent is selected from H $C_{1-3}$ alkyl and cyclopropyl.

27. A compound according to claim 26 wherein
R is methyl or ethyl;
$R_1$ is methyl or ethyl;
M is
  (a) $C_{1-4}$ alkyl, or
  (b) $C_{2-3}$ alkenyl;
$R^2$ is
  (a) hydrogen,
  (b) $C_{1-3}$ alkyl, or $C_{1-3}$ alkoxy, and
$R^3$ is hydrogen, or
$R^2$ and $R^3$ are joined together to form the group 3,4-methylenedioxy or a furan ring;
Y is

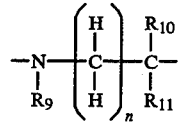

$R_{10}$ and $R_{11}$ are each hydrogen or methyl;
$R_7$ is selected from
  (a) hydrogen,
  (b) $C_{1-3}$ alkyl,
  (c) $C_{1-3}$ alkoxy $C_{2-3}$ alkyl,
  (d) aminocarbonyl $C_{1-3}$ alkyl
  (e) 2-hydroxyethyl,
  (f) cyclopropyl, and
$R_8$ and $R_9$ are joined together so that together with the nitrogens to which they are attached there is formed a mono substituted saturated monocyclic ring which is piperazinyl, wherein the substitutent is H, methyl or cyclopropyl.

* * * * *